United States Patent
Li et al.

(10) Patent No.: US 8,324,160 B2
(45) Date of Patent: Dec. 4, 2012

(54) CHIMERIC POLYPEPTIDES AND USES THEREOF

(75) Inventors: Yang Li, Mountain View, CA (US); Xinle Wu, Belmont, CA (US); Zhulun Wang, Palo Alto, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 12/817,084

(22) Filed: Jun. 16, 2010

(65) Prior Publication Data

US 2010/0323954 A1 Dec. 23, 2010

Related U.S. Application Data

(60) Provisional application No. 61/187,767, filed on Jun. 17, 2009, provisional application No. 61/265,548, filed on Dec. 1, 2009.

(51) Int. Cl.
*A61K 38/18* (2006.01)
*C07K 14/50* (2006.01)
*C12P 21/04* (2006.01)
*C12N 15/12* (2006.01)
*C07H 21/04* (2006.01)

(52) U.S. Cl. ............ 514/9.1; 435/69.7; 435/320.1; 536/23.4; 530/399; 530/402

(58) Field of Classification Search .............. None
See application file for complete search history.

(56) References Cited

U.S. PATENT DOCUMENTS

| | | | |
|---|---|---|---|
| 3,773,919 A | 11/1973 | Boswell et al. | |
| 4,179,337 A | 12/1979 | Davis et al. | |
| 4,301,144 A | 11/1981 | Iwashita et al. | |
| 4,376,110 A | 3/1983 | David et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,816,567 A | 3/1989 | Cabilly et al. | |
| 4,892,538 A | 1/1990 | Aebischer et al. | |
| 4,945,050 A | 7/1990 | Sanford et al. | |
| 4,970,154 A | 11/1990 | Chang | |
| 5,011,472 A | 4/1991 | Aebischer et al. | |
| 5,106,627 A | 4/1992 | Aebischer et al. | |
| 5,217,889 A | 6/1993 | Roninson et al. | |
| 5,229,501 A | 7/1993 | Keifer | |
| 5,234,784 A | 8/1993 | Aslam et al. | |
| 5,252,714 A | 10/1993 | Harris et al. | |
| 5,272,071 A | 12/1993 | Chappel | |
| 5,288,855 A | 2/1994 | Bergonzoni | |
| 5,364,791 A | 11/1994 | Vegeto et al. | |
| 5,489,743 A | 2/1996 | Robinson et al. | |
| 5,545,807 A | 8/1996 | Surani et al. | |
| 5,557,032 A | 9/1996 | Mak | |
| 5,585,089 A | 12/1996 | Queen et al. | |
| 5,589,362 A | 12/1996 | Bujard et al. | |
| 5,593,875 A | 1/1997 | Wurm et al. | |
| 5,635,399 A | 6/1997 | Kriegler et al. | |
| 5,650,298 A | 7/1997 | Bujard et al. | |
| 5,654,168 A | 8/1997 | Bujard et al. | |
| 5,672,510 A | 9/1997 | Eglitis et al. | |
| 5,676,954 A | 10/1997 | Brigham | |
| 5,679,559 A | 10/1997 | Kim et al. | |
| 5,693,762 A | 12/1997 | Queen et al. | |
| 5,707,632 A | 1/1998 | Williams et al. | |
| 5,811,234 A | 9/1998 | Roninson et al. | |
| 6,133,426 A | 10/2000 | Gonzales et al. | |
| 6,150,098 A | 11/2000 | Zhang | |
| 6,214,795 B1 | 4/2001 | Benjamin et al. | |
| 6,255,454 B1 | 7/2001 | Keifer et al. | |
| 6,344,546 B1 | 2/2002 | Dionne et al. | |
| 6,350,593 B1 | 2/2002 | Williams et al. | |
| 6,355,440 B1 | 3/2002 | Williams et al. | |
| 6,384,191 B1 | 5/2002 | Williams et al. | |
| 6,548,634 B1 | 4/2003 | Ballinger | |
| 6,579,850 B1 | 6/2003 | Nabeshima et al. | |
| 6,639,063 B1 | 10/2003 | Edwards | |
| 6,656,728 B1 | 12/2003 | Kavanaugh et al. | |
| 6,716,626 B1 | 4/2004 | Itoh | |
| 6,844,168 B1 | 1/2005 | Keifer et al. | |
| 7,259,248 B2 | 8/2007 | Itoh | |
| 7,381,804 B2 | 6/2008 | Osslund | |
| 7,408,047 B1 | 8/2008 | Thomason | |
| 7,459,540 B1 | 12/2008 | Thomason et al. | |
| 7,491,697 B2 | 2/2009 | Beals | |
| 7,498,416 B2 | 3/2009 | Yayon | |
| 7,531,304 B2 | 5/2009 | Bange et al. | |

(Continued)

FOREIGN PATENT DOCUMENTS

EP 0 058 481 B1 10/1986

(Continued)

OTHER PUBLICATIONS

[The] ADHR consortium (2000), "Autosomat dominant hypophosphalaemic rickets is associated with mutations in FGF23." Nature Genetics 26: 345-348.
Arner et al. (2008) "FGF21 attenuates lipolysis in human adipocytes—A possible link to improved insulin sensitivity" FEBS Letters 582: 1725-1730.
Artuc et al. (1999), "Mast cells and their mediators in cutaneous wound healing—active participants or innocent bystanders?" Exp. Dermatol. 8: 1-16.
Beck and Podolsky (1999), "Growth factors in inflammatory bowel disease," Inflamm. Bowel Dis. 5: 44-60.
Beenken and Mohammadi, (2009) "The FGF Family: biology, pathophysiology and therapy," Nature Reviews 8:235-253.
Bishop (1996), "Chromosomal insertion of foreign DNA," Reprod. Nutr. Dev. 36(6): 607-18.
Bork (2000), "Powers and pitfalls in sequence analysis: the 70% hurdle," Genome Res. 10(4): 398-400.
Bork et al. (1996), "Go hunting in sequence databases but watch out for the traps," Trends Genet. 12(10): 425-27.
Bork et al. (1998) "Predicting functions from protein sequences—where are the bottlenecks!" Nature Genetics 18(4): 313-18.
Branch (1998), "A good antisense molecule is hard to find," Trends Biochem Sci. 23(2): 45-50.
Brenner (1999), "Errors in genome annotation," Trends Genet. 15(4): 132-33.

(Continued)

*Primary Examiner* — Marianne P Allen
(74) *Attorney, Agent, or Firm* — Mary K. Hehman

(57) ABSTRACT

The disclosure provides nucleic acid molecules encoding chimeric polypeptides, chimeric polypeptides, pharmaceutical compositions comprising chimeric polypeptides, and methods for treating metabolic disorders such as diabetes and obesity using such nucleic acids, polypeptides, or pharmaceutical compositions.

12 Claims, 34 Drawing Sheets

U.S. PATENT DOCUMENTS

| | | | |
|---|---|---|---|
| 7,537,903 B2 | 5/2009 | Kuro-o | |
| 7,645,857 B2 | 1/2010 | Zhou et al. | |
| 7,667,005 B2 | 2/2010 | Nabeshima et al. | |
| 7,667,008 B2 | 2/2010 | Thomason | |
| 7,671,180 B2 | 3/2010 | Thomason | |
| 7,678,890 B2 | 3/2010 | Bosch et al. | |
| 7,695,938 B2 | 4/2010 | Thomason et al. | |
| 7,696,153 B2 | 4/2010 | Nisen | |
| 7,696,172 B2 | 4/2010 | Thomason et al. | |
| 7,700,558 B2 | 4/2010 | Thomason et al. | |
| 7,704,952 B2 | 4/2010 | Thomason et al. | |
| 7,727,742 B2 | 6/2010 | Thomason et al. | |
| 7,741,078 B2 | 6/2010 | Imamura | |
| 7,879,323 B2 | 2/2011 | Thomason et al. | |
| 7,887,799 B2 | 2/2011 | Thomason et al. | |
| 2001/0012628 A1 | 8/2001 | Agarwal et al. | |
| 2002/0081663 A1 | 6/2002 | Conklin | |
| 2002/0164713 A1 | 11/2002 | Itoh | |
| 2003/0220246 A1 | 11/2003 | Conklin | |
| 2004/0018499 A1 | 1/2004 | Lal | |
| 2004/0063910 A1 | 4/2004 | Kavanaugh et al. | |
| 2004/0185494 A1 | 9/2004 | Itoh | |
| 2004/0259780 A1 | 12/2004 | Glasebrook | |
| 2005/0037457 A1 | 2/2005 | Itoh | |
| 2005/0176631 A1 | 8/2005 | Heuer | |
| 2005/0187150 A1 | 8/2005 | Mohammadi et al. | |
| 2006/0223114 A1 | 10/2006 | Stemmer | |
| 2007/0036806 A1 | 2/2007 | Glaesner | |
| 2007/0128619 A1 | 6/2007 | Ito | |
| 2007/0142278 A1 | 6/2007 | Beals | |
| 2007/0237768 A1 | 10/2007 | Glaesner | |
| 2007/0238657 A1 | 10/2007 | Itoh | |
| 2007/0265200 A1 | 11/2007 | Glaesner | |
| 2007/0274981 A1 | 11/2007 | Sun | |
| 2007/0293430 A1 | 12/2007 | Frye | |
| 2007/0299007 A1 | 12/2007 | Frye | |
| 2008/0071065 A1 | 3/2008 | Thomason | |
| 2008/0071066 A1 | 3/2008 | Thomason | |
| 2008/0103096 A1 | 5/2008 | Frye | |
| 2008/0124344 A1 | 5/2008 | Combs et al. | |
| 2008/0242607 A1 | 10/2008 | DeFrees | |
| 2008/0248959 A1 | 10/2008 | DeFrees | |
| 2008/0253992 A1 | 10/2008 | DeFrees et al. | |
| 2008/0255040 A1 | 10/2008 | DeFrees | |
| 2008/0255045 A1 | 10/2008 | Cujec et al. | |
| 2008/0261236 A1 | 10/2008 | Kuro-o | |
| 2008/0261875 A1 | 10/2008 | Elgen | |
| 2008/0274958 A1 | 11/2008 | DeFrees | |
| 2009/0074776 A1 | 3/2009 | Itoh | |
| 2009/0098131 A1 | 4/2009 | Clark et al. | |
| 2009/0118190 A1 | 5/2009 | Beals et al. | |
| 2009/0123462 A1 | 5/2009 | Bange et al. | |
| 2009/0192087 A1 | 7/2009 | Glass et al. | |
| 2009/0202554 A1 | 8/2009 | Berezin et al. | |
| 2009/0305986 A1 | 12/2009 | Belouski et al. | |
| 2010/0047251 A1 | 2/2010 | Yayon et al. | |
| 2010/0087627 A1 | 4/2010 | Marshall et al. | |
| 2010/0158911 A1 | 6/2010 | Williams et al. | |
| 2010/0158914 A1 | 6/2010 | Desnoyers | |
| 2010/0184665 A1 | 7/2010 | Suzuki et al. | |
| 2010/0226921 A1 | 9/2010 | Thomason et al. | |
| 2010/0233169 A1 | 9/2010 | Thomason et al. | |
| 2010/0285131 A1 | 11/2010 | Belouski | |
| 2010/0310566 A1 | 12/2010 | Thomason et al. | |
| 2011/0003302 A1 | 1/2011 | Thomason et al. | |

FOREIGN PATENT DOCUMENTS

| | | | |
|---|---|---|---|
| EP | 0 143 949 B1 | 10/1988 | |
| EP | 0 154 316 B1 | 9/1989 | |
| EP | 0 036 676 B2 | 9/1990 | |
| EP | 505500 A2 | 9/1992 | |
| EP | 0545343 A1 | 6/1993 | |
| EP | 0 315 456 B1 | 6/1994 | |
| EP | 0 401 384 B1 | 3/1996 | |
| EP | 546073 B1 | 9/1997 | |
| EP | 1697420 A1 | 7/2005 | |
| EP | 2060270 A2 | 5/2009 | |
| EP | 2163626 A1 | 3/2010 | |
| WO | 90/04036 | 4/1990 | |
| WO | 91/09955 | 7/1991 | |
| WO | 91/10425 | 7/1991 | |
| WO | 91/10470 | 7/1991 | |
| WO | 91/10741 | 7/1991 | |
| WO | 93/15722 A1 | 8/1993 | |
| WO | 94/02602 | 2/1994 | |
| WO | 94/20069 A1 | 9/1994 | |
| WO | 94/28122 | 12/1994 | |
| WO | 95/05452 | 2/1995 | |
| WO | 95/34670 | 12/1995 | |
| WO | 96/11953 A1 | 4/1996 | |
| WO | 96/32478 | 10/1996 | |
| WO | 96/33735 | 10/1996 | |
| WO | 96/37609 | 11/1996 | |
| WO | 96/40958 | 12/1996 | |
| WO | 96/41865 | 12/1996 | |
| WO | 97/31899 | 9/1997 | |
| WO | 97/34631 | 9/1997 | |
| WO | 99/10494 | 3/1999 | |
| WO | 99/27100 | 6/1999 | |
| WO | 99/27100 A1 | 6/1999 | |
| WO | 00/18921 | 4/2000 | |
| WO | 00/24782 A3 | 5/2000 | |
| WO | 00/27885 A1 | 5/2000 | |
| WO | 00/54813 A1 | 9/2000 | |
| WO | 01/18172 A1 | 3/2001 | |
| WO | 0118209 A1 | 3/2001 | |
| WO | WO 01/18209 | * | 3/2001 |
| WO | 01/32678 A1 | 5/2001 | |
| WO | 01/36640 A1 | 5/2001 | |
| WO | 01/38357 A1 | 5/2001 | |
| WO | 01/49849 A1 | 7/2001 | |
| WO | 01/72957 A1 | 10/2001 | |
| WO | 02/36732 A2 | 5/2002 | |
| WO | 03/011213 A1 | 2/2003 | |
| WO | 03/059270 A1 | 7/2003 | |
| WO | 2004/022095 A1 | 3/2004 | |
| WO | 2004/083381 A2 | 9/2004 | |
| WO | 2004/100976 | 11/2004 | |
| WO | 2004/110472 | 12/2004 | |
| WO | 2005/037235 A2 | 4/2005 | |
| WO | 2005/061712 | 7/2005 | |
| WO | 2005/072769 | 8/2005 | |
| WO | 2005/091944 | 10/2005 | |
| WO | 2005/113606 | 12/2005 | |
| WO | 2006/028595 | 3/2006 | |
| WO | 2006/028714 | 3/2006 | |
| WO | 2006/050247 | 5/2006 | |
| WO | 2006/065582 | 6/2006 | |
| WO | 2006/078463 | 7/2006 | |
| WO | 2006/095559 A1 | 9/2006 | |
| WO | 2006/130527 A2 | 12/2006 | |
| WO | 2007/055789 | 5/2007 | |
| WO | 2007/100695 | 9/2007 | |
| WO | 2008/011633 | 1/2008 | |
| WO | 2008/121563 | 10/2008 | |
| WO | 2008/149521 | 11/2008 | |
| WO | 2008/151258 | 12/2008 | |
| WO | 2008/153705 | 12/2008 | |
| WO | 2009/020802 | 2/2009 | |
| WO | 2009/149171 | 12/2009 | |
| WO | 2010/006214 A1 | 1/2010 | |
| WO | 2011/047267 A1 | 4/2011 | |

OTHER PUBLICATIONS

Bruggermann et al., (1993), "Designer mice: the production of human antibody repertoires in transgenic animals" Year in Immuno. 7: 33.

Cunha et al. (1996), "Keratinocyte growth factor as mediator of mesenchymal-epithelial interactions in the development of androgen target organs." Semin Cell Dev Biol 7: 203-210.

Dailey, et al. (2005), "Mechanisms underlying differential responses to FGF signaling," Cytokine & Growth Factor Reviews 16: 233-247.

Debernardez Clark E., (1998), "Refolding of recombinant proteins" Curr. Opin. Biotechnol. 9: 157-63.

Doerks et al. (1998), "Protein annotation: detective work for function prediction," Trends Genet. 14(6): 248-50.

Ebadi et al. (1997), "Neurotrophins and their receptors in nerve injury and repair," Neurochem. Int. 30: 347-74.
Econs and McEnery (1997) "Autosomal dominant hypophosphatemic rickets/osteomalacia: clinical characterization of a novel renal phosphate-wasting disorder." J Clin Endocrinol Metab 82:674-681.
Ellison et al., (1982), "The nucleotide sequence of a human immunoglobulin Cγ1 gene" Nucleic Acids Res. 10: 4071-9).
Eswarakumar, et al. (2005) "Cellular signaling by fibroblast growth factor receptors" Cytokine & Growth Factor Reviews 16: 139-149.
Faham, S. et al., (1998) "Diversity does make a difference: fibroblast growth factor-heparin interactions," Curr. Opin. Struct. Biol. 8(5): 578-586.
Galzie Z. et al. (1997), "Fibroblast Growth Factors and their Receptors", Biochemistry and Cell Biology 75(6): 669-685.
Ghielli et al. (1998), "Regeneration processes in the kidney after acute injury: role of infiltrating cells," Exp. Nephrol. 6: 502-507.
Goldfarb (1996), "Functions of fibroblast growth factors in vertebrate development," Cytokine Growth Factor Rev. 7(4): 311-325.
Gupte, J. et al. (2011) "The FGFR D3 domain determines receptor selectivity for fibroblast growth factor 21," J. Mol. Biol. 408:491-502.
Hoogenboom et al., 1991, "By-passing immunisation. Human antibodies from synthetic repertoires of germline VH gene segments rearranged in vitro" J. Mol. Biol. 227:381.
Hoppenreijs et al. (1996), "Corneal endothelium and growth factors." Surv. Ophthalmol. 41: 155-64.
Hsu et al. (1999), "Heparin is Essential for a Single Keratinoctye Growth Factor Molecule to Bind and Form a Complex with Two Molecules of the Extracellular Domain of its Receptor," Biochemistry 38:2523-34.
Hu et al., (1998), "FGF-18, a novel member of the fibroblast growth factor family, stimulates hepatic and intestinal proliferation," Mol. Cell. Biol. 18(10):6063-6074.
Hull et al (1997), "Healing with basic fibroblast growth factors is associated with reduced indomethacin induced relapse in a human model of gastric ulceration," Gut 40: 204-10.
Ishibashi et al., 2005, "Is arginine a protein-denaturant!" Protein Expr. Purif. 42: 1-6.
Itoh and Ornitz (2004), "Evolution of the FGF and FGFR gene families," Trends in Genetics 20(11): 563-569.
Jakobovits et al., 1993, "Analysis of homozygous mutant chimeric mice: deletion of the immunoglobulin heavy-chain joining region blocks B-cell development and antibody production" Proc. Natl. Acad. Sci. U.S.A. 90: 2551-55.
Jakobovits et al., 1993, "Germ-line transmission and expression of a human-derived yeast artificial chromosome" Nature 362: 255-58.
Jones et al., 1986, "Replacing the complementarity-determining regions in a human antibody with those from a mouse" Nature 321: 522-25.
Kaufman et al. (1999), "Transgenic analysis of a 100-kb human beta-globin cluster-containing DNA fragment propagated as a bacterial artificial chromosome," Blood 94: 3178-3184.
Kennell (1971), "Principles and practices of nucleic acid hybridization," Progr. Nucl. Acid Res. Mol. Biol. 11: 259-301.
Kharitonenkov et al. (2005), "FGF-21 as a novel metabolic regulator," J. Clin. Invest. 115: 1627-1635.
Kharitonenkov et al, (2006), "The metabolic state of diabetic monkeys is regulated by FGF-21" Endocrinology DOI:10.1210/en.2006-1168.
Kharitonenkov et al. (2008), "Fibroblast Growth Factor-21 as a Therapeutic Agent for Metabolic Diseases" Biodrugs 22 1: 37-44.
Kornmann et al. (1998), "Role of fibroblast growth factors and their receptors in pancreatic cancer and chronic pancreatitis," Pancreas 17: 169-75.
Xu, Jing et al. (2009) "Acute glucose-lowering and insulin-sensitizing action of FGF21 in insulin-resistant mouse models-association with liver and adipose tissue effects." Am. J. Physiol. Endocrinol. Metab. 297: E1105-E1114.
Xu et al., (2009) "Fibroblast Growth Factor 21 Reverses Hepatic Steatosis, increases Energy Expenditure, and Improves Insulin Sensitivity in Diet-Induced Obese Mice" Diabetes 58(1):250-9.

Yamaoka and Itakura (1999), "Development of pancreatic islets (review)," Int. J. Mol. Med. 3: 247-61.
Yie et al., (2009), "FGF21 N- and C-termini play different roles in receptor interaction and activation" FEBS Lett. 583:19-24.
Laemmli (1970), "Cleavage of structural proteins during the assembly of the head of bacteriophage T4" Nature 227: 680-85.
Ledley (1996), "Pharmaceutical Approach to Somatic Gene Therapy," Pharm. Res. 13(11): 1595-1614.
Lewis et al. (1997), "Angiogenesis by gene therapy: a new horizon for myocardial revascularization?" Cardiovasc. Res. 135: 490-497.
Li, Xiaofan, et al. (2009) "Inhibition of lipolysis may contribute to the acute regulation of plasma FFA and glucose by FGF21 in ob/ob mice," FEBS Letters 583: 323-03234.
Liu et al. (2007), "FGF18 is required for early chondrocyte proliferation, hypertrophy and vascular invasion of the growth plate," Dev. Biol. 302: 80-91.
Mahairas et al. (1999), "Sequence-tagged connectors: a sequence approach to mapping and scanning the human genome," PNAS 96(17): 9739-9744.
Mannall et al., 2007, "Factors affecting protein refolding yields in a fed-batch and batch-refolding system" Biotechnol. Bioeng. 97: 1523-34.
Marks et al., 1991, "By-passing immunization. Human antibodies from V-gene libraries displayed on phage" J. Mol. Biol. 222: 581-597.
Mikkelsen (1993), "Interpreting sequence motifs: a cautionary note," Trends Genet. 9(5): 15.
Mohammadi, et al. (2005), "Structural basis for fibroblast growth factor receptor activation" Cytokine & Growth Factor Reviews 16: 107-137.
Morrison et al., 1985, "Chimeric human antibody molecules: mouse antigen-binding domains with human constant region domains" Proc. Natl. Acad. Sci. U.S.A. 81: 6851-55.
Moyers et al. (2007), "Molecular Determinants of FGF-21 Activity-Synergy and Cross-Talk with PPARγ Signaling" J. Cell. Phys. 210: 1-6.
Nakamura et al, (1995), "The murine lymphotoxin-beta receptor cDNA: isolation by the signal sequence trap and chromosomal mapping," Genomics 30(2): 312-19.
Ngo et al. (1994), "Computational complexity, protein structure prediction, and the Levinthal paradox," in The Protein Folding Problem and Tertiary Structure Prediction, Merz & Le Grand ed., Birkhauser: Boston, pp. 491-495.
Nishimura et al. (2000), "Identification of a novel FGF, FGF-21, preferentially expressed in the liver(l)," Biochim Biophys Acta 21: 203-6.
Niyogi (1969), "The influence of chain length and base composition on the specific association of oligoribonucleotides with denatured deoxyribonucleic acid," J. Biol. Chem. 244(6):1576-81.
Ogawa, Y., et al. (2005) "Klotho is required for metabolic activity of fibroblast growth factor 21," Proc. Natl. Acad. Sci. USA 104:7432-7437.
Ogawa et al. (2007), "Beta-klotho is required for metabolic activity of fibroblast growth factor 21." PNAS 104(18) 7432-7437.
Parthiban et al. (2007), "Computational modeling of protein mutant stability: analysis and optimization of statistical potentials and structural features reveal insights into prediction model development," BMC Struct. Biol. 7:54.
Parthiban et al., 2006, "MSH2 is essential for the preservation of genome integrity and pevents homeologous recombination in the moss Physcomitrella patens" Nucleic Acids Res. 34: 232-42.
Peus and Pittelkow (1996), "Growth factors in hair organ development and the hair growth cycle," Dermatol. Clin. 14:559-72.
Phillips (2001), "The challenge of gene therapy and DNA delivery," J. Pharm. Pharmacology 53: 1169-1174.
Plotnikov et al. (1999), "Structural Basis for FGF Receptor Dimerization and Activation" Cell 98: 641-650.
Plotnikov et al, (2000), "Crystal Structures of Two FGF-FGFR Complexes Reveal the Determinants of Ligand-Receptor Specificity," Cell 101: 413-24.
Podolsky (1997), "Healing the epithelium: solving the problem from two sides," J. Gastroenterol. 32: 122-6.

Polejaeva et al. (2000), "New advances in somatic cell nuclear transfer: application in transgenesis," Theriogenology 53(1): 117-26.

R&D Systems, Catalog No. MAB3738, Lot No. XRU02 (2007), "Monoclonal anti-human/mouse Klotho Beta antibody," XP-002624719.

Ratajczak (1997), "Fibroblast growth factors and early hemopoietic cell development," Leuk. Lymphoma 27: 221-9.

Riechmann et al., 1998, "Reshaping human antibodies for therapy" Nature 332: 323-27.

Rudolph et al., 1997, "Folding proteins," Protein Function: A Practical Approach (Creighton, ed., New York, IRL Press) 57-99.

Rulicke et al. (2000), "Germ line transformation of mammals by pronuclear microinjection." Exp. Physiol. 85(6): 589-601.

Skolnick et al, (2000), "From genes to protein structure and function: novel applications of computational approaches in the genomic era," Trends Biotechnol. 18(1): 34-39.

Smallwood et al. (1996), "Fibroblast Growth Factor (FGF) homologous factors: new members of the FGF family implicated in nervous system development", PNAS 93: 9850-9857.

Smith et al. (1997), "The challenges of genome sequence annotation or 'the devil is in the details,'" Nat. Biotechnol. 15(12): 1222-23.

Suzuki, Masashi et al. (2008) "Beta-klotho is required for fiboblast growth factor (FGF) 21 signaling through FGF receptor (FGFR) 1c and FGFRc," Mol. Endocr. 22(4):1006-1014.

Trouiller, et al. (2006), "MSH2 is essential for the preservation of genome integrity and prevents homeologous recombination in the moss *Physcomitrella patens*" Nucleic Acids Research vol. 34, (1): 232-242.

Verhoeyen et al., 1988, "Reshaping human antibodies: gralting an antilysozyme activity" Science 239: 1534-36.

Verma et al. (1997), "Gene therapy—promise,problems and prospects," Nature 389: 239-242.

Wang et al. (1999), "Rapid analysis of gene expression (RAGE) facilitates universal expression profiling," Nuc. Acids Res. 27: 4609-4618.

Webster (1997), "Growth factors and myelin regeneration in multiple sclerosis," Mult. Scler. 3:113-20.

Wente et al. (2006), "Fibroblast Growth Factor-21 Improves Pancreatic B-Cell Function and Survival by Activation of Extracellular Signal-Regulated Kinase ½ and Akt Signaling Pathways" Diabetes 55: 2470-2478.

Wu, X. and Li, Y. (2011) Understanding the structure-function relationship between FGF19 and its motogenic and metabolic activities. In Endocrine FGFs and Klothos, edited by Makoto Kuro-o, Landes Bioscience and Springer Science Media.

Wu, Xinle et al. (2007) "Co-receptor requirements for fibroblast growth factor-19 signaling," J. Biol. Chem. 282 (40): 29069-29072.

Wu et al. (2010), "FGF19 induced hepatocyte proliferation is mediated through FGFR4 activiation," J. Biol. Chem. 285:5165.

Wu, X., et al. (2009) "Role FGF19 induced FGFR4 activation in the regulation of glucose homeostatis." Aging 1:1023.

Wu, Xinle et al. (2009) "Selective activation of FGFR4 by an FGF19 variant does not improve glucose metabolism in ob/ob mice,"PNAS 106 (34): 14379-14384.

Wu, Xinle et al. (2010) "Separating mitogenic and metabolic activities of fibroblast growth factor 19 (FGF19)," PNAS 107 (32): 14158-14163.

Fukumoto, Seji, "Actions and mode of actions of FGF19 subfamily members," Endocr. J. 55:23-31 (2008).

Fukumoto, S. & Yamashita, T., "FGF23 is a hormone-regulating phosphate metabolism-Unique biological characteristics of FGF23," Bone 40:1190-1195 (2007).

Ogawa, Y. et al., "Klotho is required for metabolic activity of fibroblast growth factor 21," Proc. Natl. Acad. Sci. U.S.A. 104:7432-7437 (2007).

Inagaki, T. et al., "Fibroblast growth factor 15 functions as an enterohepatic signal to regulate bile acid homeostasis," Cell. Metab. 2:217-225 (2005).

Tomlinson E., et al., "Transgenic mice expressing human fibroblast growth factor-19 display increased metabolic rate and decreased adiposity," Endocrinology 143:1741-1747 (2002).

Fu, Ling et al., "Fibroblast growth factor 19 increases metabolic rate and reverses dietary and leptin-deficient diabetes," Endocrinology 145:2594-2503 (2004).

Xu, Jing et al., "Fibroblast Growth Factor 21 Reverses Hepatic Steatosis, Increases Energy Expenditure, and Improves Insulin Sensitivity in Diet-Induced Obese Mice," Diabetes 58:250-59 (2008).

Kharitonenkov, Alexei et al., "The Metabolic State of Diabetic Monkeys is Regulated by Fibroblast Growth Factor-21," Endocrinology 148:774-781 (2007).

Kurosu,, Hiroshi & Kuro-o, Makoto, "The Klotho gene family and the endocrine fibroblast growth factors," Curr. Opin. Nephrol. Hypertens. 17:368-372 (2008).

Wu Xinle, et al., "C-terminal Tail of FGF19 Determines Its Specificity toward Klotho Co-receptors," J. Biol. Chem. 283 (48):33304-9 (2008).

Nicholes, Katrina et al., "A mouse model of hepatocellular carcinoma: ectopic expression of fibroblast growth factor 19 in skeletal muscle of transgenic mice," Am. J. Pathol. 160:2295-2307 (2002).

Fausto, N., "Mouse liver tumorigenesis: models, mechanisms, and relevance to human disease," Seminars in Liver Disease 19:243-252 (1999).

Kurosu,, Hiroshi & Kuro-o, Makoto, "The Klotho gene family as a regulator of endocrine fibroblast growth factors," Mol. Celi. Endocrinol. 299:72-78 (2009).

Kurosu, Hiroshi et al., "Tissue-specific Expression of Klotho and Fibroblast Growth Factor (FGF) Receptor Isoforms Determines Metabolic Activity of FGF19 and FGF21," J. Biol. Chem. 282:26687-26695 (2007).

Ho, Han Kiat, et al., "Fibroblast growth factor receptor 4 regulates proliferation, anti-apoptosis and alpha-fetoprotein secretion during hepatocellular carcinoma progression and represents a potential target for therapeutic intervention," Hepatol. 50:118-127 (2009).

Capon, Daniel J., et al., "Designing CD4 immunoadhesins for AIDS therapy," Nature 337: 525-31 (1989).

Francis, Gillian E., "Protein modification and fusion proteins," Focus on Growth Factors 3: 4-10 (1992).

Wischke, C. & Schwendeman, S.P., "Principles of encapsulating hydrophobic drugs in PLA/PLGA microparticles," Int. J. Pharm. 364:298-327 (2008).

Freiberg, S. & Zhu, X., "Polymer microspheres for controlled drug release," Int. J. Pharm. 282:1-18 (2004).

Sidman, Kenneth R. et al., "Controlled Release of Macromolecules and Pharmaceuticals from Synthetic Polypeptides Based on Glutamic Acid," Biopolymers 22: 547-56 (1983).

Langer, Robert et al., "Biocompatibility of polymeric delivery systems for micromolecules," J. Biomed. Mater. Res. 15: 167-277 (1981).

Langer, Robert, "Controlled release of macromolecules," Chem. Tech. 12: 98-105 (1982).

Eppstein, Deborah A. et al., "Biological activity of liposome-encapsulated murine interferon gamma is mediated by a cell membrane receptor," Proc. Natl. Acad. Sci. U.S.A. 82: 3688-92 (1985).

Kohler et al. "Continuous cultures of fused cells secreting antibody of predefined specificity," Nature 256: 495-97 (1975).

Kozbor, Danuta, et al., "A human hybrid myeloma for production of human monoclonal antibodies" J. Immunol. 133: 3001 (1984).

Brodeur et al., Monoclonal Antibody Production Techniques and Applications 51-63 (Marcel Dekker, Inc., 1987).

Bayer, Edward A. and Wilchek, Meir, "Protein Biotinylation," Meth. Enz. 184: 138-63 (1990).

Lin, Benjamin C., et al., "Liver-specific Activities of FGF19 Require Klotho beta," J. Bio. Chem. 282, 27277-27284 (2007).

Goetz et al., "BBA—Molecular and Cell Biology of Lipids," Mol. Cell. Biol. 27:3417-28 (2007).

Schlessinger, J. et al., "Crystal Structure of a Ternary FGF-FGFR-Heparin Complex Reveals a Dual Role for Heparin in FGFR Binding and Dimerization," Mol. Cell 6:743-50 (2000).

Harmer, Nicholas J., et al., "The crystal structure of fibroblast growth factor (FGF) 19 reveals novel features of the FGF family and offers a structural basis for its unusual receptor affinity," Biochem 43(3): 629-640 (2004).

Database UniProt Q9DDN0, Accession No. 09DDN0, "Fibroblast growth factor 19," XP002596987 (2001).

Database UniProt Q76B59, Accession No. Q76B59, "Fibroblast growth factor 19," XP002596988 (2004).

Database UniProt B7U4G3, Accession No. B7U4G3, "FGF19," XP002596989 (2009).

Database UniProt B3DHS4, Accession No. B3DHS4, "FGF19 protein," XP002596990 (2008).

* cited by examiner

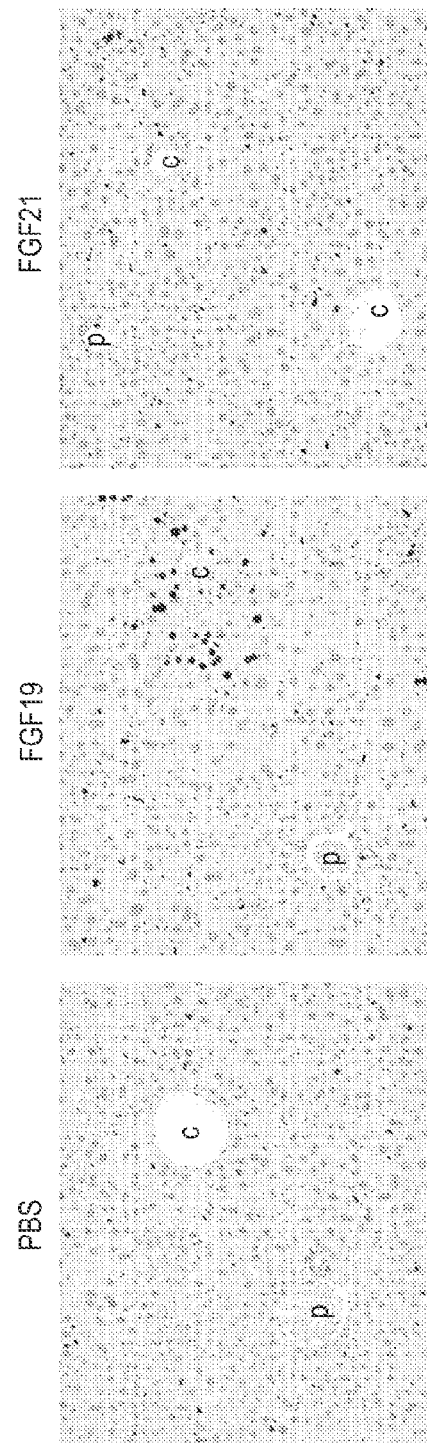
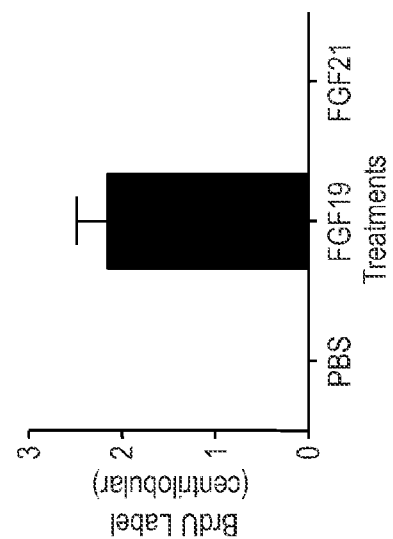
FIG. 1A
FIG. 1B

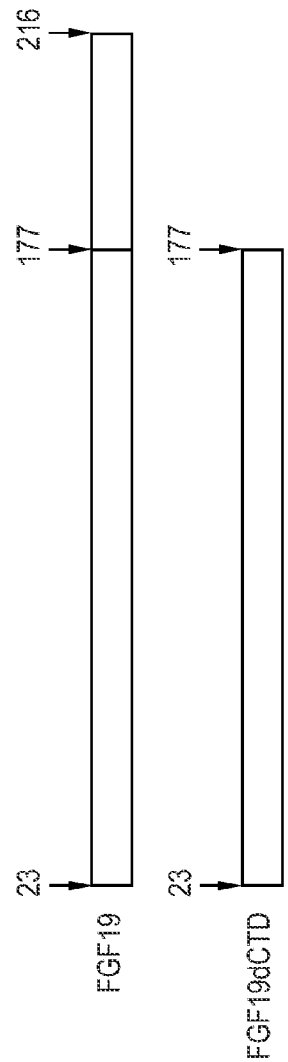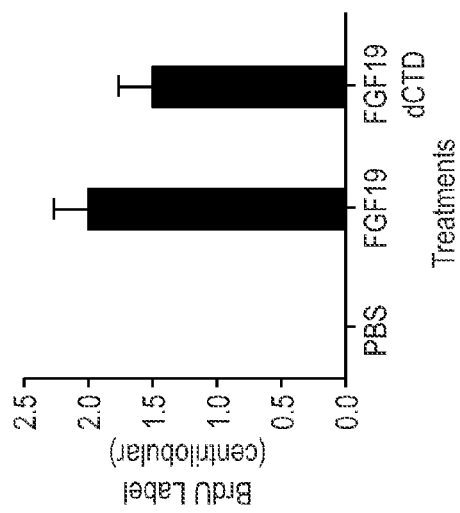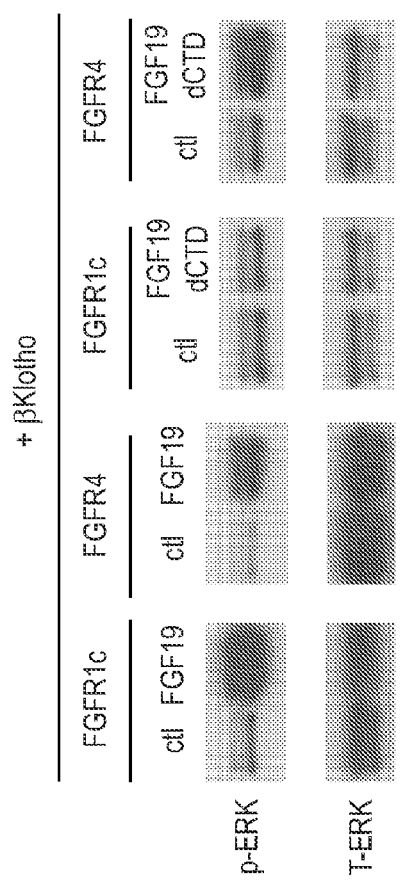

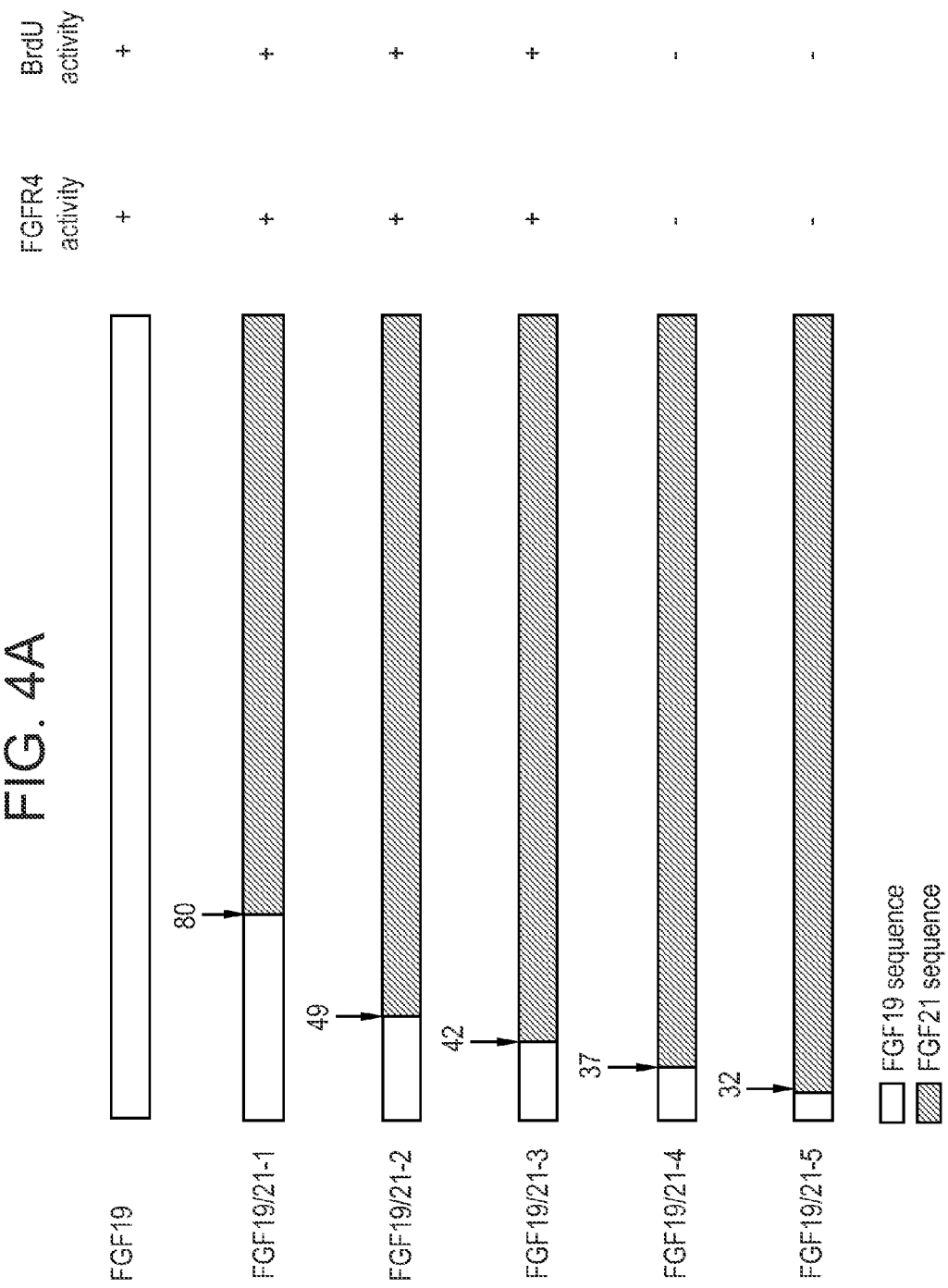

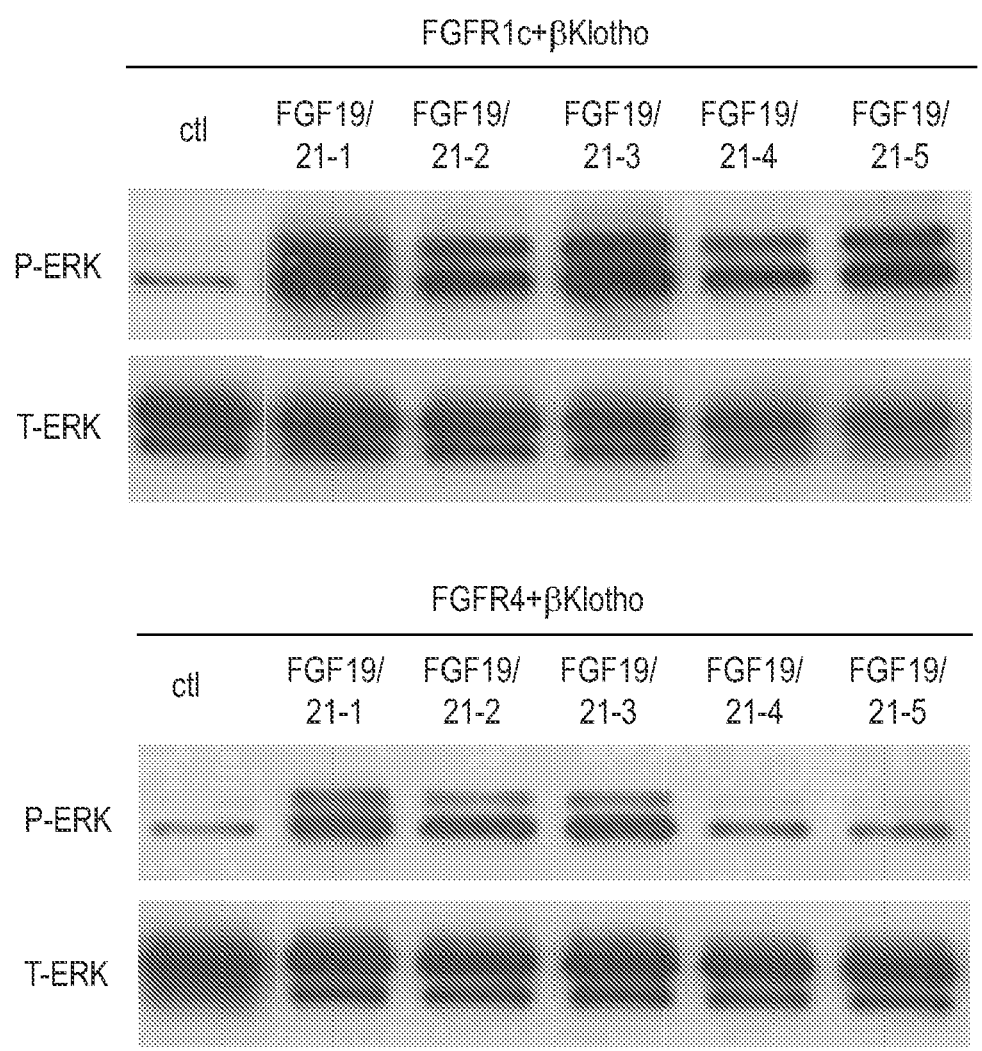

- ● FGF21
- ■ FGF19
- ○ FGF19/21-1
- □ FGF19/21-2
- △ FGF19/21-3
- ▲ FGF19/21-4
- ▼ FGF19/21-5

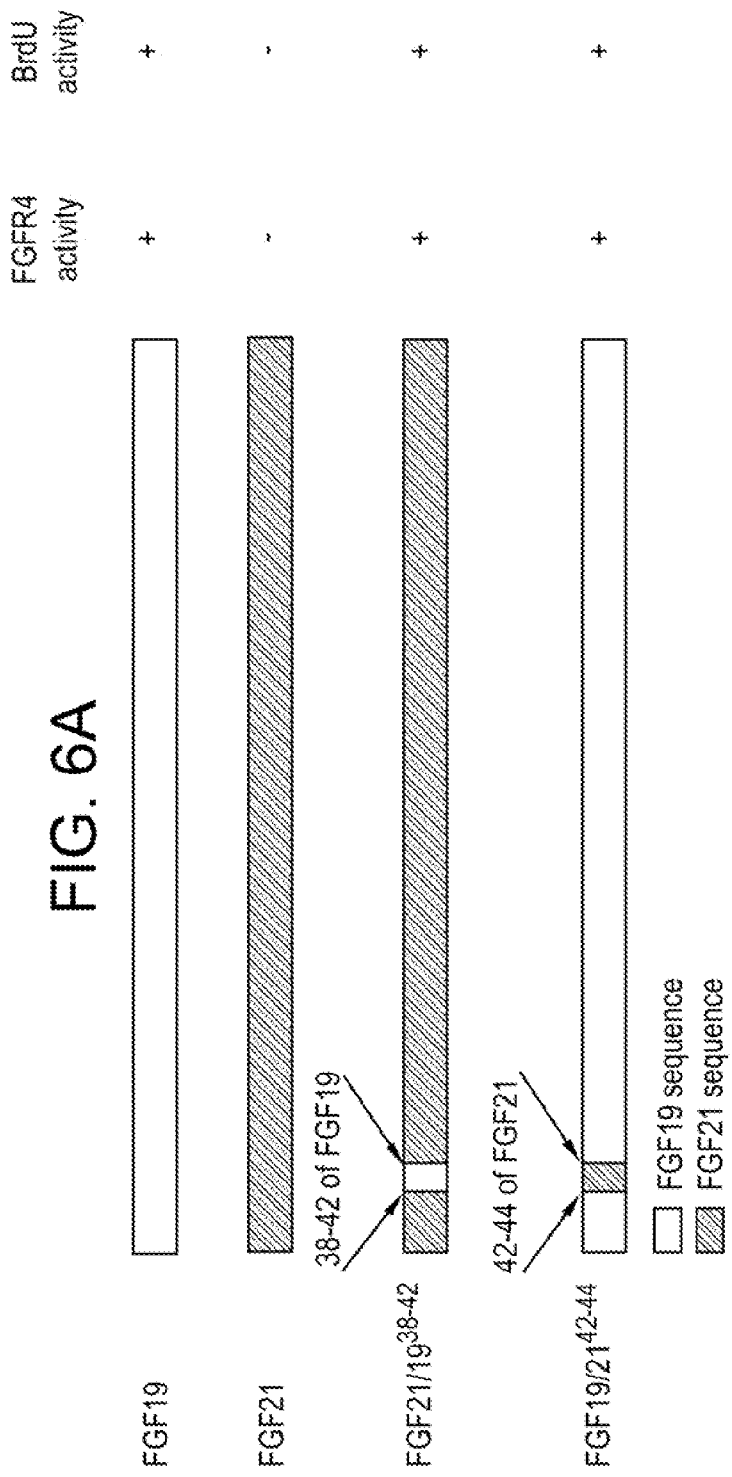

FIG. 7

β1- β2 loop

| FGF19 | 47 | LYTSGPHGLSSCFL 60 | SEQ ID:51 |
| | | SEQ ID:52 | |
| FGF21 | 49 | LYTDDAQ-QTEAHL 61 | SEQ ID:53 |
| | | SEQ ID:54 | |
| FGF23 | 42 | LYTATAR--NSYHL 53 | SEQ ID:55 |
| | | SEQ ID:56 | |

β 10- β 12 segment

| FGF19 | 141 | LPVSLSSAKQ RQLYKNRGFL PLSHFLPM 168 | SEQ ID:59 |
| | | SEQ ID:58 | |
| FGF21 | 142 | LPLHLPGN-- KSPHRDPAPR GPARFLPL 167 | SEQ ID:57 |
| | | SEQ ID:60 | |
| FGF23 | 134 | FLVSLGRAK- RAFLPGMNPP PYSQFLSR 160 | SEQ ID:61 |
| | | SEQ ID:62 | |

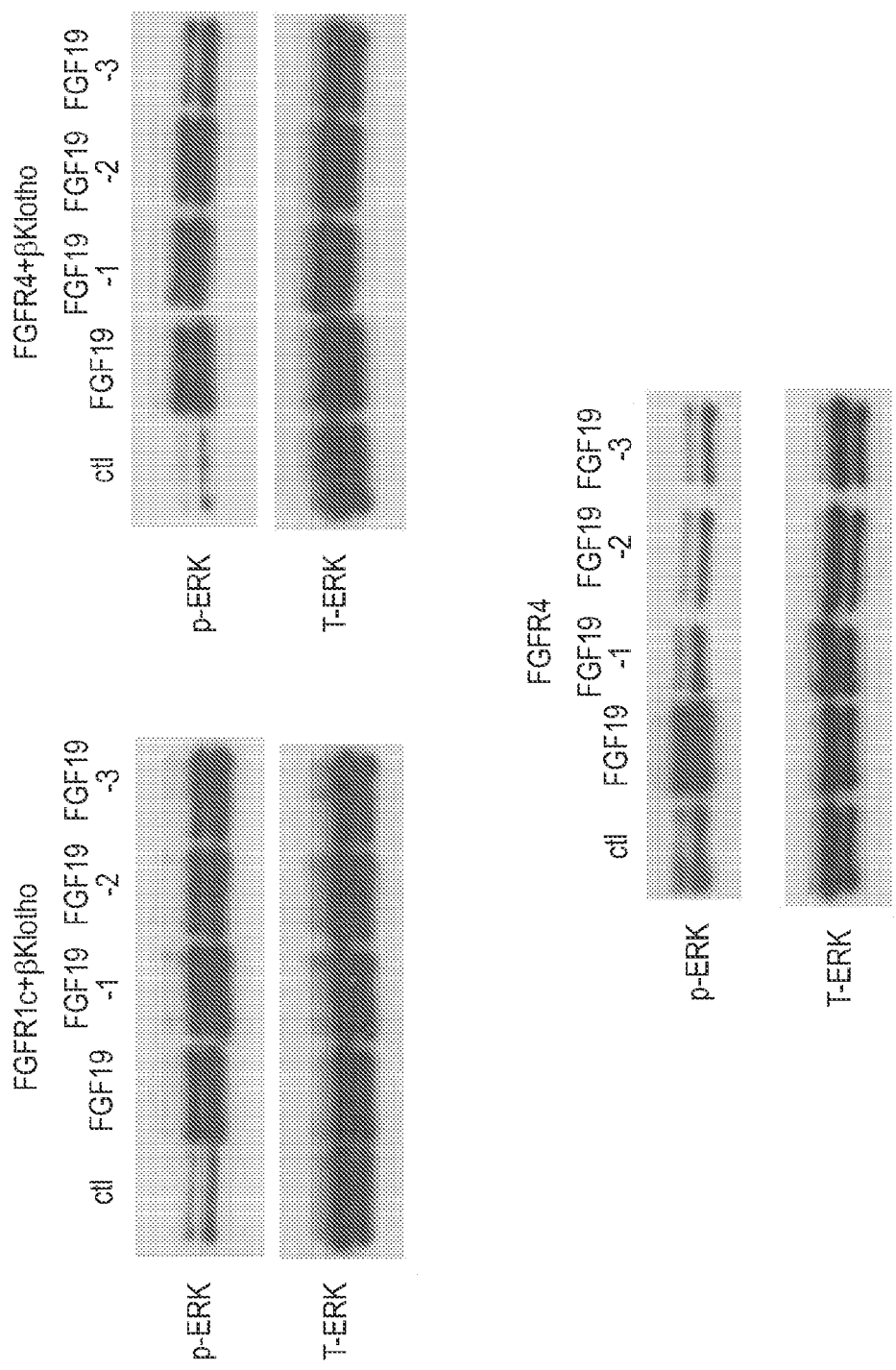

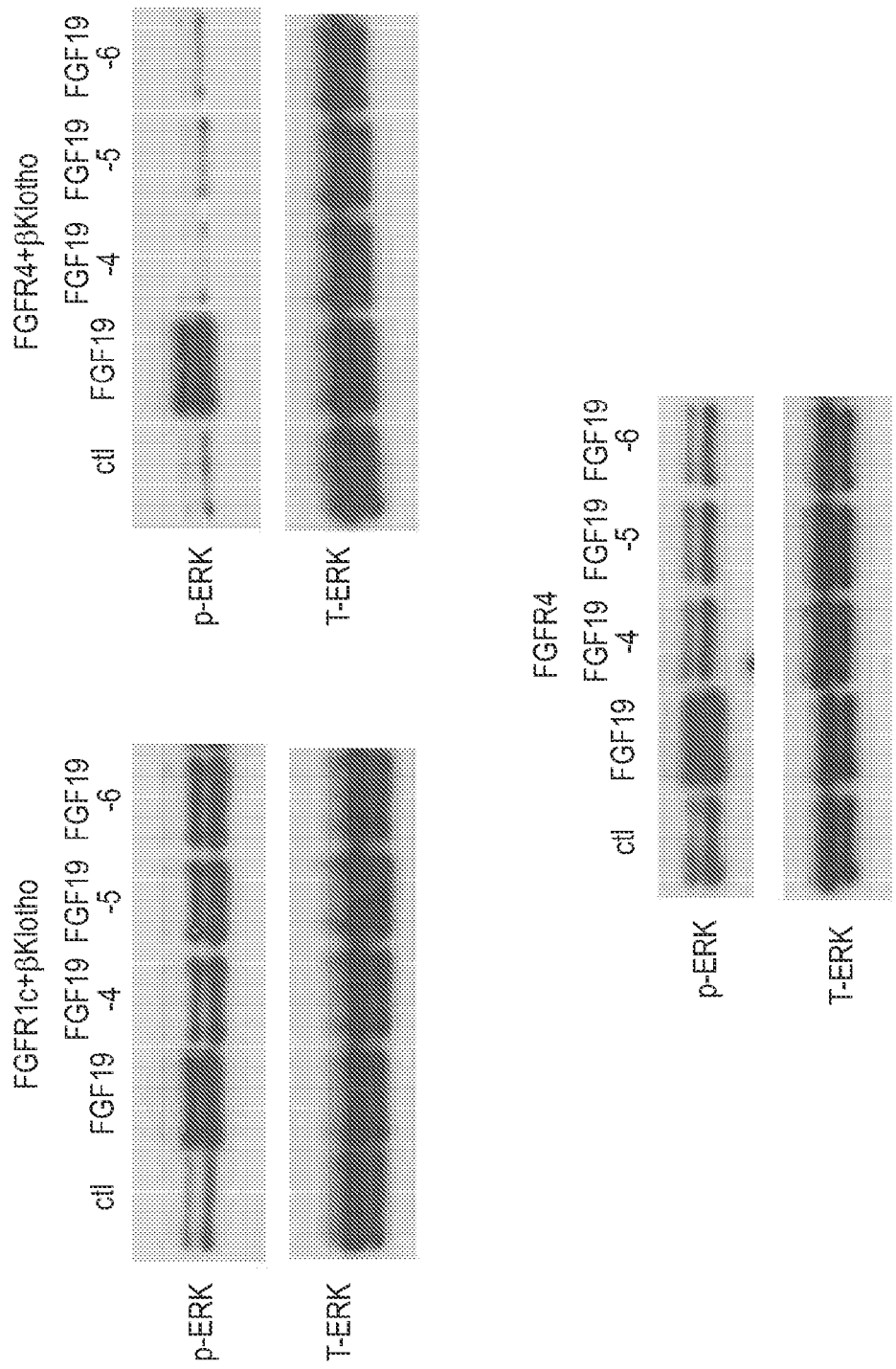

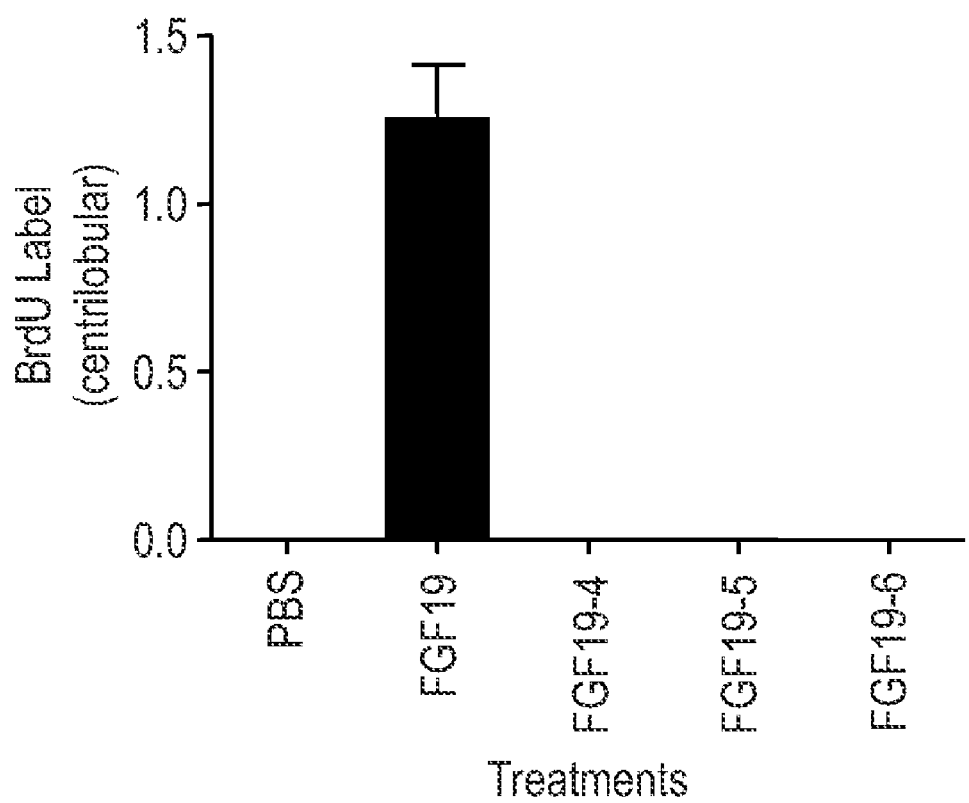

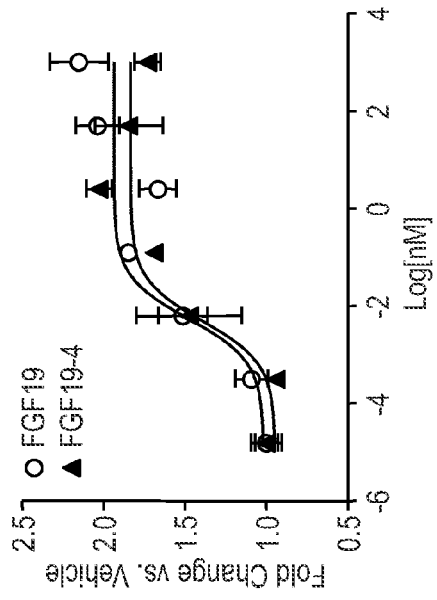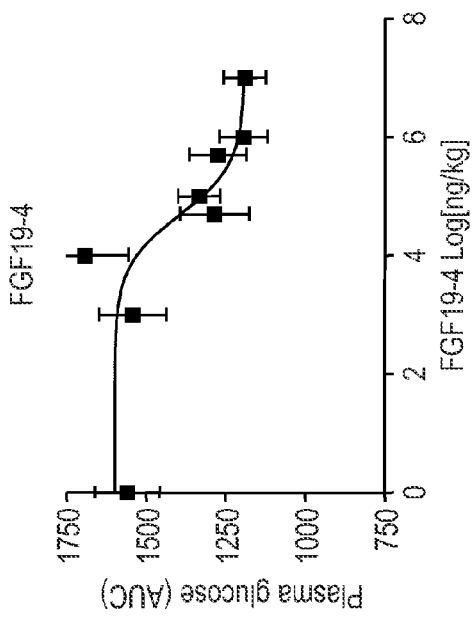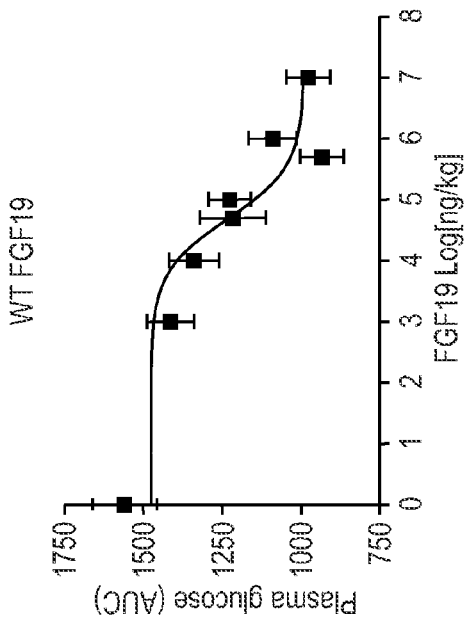
FIG. 10A
FIG. 10B-1
FIG. 10B-2

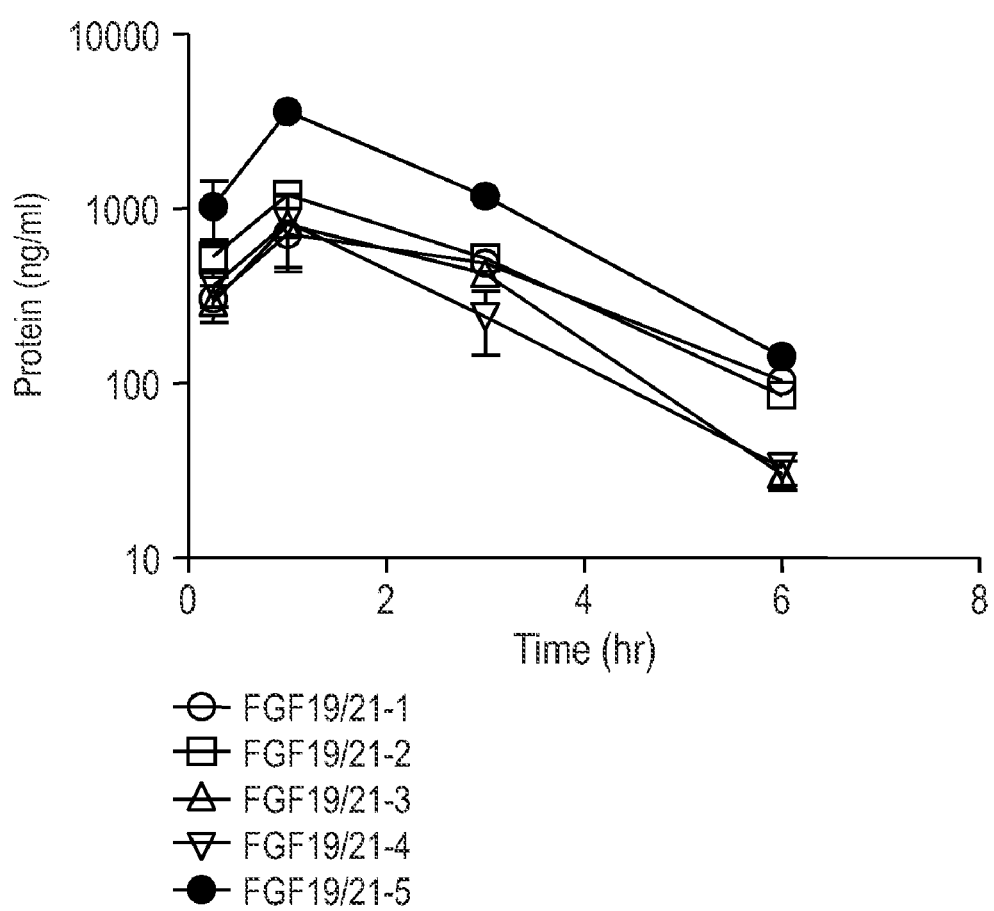

| | SEQ ID# | | FGFR1c | FGFR4 |
|---|---|---|---|---|
| FGF19 | 49 | WGDPI | + | + |
| FGF19-4 | | -GQ-V | + | - |
| FGF19-mut22 | 71 | -GD-I | - | +/- |
| FGF19-mut23 | 72 | WG-PI | + | + |
| FGF19-mut24 | 73 | WGDPV | - | + |
| FGF19-mut25 | 84 | WGD-I | - | - |
| FGF19-mut26 | | -GDPI | - | - |
| FGF19-mut27 | | -G-PI | - | - |
| FGF19-mut28 | 74 | WGQPI | + | + |
| FGF19-mut29 | 75 | WGAPI | + | + |
| FGF19-mut30 | 76 | AGDPI | - | - |
| FGF19-mut31 | 77 | WADPI | + | + |
| FGF19-mut32 | 78 | WGDAI | + | + |
| FGF19-mut33 | 79 | WGDPA | + | + |
| FGF19-mut34 | 80 | W-DPI | +/- | +/- |
| FGF19-mut35 | 81 | WGD-I | - | - |
| FGF19-mut36 | 82 | WGDP- | - | - |
| FGF19-mut37 | 83 | FGDPI | - | - |

Figure 12

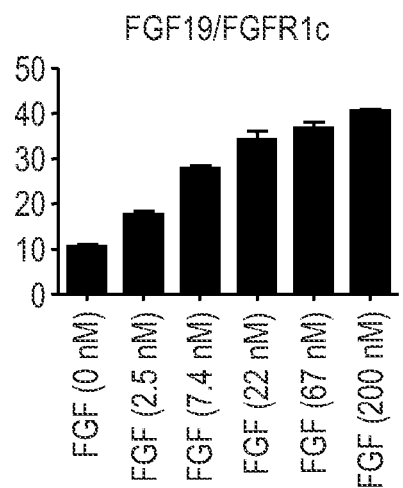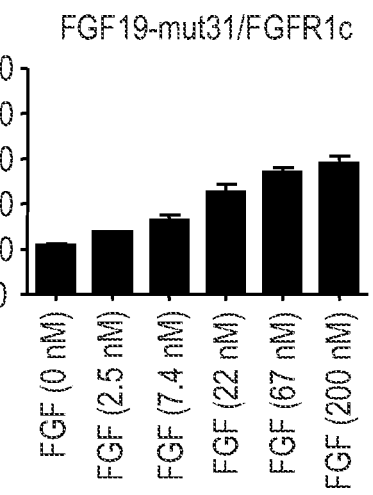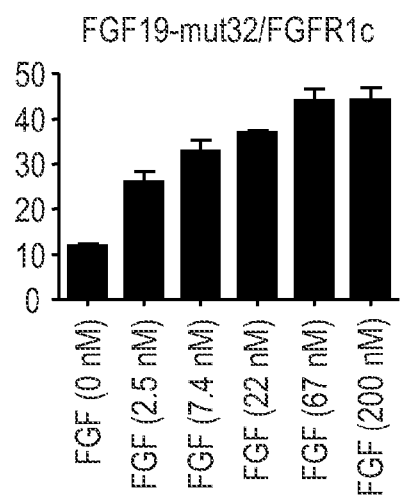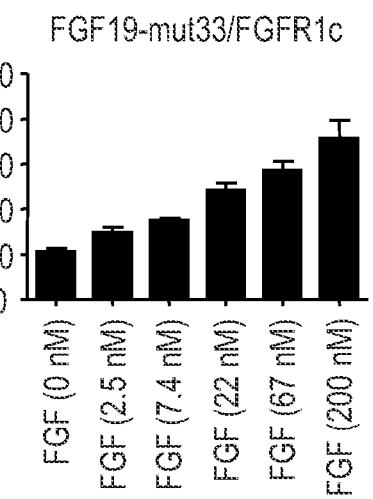

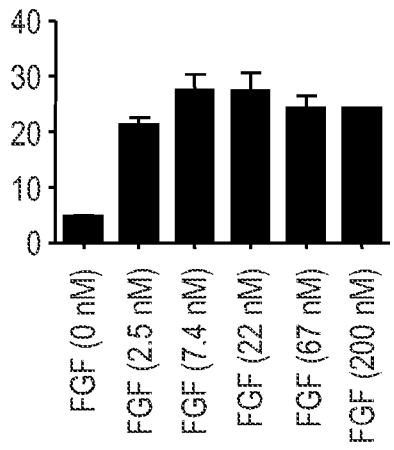
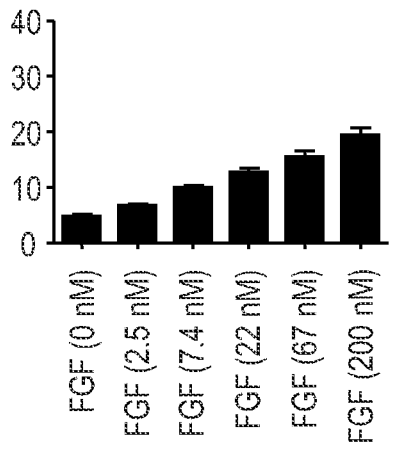
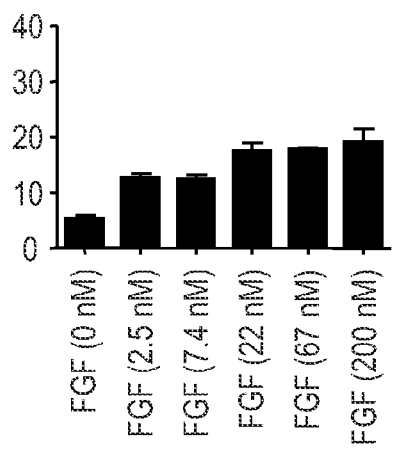
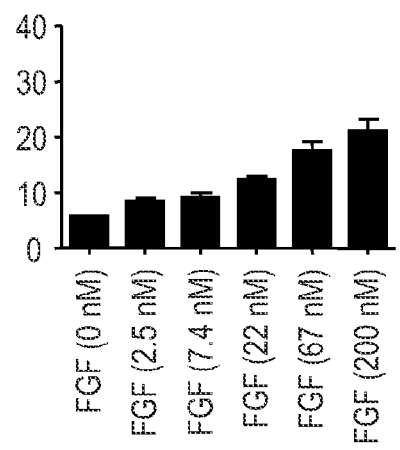

FGF19-mut34/FGFR4

FGF19-mut35/FGFR4

FGF19-mut36/FGFR4

FGF19-mut37/FGFR4

SEQUENCE LISTING

<160> NUMBER OF SEQ ID NOS: 84

<210> SEQ ID NO 1
<211> LENGTH: 651
<212> TYPE: DNA
<213> ORGANISM: Homo sapiens
<220> FEATURE:
<221> NAME/KEY: CDS
<222> LOCATION: (1)..(651)

<400> SEQUENCE: 1

```
atg cgg agc ggg tgt gtg gtg gtc cac gta tgg atc ctg gcc ggc ctc      48
Met Arg Ser Gly Cys Val Val Val His Val Trp Ile Leu Ala Gly Leu
1               5                   10                  15 tgg ctg gcc gtg gcc ggg cgt cca ctt gct ttt tct gat gct ggt cca      96
Trp Leu Ala Val Ala Gly Arg Pro Leu Ala Phe Ser Asp Ala Gly Pro
            20                  25                  30 cac gtt cac tac ggc tgg ggc gac ccc atc cgc ctg cgg cac ctg tac     144
His Val His Tyr Gly Trp Gly Asp Pro Ile Arg Leu Arg His Leu Tyr
        35                  40                  45 acc tcc ggc ccc cac ggg ctc tcc agc tgc ttc ctg cgc atc cgt gcc     192
Thr Ser Gly Pro His Gly Leu Ser Ser Cys Phe Leu Arg Ile Arg Ala
    50                  55                  60 gac ggc gtc gtg gac tgc gcg cgg ggc cag agc gcg cac agt ttg ctg     240
Asp Gly Val Val Asp Cys Ala Arg Gly Gln Ser Ala His Ser Leu Leu
65                  70                  75                  80 gag atc aag gca gtc gct ctg cgg acc gtg gcc atc aag ggc gtg cac     288
Glu Ile Lys Ala Val Ala Leu Arg Thr Val Ala Ile Lys Gly Val His
                85                  90                  95 agc gtg cgg tac ctc tgc atg ggc gcc gac ggc aag atg cag ggg ctg     336
Ser Val Arg Tyr Leu Cys Met Gly Ala Asp Gly Lys Met Gln Gly Leu
            100                 105                 110 ctt cag tac tcg gag gaa gac tgt gct ttc gag gag gag atc cgc cca     384
Leu Gln Tyr Ser Glu Glu Asp Cys Ala Phe Glu Glu Glu Ile Arg Pro
        115                 120                 125 gat ggc tac aat gtg tac cga tcc gag aag cac cgc ctc ccg gtc tcc     432
Asp Gly Tyr Asn Val Tyr Arg Ser Glu Lys His Arg Leu Pro Val Ser
    130                 135                 140 ctg agc agt gcc aaa cag cgg cag ctg tac aag aac aga ggc ttt ctt     480
Leu Ser Ser Ala Lys Gln Arg Gln Leu Tyr Lys Asn Arg Gly Phe Leu
145                 150                 155                 160 cca ctc tct cat ttc ctg ccc atg ctg ccc atg gtc cca gag gag cct     528
Pro Leu Ser His Phe Leu Pro Met Leu Pro Met Val Pro Glu Glu Pro
                165                 170                 175 gag gac ctc agg ggc cac ttg gaa tct gac atg ttc tct tcg ccc ctg     576
Glu Asp Leu Arg Gly His Leu Glu Ser Asp Met Phe Ser Ser Pro Leu
            180                 185                 190 gag acc gac agc atg gac cca ttt ggg ctt gtc acc gga ctg gag gcc     624
Glu Thr Asp Ser Met Asp Pro Phe Gly Leu Val Thr Gly Leu Glu Ala
```

```
                195                 200                 205
gtg agg agt ccc agc ttt gag aag taa                                              651
Val Arg Ser Pro Ser Phe Glu Lys
    210                 215

<210> SEQ ID NO 2
<211> LENGTH: 216
<212> TYPE: PRT
<213> ORGANISM: Homo sapiens

<400> SEQUENCE: 2

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 3
<211> LENGTH: 585
<212> TYPE: DNA
<213> ORGANISM: Homo sapiens
<220> FEATURE:
<221> NAME/KEY: CDS
<222> LOCATION: (1)..(585)

<400> SEQUENCE: 3 cgt cca ctt gct ttt tct gat gct ggt cca cac gtt cac tac ggc tgg           48
Arg Pro Leu Ala Phe Ser Asp Ala Gly Pro His Val His Tyr Gly Trp
1               5                   10                  15 ggc gac ccc atc cgc ctg cgg cac ctg tac acc tcc ggc ccc cac ggg           96
Gly Asp Pro Ile Arg Leu Arg His Leu Tyr Thr Ser Gly Pro His Gly
                20                  25                  30 ctc tcc agc tgc ttc ctg cgc atc cgt gcc gac ggc gtc gtg gac tgc          144
Leu Ser Ser Cys Phe Leu Arg Ile Arg Ala Asp Gly Val Val Asp Cys
            35                  40                  45 gcg cgg ggc cag agc gcg cac agt ttg ctg gag atc aag gca gtc gct          192
```

```
Ala Arg Gly Gln Ser Ala His Ser Leu Leu Glu Ile Lys Ala Val Ala
    50                  55                  60 ctg cgg acc gtg gcc atc aag ggc gtg cac agc gtg cgg tac ctc tgc        240
Leu Arg Thr Val Ala Ile Lys Gly Val His Ser Val Arg Tyr Leu Cys
65                  70                  75                  80 atg ggc gcc gac ggc aag atg cag ggg ctg ctt cag tac tcg gag gaa        288
Met Gly Ala Asp Gly Lys Met Gln Gly Leu Leu Gln Tyr Ser Glu Glu
                85                  90                  95 gac tgt gct ttc gag gag gag atc cgc cca gat ggc tac aat gtg tac        336
Asp Cys Ala Phe Glu Glu Glu Ile Arg Pro Asp Gly Tyr Asn Val Tyr
            100                 105                 110 cga tcc gag aag cac cgc ctc ccg gtc tcc ctg agc agt gcc aaa cag        384
Arg Ser Glu Lys His Arg Leu Pro Val Ser Leu Ser Ser Ala Lys Gln
        115                 120                 125 cgg cag ctg tac aag aac aga ggc ttt ctt cca ctc tct cat ttc ctg        432
Arg Gln Leu Tyr Lys Asn Arg Gly Phe Leu Pro Leu Ser His Phe Leu
    130                 135                 140 ccc atg ctg ccc atg gtc cca gag gag cct gag gac ctc agg ggc cac        480
Pro Met Leu Pro Met Val Pro Glu Glu Pro Glu Asp Leu Arg Gly His
145                 150                 155                 160 ttg gaa tct gac atg ttc tct tcg ccc ctg gag acc gac agc atg gac        528
Leu Glu Ser Asp Met Phe Ser Ser Pro Leu Glu Thr Asp Ser Met Asp
                165                 170                 175 cca ttt ggg ctt gtc acc gga ctg gag gcc gtg agg agt ccc agc ttt        576
Pro Phe Gly Leu Val Thr Gly Leu Glu Ala Val Arg Ser Pro Ser Phe
            180                 185                 190 gag aag taa                                                             585
Glu Lys <210> SEQ ID NO 4
<211> LENGTH: 194
<212> TYPE: PRT
<213> ORGANISM: Homo sapiens

<400> SEQUENCE: 4

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
```

Glu Lys

<210> SEQ ID NO 5
<211> LENGTH: 588
<212> TYPE: DNA
<213> ORGANISM: Homo sapiens
<220> FEATURE:
<221> NAME/KEY: CDS
<222> LOCATION: (1)..(588)

<400> SEQUENCE: 5

```
atg cgt cca ctt gct ttt tct gat gct ggt cca cac gtt cac tac ggc      48
Met Arg Pro Leu Ala Phe Ser Asp Ala Gly Pro His Val His Tyr Gly
1               5                   10                  15 tgg ggc gac ccc atc cgc ctg cgg cac ctg tac acc tcc ggc ccc cac      96
Trp Gly Asp Pro Ile Arg Leu Arg His Leu Tyr Thr Ser Gly Pro His
            20                  25                  30 ggg ctc tcc agc tgc ttc ctg cgc atc cgt gcc gac ggc gtg gtg gac     144
Gly Leu Ser Ser Cys Phe Leu Arg Ile Arg Ala Asp Gly Val Val Asp
        35                  40                  45 tgc gcg cgg ggc cag agc gcg cac agt ttg ctg gag atc aag gca gtc     192
Cys Ala Arg Gly Gln Ser Ala His Ser Leu Leu Glu Ile Lys Ala Val
    50                  55                  60 gct ctg cgg acc gtg gcc atc aag ggc gtg cac agc gtg cgg tac ctc     240
Ala Leu Arg Thr Val Ala Ile Lys Gly Val His Ser Val Arg Tyr Leu
65                  70                  75                  80 tgc atg ggc gcc gac ggc aag atg cag ggg ctg ctt cag tac tcg gag     288
Cys Met Gly Ala Asp Gly Lys Met Gln Gly Leu Leu Gln Tyr Ser Glu
                85                  90                  95 gaa gac tgt gct ttc gag gag gag atc cgc cca gat ggc tac aat gtg     336
Glu Asp Cys Ala Phe Glu Glu Glu Ile Arg Pro Asp Gly Tyr Asn Val
            100                 105                 110 tac cga tcc gag aag cac cgc ctc ccg gtc tcc ctg agc agt gcc aaa     384
Tyr Arg Ser Glu Lys His Arg Leu Pro Val Ser Leu Ser Ser Ala Lys
        115                 120                 125 cag cgg cag ctg tac aag aac aga ggc ttt ctt cca ctc tct cat ttc     432
Gln Arg Gln Leu Tyr Lys Asn Arg Gly Phe Leu Pro Leu Ser His Phe
    130                 135                 140 ctg ccc atg ctg ccc atg gtc cca gag gag cct gag gac ctc agg ggc     480
Leu Pro Met Leu Pro Met Val Pro Glu Glu Pro Glu Asp Leu Arg Gly
145                 150                 155                 160 cac ttg gaa tct gac atg ttc tct tcg ccc ctg gag acc gac agc atg     528
His Leu Glu Ser Asp Met Phe Ser Ser Pro Leu Glu Thr Asp Ser Met
                165                 170                 175 gac cca ttt ggg ctt gtc acc gga ctg gag gcc gtg agg agt ccc agc     576
Asp Pro Phe Gly Leu Val Thr Gly Leu Glu Ala Val Arg Ser Pro Ser
            180                 185                 190 ttt gag aag taa                                                      588
Phe Glu Lys
        195
```

<210> SEQ ID NO 6
<211> LENGTH: 195
<212> TYPE: PRT
<213> ORGANISM: Homo sapiens

<400> SEQUENCE: 6

```
Met Arg Pro Leu Ala Phe Ser Asp Ala Gly Pro His Val His Tyr Gly
1               5                   10                  15

Trp Gly Asp Pro Ile Arg Leu Arg His Leu Tyr Thr Ser Gly Pro His
            20                  25                  30
```

```
Gly Leu Ser Ser Cys Phe Leu Arg Ile Arg Ala Asp Gly Val Val Asp
                35                  40                  45

Cys Ala Arg Gly Gln Ser Ala His Ser Leu Leu Glu Ile Lys Ala Val
 50                  55                  60

Ala Leu Arg Thr Val Ala Ile Lys Gly Val His Ser Val Arg Tyr Leu
 65                  70                  75                  80

Cys Met Gly Ala Asp Gly Lys Met Gln Gly Leu Leu Gln Tyr Ser Glu
                 85                  90                  95

Glu Asp Cys Ala Phe Glu Glu Ile Arg Pro Asp Gly Tyr Asn Val
            100                 105                 110

Tyr Arg Ser Glu Lys His Arg Leu Pro Val Ser Leu Ser Ser Ala Lys
            115                 120                 125

Gln Arg Gln Leu Tyr Lys Asn Arg Gly Phe Leu Pro Leu Ser His Phe
130                 135                 140

Leu Pro Met Leu Pro Met Val Pro Glu Glu Pro Glu Asp Leu Arg Gly
145                 150                 155                 160

His Leu Glu Ser Asp Met Phe Ser Ser Pro Leu Glu Thr Asp Ser Met
                165                 170                 175

Asp Pro Phe Gly Leu Val Thr Gly Leu Glu Ala Val Arg Ser Pro Ser
            180                 185                 190

Phe Glu Lys
        195

<210> SEQ ID NO 7
<211> LENGTH: 630
<212> TYPE: DNA
<213> ORGANISM: Homo sapiens
<220> FEATURE:
<221> NAME/KEY: CDS
<222> LOCATION: (1)..(630)

<400> SEQUENCE: 7 atg gac tcg gac gag acc ggg ttc gag cac tca gga ctg tgg gtt tct      48
Met Asp Ser Asp Glu Thr Gly Phe Glu His Ser Gly Leu Trp Val Ser
 1               5                  10                  15 gtg ctg gct ggt ctt ctg ctg gga gcc tgc cag gca cat cca att cca      96
Val Leu Ala Gly Leu Leu Leu Gly Ala Cys Gln Ala His Pro Ile Pro
            20                  25                  30 gat tct tct cca tta tta caa ttc ggg ggc caa gtc cgg cag cgg tac     144
Asp Ser Ser Pro Leu Leu Gln Phe Gly Gly Gln Val Arg Gln Arg Tyr
         35                  40                  45 ctc tac aca gat gat gcc cag cag aca gaa gcc cac ctg gag atc agg     192
Leu Tyr Thr Asp Asp Ala Gln Gln Thr Glu Ala His Leu Glu Ile Arg
 50                  55                  60 gag gat ggg acg gtg ggg ggc gct gct gac cag agc ccc gaa agt ctc     240
Glu Asp Gly Thr Val Gly Gly Ala Ala Asp Gln Ser Pro Glu Ser Leu
 65                  70                  75                  80 ctg cag ctg aaa gcc ttg aag ccg gga gtt att caa atc ttg gga gtc     288
Leu Gln Leu Lys Ala Leu Lys Pro Gly Val Ile Gln Ile Leu Gly Val
                 85                  90                  95 aag aca tcc agg ttc ctg tgc cag cgg cca gat ggg gcc ctg tat gga     336
Lys Thr Ser Arg Phe Leu Cys Gln Arg Pro Asp Gly Ala Leu Tyr Gly
            100                 105                 110 tcg ctc cac ttt gac cct gag gcc tgc agc ttc cgg gag ctg ctt ctt     384
Ser Leu His Phe Asp Pro Glu Ala Cys Ser Phe Arg Glu Leu Leu Leu
         115                 120                 125 gag gac gga tac aat gtt tac cag tcc gaa gcc cac ggc ctc ccg ctg     432
Glu Asp Gly Tyr Asn Val Tyr Gln Ser Glu Ala His Gly Leu Pro Leu
130                 135                 140
```

```
cac ctg cca ggg aac aag tcc cca cac cgg gac cct gca ccc cga gga    480
His Leu Pro Gly Asn Lys Ser Pro His Arg Asp Pro Ala Pro Arg Gly
145                 150                 155                 160 cca gct cgc ttc ctg cca cta cca ggc ctg ccc ccc gca ccc ccg gag    528
Pro Ala Arg Phe Leu Pro Leu Pro Gly Leu Pro Pro Ala Pro Pro Glu
            165                 170                 175 cca ccc gga atc ctg gcc ccc cag ccc ccc gat gtg ggc tcc tcg gac    576
Pro Pro Gly Ile Leu Ala Pro Gln Pro Pro Asp Val Gly Ser Ser Asp
        180                 185                 190 cct ctg agc atg gtg gga cct tcc cag ggc cga agc ccc agc tac gct    624
Pro Leu Ser Met Val Gly Pro Ser Gln Gly Arg Ser Pro Ser Tyr Ala
    195                 200                 205 tcc tga                                                             630
Ser
```

<210> SEQ ID NO 8
<211> LENGTH: 209
<212> TYPE: PRT
<213> ORGANISM: Homo sapiens

<400> SEQUENCE: 8

```
Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 9
<211> LENGTH: 546
<212> TYPE: DNA
<213> ORGANISM: Homo sapiens
<220> FEATURE:
<221> NAME/KEY: CDS
<222> LOCATION: (1)..(546)

<400> SEQUENCE: 9

```
cac ccc atc cct gac tcc agt cct ctc ctg caa ttc ggg ggc caa gtc        48
His Pro Ile Pro Asp Ser Ser Pro Leu Leu Gln Phe Gly Gly Gln Val
1               5                   10                  15 cgg cag cgg tac ctc tac aca gat gat gcc cag cag aca gaa gcc cac        96
Arg Gln Arg Tyr Leu Tyr Thr Asp Asp Ala Gln Gln Thr Glu Ala His
                20                  25                  30 ctg gag atc agg gag gat ggg acg gtg ggg ggc gct gct gac cag agc       144
Leu Glu Ile Arg Glu Asp Gly Thr Val Gly Gly Ala Ala Asp Gln Ser
            35                  40                  45 ccc gaa agt ctc ctg cag ctg aaa gcc ttg aag ccg gga gtt att caa       192
Pro Glu Ser Leu Leu Gln Leu Lys Ala Leu Lys Pro Gly Val Ile Gln
        50                  55                  60 atc ttg gga gtc aag aca tcc agg ttc ctg tgc cag cgg cca gat ggg       240
Ile Leu Gly Val Lys Thr Ser Arg Phe Leu Cys Gln Arg Pro Asp Gly
65                  70                  75                  80 gcc ctg tat gga tcg ctc cac ttt gac cct gag gcc tgc agc ttc cgg       288
Ala Leu Tyr Gly Ser Leu His Phe Asp Pro Glu Ala Cys Ser Phe Arg
                85                  90                  95 gag ctg ctt ctt gag gac gga tac aat gtt tac cag tcc gaa gcc cac       336
Glu Leu Leu Leu Glu Asp Gly Tyr Asn Val Tyr Gln Ser Glu Ala His
                100                 105                 110 ggc ctc ccg ctg cac ctg cca ggg aac aag tcc cca cac cgg gac cct       384
Gly Leu Pro Leu His Leu Pro Gly Asn Lys Ser Pro His Arg Asp Pro
            115                 120                 125 gca ccc cga gga cca gct cgc ttc ctg cca cta cca ggc ctg ccc ccc       432
Ala Pro Arg Gly Pro Ala Arg Phe Leu Pro Leu Pro Gly Leu Pro Pro
        130                 135                 140 gca ccc ccg gag cca ccc gga atc ctg gcc ccc cag ccc ccc gat gtg       480
Ala Pro Pro Glu Pro Pro Gly Ile Leu Ala Pro Gln Pro Pro Asp Val
145                 150                 155                 160 ggc tcc tcg gac cct ctg agc atg gtg gga cct tcc cag ggc cga agc       528
Gly Ser Ser Asp Pro Leu Ser Met Val Gly Pro Ser Gln Gly Arg Ser
                165                 170                 175 ccc agc tac gct tcc tga                                                546
Pro Ser Tyr Ala Ser
                180

<210> SEQ ID NO 10
<211> LENGTH: 181
<212> TYPE: PRT
<213> ORGANISM: Homo sapiens

<400> SEQUENCE: 10

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125
```

```
Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 11
<211> LENGTH: 549
<212> TYPE: DNA
<213> ORGANISM: Homo sapiens
<220> FEATURE:
<221> NAME/KEY: CDS
<222> LOCATION: (1)..(549)

<400> SEQUENCE: 11
```

| | | | | | | | | | | | | | | | | |
|---|---|---|---|---|---|---|---|---|---|---|---|---|---|---|---|---|
| atg | cac | ccc | atc | cct | gac | tcc | agt | cct | ctc | ctg | caa | ttc | ggg | ggc | caa | 48 |
| Met | His | Pro | Ile | Pro | Asp | Ser | Ser | Pro | Leu | Leu | Gln | Phe | Gly | Gly | Gln | |
| 1 | | | | 5 | | | | | 10 | | | | | 15 | | |
| gtc | cgg | cag | cgg | tac | ctc | tac | aca | gat | gat | gcc | cag | cag | aca | gaa | gcc | 96 |
| Val | Arg | Gln | Arg | Tyr | Leu | Tyr | Thr | Asp | Asp | Ala | Gln | Gln | Thr | Glu | Ala | |
| | | | 20 | | | | | 25 | | | | | 30 | | | |
| cac | ctg | gag | atc | agg | gag | gat | ggg | acg | gtg | ggg | ggc | gct | gct | gac | cag | 144 |
| His | Leu | Glu | Ile | Arg | Glu | Asp | Gly | Thr | Val | Gly | Gly | Ala | Ala | Asp | Gln | |
| | | 35 | | | | | 40 | | | | | 45 | | | | |
| agc | ccc | gaa | agt | ctc | ctg | cag | ctg | aaa | gcc | ttg | aag | ccg | gga | gtt | att | 192 |
| Ser | Pro | Glu | Ser | Leu | Leu | Gln | Leu | Lys | Ala | Leu | Lys | Pro | Gly | Val | Ile | |
| | 50 | | | | | 55 | | | | | 60 | | | | | |
| caa | atc | ttg | gga | gtc | aag | aca | tcc | agg | ttc | ctg | tgc | cag | cgg | cca | gat | 240 |
| Gln | Ile | Leu | Gly | Val | Lys | Thr | Ser | Arg | Phe | Leu | Cys | Gln | Arg | Pro | Asp | |
| 65 | | | | | 70 | | | | | 75 | | | | | 80 | |
| ggg | gcc | ctg | tat | gga | tcg | ctc | cac | ttt | gac | cct | gag | gcc | tgc | agc | ttc | 288 |
| Gly | Ala | Leu | Tyr | Gly | Ser | Leu | His | Phe | Asp | Pro | Glu | Ala | Cys | Ser | Phe | |
| | | | | 85 | | | | | 90 | | | | | 95 | | |
| cgg | gag | ctg | ctt | ctt | gag | gac | gga | tac | aat | gtt | tac | cag | tcc | gaa | gcc | 336 |
| Arg | Glu | Leu | Leu | Leu | Glu | Asp | Gly | Tyr | Asn | Val | Tyr | Gln | Ser | Glu | Ala | |
| | | | 100 | | | | | 105 | | | | | 110 | | | |
| cac | ggc | ctc | ccg | ctg | cac | ctg | cca | ggg | aac | aag | tcc | cca | cac | cgg | gac | 384 |
| His | Gly | Leu | Pro | Leu | His | Leu | Pro | Gly | Asn | Lys | Ser | Pro | His | Arg | Asp | |
| | | 115 | | | | | 120 | | | | | 125 | | | | |
| cct | gca | ccc | cga | gga | cca | gct | cgc | ttc | ctg | cca | cta | cca | ggc | ctg | ccc | 432 |
| Pro | Ala | Pro | Arg | Gly | Pro | Ala | Arg | Phe | Leu | Pro | Leu | Pro | Gly | Leu | Pro | |
| | 130 | | | | | 135 | | | | | 140 | | | | | |
| ccc | gca | ccc | ccg | gag | cca | ccc | gga | atc | ctg | gcc | ccc | cag | ccc | ccc | gat | 480 |
| Pro | Ala | Pro | Pro | Glu | Pro | Pro | Gly | Ile | Leu | Ala | Pro | Gln | Pro | Pro | Asp | |
| 145 | | | | | 150 | | | | | 155 | | | | | 160 | |
| gtg | ggc | tcc | tcg | gac | cct | ctg | agc | atg | gtg | gga | cct | tcc | cag | ggc | cga | 528 |
| Val | Gly | Ser | Ser | Asp | Pro | Leu | Ser | Met | Val | Gly | Pro | Ser | Gln | Gly | Arg | |
| | | | | 165 | | | | | 170 | | | | | 175 | | |
| agc | ccc | agc | tac | gct | tcc | tga | | | | | | | | | | 549 |
| Ser | Pro | Ser | Tyr | Ala | Ser | | | | | | | | | | | |
| | | | 180 | | | | | | | | | | | | | |

```
<210> SEQ ID NO 12
<211> LENGTH: 182
<212> TYPE: PRT
<213> ORGANISM: Homo sapiens

<400> SEQUENCE: 12

Met His Pro Ile Pro Asp Ser Ser Pro Leu Leu Gln Phe Gly Gly Gln
```

-continued

```
                1               5                  10                 15
Val Arg Gln Arg Tyr Leu Tyr Thr Asp Asp Ala Gln Gln Thr Glu Ala
                    20                  25                 30

His Leu Glu Ile Arg Glu Asp Gly Thr Val Gly Gly Ala Ala Asp Gln
                    35                  40                 45

Ser Pro Glu Ser Leu Leu Gln Leu Lys Ala Leu Lys Pro Gly Val Ile
         50                  55                 60

Gln Ile Leu Gly Val Lys Thr Ser Arg Phe Leu Cys Gln Arg Pro Asp
 65                  70                  75                 80

Gly Ala Leu Tyr Gly Ser Leu His Phe Asp Pro Glu Ala Cys Ser Phe
                     85                 90                 95

Arg Glu Leu Leu Leu Glu Asp Gly Tyr Asn Val Tyr Gln Ser Glu Ala
                    100                 105                110

His Gly Leu Pro Leu His Leu Pro Gly Asn Lys Ser Pro His Arg Asp
                    115                 120                125

Pro Ala Pro Arg Gly Pro Ala Arg Phe Leu Pro Leu Pro Gly Leu Pro
                    130                 135                140

Pro Ala Pro Pro Glu Pro Pro Gly Ile Leu Ala Pro Gln Pro Pro Asp
145                 150                 155                160

Val Gly Ser Ser Asp Pro Leu Ser Met Val Gly Pro Ser Gln Gly Arg
                    165                 170                175

Ser Pro Ser Tyr Ala Ser
                    180

<210> SEQ ID NO 13
<211> LENGTH: 756
<212> TYPE: DNA
<213> ORGANISM: Homo sapiens
<220> FEATURE:
<221> NAME/KEY: CDS
<222> LOCATION: (1)..(756)

<400> SEQUENCE: 13 atg ttg ggg gcc cgc ctc agg ctc tgg gtc tgt gcc ttg tgc agc gtc      48
Met Leu Gly Ala Arg Leu Arg Leu Trp Val Cys Ala Leu Cys Ser Val
 1               5                  10                 15 tgc agc atg agc gtc ctc aga gcc tat ccc aat gcc tcc cca ctg ctc      96
Cys Ser Met Ser Val Leu Arg Ala Tyr Pro Asn Ala Ser Pro Leu Leu
                    20                  25                 30 ggc tcc agc tgg ggt ggc ctg atc cac ctg tac aca gcc aca gcc agg     144
Gly Ser Ser Trp Gly Gly Leu Ile His Leu Tyr Thr Ala Thr Ala Arg
                35                  40                 45 aac agc tac cac ctg cag atc cac aag aat ggc cat gtg gat ggc gca     192
Asn Ser Tyr His Leu Gln Ile His Lys Asn Gly His Val Asp Gly Ala
         50                  55                 60 ccc cat cag acc atc tac agt gcc ctg atg atc aga tca gag gat gct     240
Pro His Gln Thr Ile Tyr Ser Ala Leu Met Ile Arg Ser Glu Asp Ala
 65                  70                  75                 80 ggc ttt gtg gtg att aca ggt gtg atg agc aga aga tac ctc tgc atg     288
Gly Phe Val Val Ile Thr Gly Val Met Ser Arg Arg Tyr Leu Cys Met
                     85                 90                 95 gat ttc aga ggc aac att ttt gga tca cac tat ttc gac ccg gag aac     336
Asp Phe Arg Gly Asn Ile Phe Gly Ser His Tyr Phe Asp Pro Glu Asn
                    100                 105                110 tgc agg ttc caa cac cag acg ctg gaa aac ggg tac gac gtc tac cac     384
Cys Arg Phe Gln His Gln Thr Leu Glu Asn Gly Tyr Asp Val Tyr His
                    115                 120                125 tct cct cag tat cac ttc ctg gtc agt ctg ggc cgg gcg aag aga gcc     432
Ser Pro Gln Tyr His Phe Leu Val Ser Leu Gly Arg Ala Lys Arg Ala
```

```
ttc ctg cca ggc atg aac cca ccc ccg tac tcc cag ttc ctg tcc cgg      480
Phe Leu Pro Gly Met Asn Pro Pro Pro Tyr Ser Gln Phe Leu Ser Arg
145                 150                 155                 160 agg aac gag atc ccc cta att cac ttc aac acc cca ata cca cgg cgg      528
Arg Asn Glu Ile Pro Leu Ile His Phe Asn Thr Pro Ile Pro Arg Arg
                165                 170                 175 cac acc cgg agc gcc gag gac gac tcg gag cgg gac ccc ctg aac gtg      576
His Thr Arg Ser Ala Glu Asp Asp Ser Glu Arg Asp Pro Leu Asn Val
            180                 185                 190 ctg aag ccc cgg gcc cgg atg acc ccg gcc ccg gcc tcc tgt tca cag      624
Leu Lys Pro Arg Ala Arg Met Thr Pro Ala Pro Ala Ser Cys Ser Gln
        195                 200                 205 gag ctc ccg agc gcc gag gac aac agc ccg atg gcc agt gac cca tta      672
Glu Leu Pro Ser Ala Glu Asp Asn Ser Pro Met Ala Ser Asp Pro Leu
    210                 215                 220 ggg gtg gtc agg ggc ggt cga gtg aac acg cac gct ggg gga acg ggc      720
Gly Val Val Arg Gly Gly Arg Val Asn Thr His Ala Gly Gly Thr Gly
225                 230                 235                 240 ccg gaa ggc tgc cgc ccc ttc gcc aag ttc atc tag                       756
Pro Glu Gly Cys Arg Pro Phe Ala Lys Phe Ile
                245                 250

<210> SEQ ID NO 14
<211> LENGTH: 251
<212> TYPE: PRT
<213> ORGANISM: Homo sapiens

<400> SEQUENCE: 14

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220
```

```
Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 15
<211> LENGTH: 684
<212> TYPE: DNA
<213> ORGANISM: Homo sapiens
<220> FEATURE:
<221> NAME/KEY: CDS
<222> LOCATION: (1)..(684)

<400> SEQUENCE: 15 tat ccc aat gcc tcc cca ctg ctc ggc tcc agc tgg ggt ggc ctg atc       48
Tyr Pro Asn Ala Ser Pro Leu Leu Gly Ser Ser Trp Gly Gly Leu Ile
1               5                   10                  15 cac ctg tac aca gcc aca gcc agg aac agc tac cac ctg cag atc cac       96
His Leu Tyr Thr Ala Thr Ala Arg Asn Ser Tyr His Leu Gln Ile His
            20                  25                  30 aag aat ggc cat gtg gat ggc gca ccc cat cag acc atc tac agt gcc      144
Lys Asn Gly His Val Asp Gly Ala Pro His Gln Thr Ile Tyr Ser Ala
        35                  40                  45 ctg atg atc aga tca gag gat gct ggc ttt gtg gtg att aca ggt gtg      192
Leu Met Ile Arg Ser Glu Asp Ala Gly Phe Val Val Ile Thr Gly Val
    50                  55                  60 atg agc aga aga tac ctc tgc atg gat ttc aga ggc aac att ttt gga      240
Met Ser Arg Arg Tyr Leu Cys Met Asp Phe Arg Gly Asn Ile Phe Gly
65                  70                  75                  80 tca cac tat ttc gac ccg gag aac tgc agg ttc caa cac cag acg ctg      288
Ser His Tyr Phe Asp Pro Glu Asn Cys Arg Phe Gln His Gln Thr Leu
                85                  90                  95 gaa aac ggg tac gac gtc tac cac tct cct cag tat cac ttc ctg gtc      336
Glu Asn Gly Tyr Asp Val Tyr His Ser Pro Gln Tyr His Phe Leu Val
            100                 105                 110 agt ctg ggc cgg gcg aag aga gcc ttc ctg cca ggc atg aac cca ccc      384
Ser Leu Gly Arg Ala Lys Arg Ala Phe Leu Pro Gly Met Asn Pro Pro
        115                 120                 125 ccg tac tcc cag ttc ctg tcc cgg agg aac gag atc ccc cta att cac      432
Pro Tyr Ser Gln Phe Leu Ser Arg Arg Asn Glu Ile Pro Leu Ile His
    130                 135                 140 ttc aac acc ccc ata cca cgg cgg cac acc cgg agc gcc gag gac gac      480
Phe Asn Thr Pro Ile Pro Arg Arg His Thr Arg Ser Ala Glu Asp Asp
145                 150                 155                 160 tcg gag cgg gac ccc ctg aac gtg ctg aag ccc cgg gcc cgg atg acc      528
Ser Glu Arg Asp Pro Leu Asn Val Leu Lys Pro Arg Ala Arg Met Thr
                165                 170                 175 ccg gcc ccg gcc tcc tgt tca cag gag ctc ccc agc gcc gag gac aac      576
Pro Ala Pro Ala Ser Cys Ser Gln Glu Leu Pro Ser Ala Glu Asp Asn
            180                 185                 190 agc ccg atg gcc agt gac cca tta ggg gtg gtc agg ggc ggt cga gtg      624
Ser Pro Met Ala Ser Asp Pro Leu Gly Val Val Arg Gly Gly Arg Val
        195                 200                 205 aac acg cac gct ggg gga acg ggc ccg gaa ggc tgc cgc ccc ttc gcc      672
Asn Thr His Ala Gly Gly Thr Gly Pro Glu Gly Cys Arg Pro Phe Ala
    210                 215                 220 aag ttc atc tag                                                      684
Lys Phe Ile
225

<210> SEQ ID NO 16
<211> LENGTH: 227
```

```
<212> TYPE: PRT
<213> ORGANISM: Homo sapiens

<400> SEQUENCE: 16

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
    210                 215                 220

Lys Phe Ile
225

<210> SEQ ID NO 17
<211> LENGTH: 687
<212> TYPE: DNA
<213> ORGANISM: Homo sapiens
<220> FEATURE:
<221> NAME/KEY: CDS
<222> LOCATION: (1)..(687)

<400> SEQUENCE: 17 atg tat ccc aat gcc tcc cca ctg ctc ggc tcc agc tgg ggt ggc ctg      48
Met Tyr Pro Asn Ala Ser Pro Leu Leu Gly Ser Ser Trp Gly Gly Leu
1               5                   10                  15 atc cac ctg tac aca gcc aca gcc agg aac agc tac cac ctg cag atc      96
Ile His Leu Tyr Thr Ala Thr Ala Arg Asn Ser Tyr His Leu Gln Ile
            20                  25                  30 cac aag aat ggc cat gtg gat ggc gca ccc cat cag acc atc tac agt     144
His Lys Asn Gly His Val Asp Gly Ala Pro His Gln Thr Ile Tyr Ser
        35                  40                  45 gcc ctg atg atc aga tca gag gat gct ggc ttt gtg gtg att aca ggt     192
Ala Leu Met Ile Arg Ser Glu Asp Ala Gly Phe Val Val Ile Thr Gly
    50                  55                  60 gtg atg agc aga aga tac ctc tgc atg gat ttc aga ggc aac att ttt     240
Val Met Ser Arg Arg Tyr Leu Cys Met Asp Phe Arg Gly Asn Ile Phe
65                  70                  75                  80
```

```
gga tca cac tat ttc gac ccg gag aac tgc agg ttc aa cac cag acg      288
Gly Ser His Tyr Phe Asp Pro Glu Asn Cys Arg Phe Gln His Gln Thr
                85                  90                  95 ctg gaa aac ggg tac gac gtc tac cac tct cct cag tat cac ttc ctg      336
Leu Glu Asn Gly Tyr Asp Val Tyr His Ser Pro Gln Tyr His Phe Leu
            100                 105                 110 gtc agt ctg ggc cgg gcg aag aga gcc ttc ctg cca ggc atg aac cca      384
Val Ser Leu Gly Arg Ala Lys Arg Ala Phe Leu Pro Gly Met Asn Pro
            115                 120                 125 ccc ccg tac tcc cag ttc ctg tcc agg agg aac gag atc ccc cta att      432
Pro Pro Tyr Ser Gln Phe Leu Ser Arg Arg Asn Glu Ile Pro Leu Ile
        130                 135                 140 cac ttc aac acc ccc ata cca cgg cgg cac acc cgg agc gcc gag gac      480
His Phe Asn Thr Pro Ile Pro Arg Arg His Thr Arg Ser Ala Glu Asp
145                 150                 155                 160 gac tcg gag cgg gac ccc ctg aac gtg ctg aag ccc cgg gcc cgg atg      528
Asp Ser Glu Arg Asp Pro Leu Asn Val Leu Lys Pro Arg Ala Arg Met
                165                 170                 175 acc ccg gcc ccg gcc tcc tgt tca cag gag ctc ccg agc gcc gag gac      576
Thr Pro Ala Pro Ala Ser Cys Ser Gln Glu Leu Pro Ser Ala Glu Asp
            180                 185                 190 aac agc ccg atg gcc agt gac cca tta ggg gtg gtc agg ggc ggt cga      624
Asn Ser Pro Met Ala Ser Asp Pro Leu Gly Val Val Arg Gly Gly Arg
            195                 200                 205 gtg aac acg cac gct ggg gga acg ggc ccg gaa ggc tgc cgc ccc ttc      672
Val Asn Thr His Ala Gly Gly Thr Gly Pro Glu Gly Cys Arg Pro Phe
        210                 215                 220 gcc aag ttc atc tag                                                  687
Ala Lys Phe Ile
225

<210> SEQ ID NO 18
<211> LENGTH: 228
<212> TYPE: PRT
<213> ORGANISM: Homo sapiens

<400> SEQUENCE: 18

Met Tyr Pro Asn Ala Ser Pro Leu Leu Gly Ser Ser Trp Gly Gly Leu
1               5                   10                  15

Ile His Leu Tyr Thr Ala Thr Ala Arg Asn Ser Tyr His Leu Gln Ile
            20                  25                  30

His Lys Asn Gly His Val Asp Gly Ala Pro His Gln Thr Ile Tyr Ser
        35                  40                  45

Ala Leu Met Ile Arg Ser Glu Asp Ala Gly Phe Val Val Ile Thr Gly
    50                  55                  60

Val Met Ser Arg Arg Tyr Leu Cys Met Asp Phe Arg Gly Asn Ile Phe
65                  70                  75                  80

Gly Ser His Tyr Phe Asp Pro Glu Asn Cys Arg Phe Gln His Gln Thr
                85                  90                  95

Leu Glu Asn Gly Tyr Asp Val Tyr His Ser Pro Gln Tyr His Phe Leu
            100                 105                 110

Val Ser Leu Gly Arg Ala Lys Arg Ala Phe Leu Pro Gly Met Asn Pro
            115                 120                 125

Pro Pro Tyr Ser Gln Phe Leu Ser Arg Arg Asn Glu Ile Pro Leu Ile
        130                 135                 140

His Phe Asn Thr Pro Ile Pro Arg Arg His Thr Arg Ser Ala Glu Asp
145                 150                 155                 160

Asp Ser Glu Arg Asp Pro Leu Asn Val Leu Lys Pro Arg Ala Arg Met
```

```
                      165                 170                 175
Thr Pro Ala Pro Ala Ser Cys Ser Gln Glu Leu Pro Ser Ala Glu Asp
            180                 185                 190

Asn Ser Pro Met Ala Ser Asp Pro Leu Gly Val Val Arg Gly Gly Arg
            195                 200                 205

Val Asn Thr His Ala Gly Gly Thr Gly Pro Glu Gly Cys Arg Pro Phe
        210                 215                 220

Ala Lys Phe Ile
225

<210> SEQ ID NO 19
<211> LENGTH: 534
<212> TYPE: DNA
<213> ORGANISM: Artificial
<220> FEATURE:
<223> OTHER INFORMATION: truncated protein
<220> FEATURE:
<221> NAME/KEY: CDS
<222> LOCATION: (1)..(534)

<400> SEQUENCE: 19 atg cgg agc ggg tgt gtg gtg gtc cac gta tgg atc ctg gcc ggc ctc      48
Met Arg Ser Gly Cys Val Val Val Val His Val Trp Ile Leu Ala Gly Leu
1               5                   10                  15 tgg ctg gcc gtg gcc ggg cgt cca ctt gct ttt tct gat gct ggt cca      96
Trp Leu Ala Val Ala Gly Arg Pro Leu Ala Phe Ser Asp Ala Gly Pro
            20                  25                  30 cac gtt cac tac ggc tgg ggc gac ccc atc cgc ctg cgg cac ctg tac     144
His Val His Tyr Gly Trp Gly Asp Pro Ile Arg Leu Arg His Leu Tyr
        35                  40                  45 acc tcc ggc ccc cac ggg ctc tcc agc tgc ttc ctg cgc atc cgt gcc     192
Thr Ser Gly Pro His Gly Leu Ser Ser Cys Phe Leu Arg Ile Arg Ala
    50                  55                  60 gac ggc gtc gtg gac tgc gcg cgg ggc cag agc gcg cac agt ttg ctg     240
Asp Gly Val Val Asp Cys Ala Arg Gly Gln Ser Ala His Ser Leu Leu
65                  70                  75                  80 gag atc aag gca gtc gct ctg cgg acc gtg gcc atc aag ggc gtg cac     288
Glu Ile Lys Ala Val Ala Leu Arg Thr Val Ala Ile Lys Gly Val His
                85                  90                  95 agc gtg cgg tac ctc tgc atg ggc gcc gac ggc aag atg cag ggg ctg     336
Ser Val Arg Tyr Leu Cys Met Gly Ala Asp Gly Lys Met Gln Gly Leu
            100                 105                 110 ctt cag tac tcg gag gaa gac tgt gct ttc gag gag gag atc cgc cca     384
Leu Gln Tyr Ser Glu Glu Asp Cys Ala Phe Glu Glu Glu Ile Arg Pro
        115                 120                 125 gat ggc tac aat gtg tac cga tcc gag aag cac cgc ctc ccg gtc tcc     432
Asp Gly Tyr Asn Val Tyr Arg Ser Glu Lys His Arg Leu Pro Val Ser
    130                 135                 140 ctg agc agt gcc aaa cag cgg cag ctg tac aag aac aga ggc ttt ctt     480
Leu Ser Ser Ala Lys Gln Arg Gln Leu Tyr Lys Asn Arg Gly Phe Leu
145                 150                 155                 160 cca ctc tct cat ttc ctg ccc atg ctg ccc atg gtc cca gag gag cct     528
Pro Leu Ser His Phe Leu Pro Met Leu Pro Met Val Pro Glu Glu Pro
                165                 170                 175 gag taa                                                              534
Glu

<210> SEQ ID NO 20
<211> LENGTH: 177
<212> TYPE: PRT
<213> ORGANISM: Artificial
<220> FEATURE:
```

-continued

<223> OTHER INFORMATION: Synthetic Construct

<400> SEQUENCE: 20

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu

<210> SEQ ID NO 21
<211> LENGTH: 624
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(624)

<400> SEQUENCE: 21 atg cgg agc ggg tgt gtg gtg gtc cac gta tgg atc ctg gcc ggc ctc    48
Met Arg Ser Gly Cys Val Val Val His Val Trp Ile Leu Ala Gly Leu
1               5                   10                  15 tgg ctg gcc gtg gcc ggg cgt cca ctt gct ttt tct gat gct ggt cca    96
Trp Leu Ala Val Ala Gly Arg Pro Leu Ala Phe Ser Asp Ala Gly Pro
            20                  25                  30 cac gtt cac tac ggc tgg ggc gac ccc atc cgc ctg cgg cac ctg tac   144
His Val His Tyr Gly Trp Gly Asp Pro Ile Arg Leu Arg His Leu Tyr
        35                  40                  45 acc gat gat gcc cag cag aca gaa tgc ttc ctg cgc atc cgt gcc gac   192
Thr Asp Asp Ala Gln Gln Thr Glu Cys Phe Leu Arg Ile Arg Ala Asp
    50                  55                  60 ggc gtc gtg gac tgc gcg cgg ggc cag agc gcg cac agt ttg ctg gag   240
Gly Val Val Asp Cys Ala Arg Gly Gln Ser Ala His Ser Leu Leu Glu
65                  70                  75                  80 atc aag gca gtc gct ctg cgg acc gtg gcc atc aag ggc gtg cac agc   288
Ile Lys Ala Val Ala Leu Arg Thr Val Ala Ile Lys Gly Val His Ser
                85                  90                  95 gtg cgg tac ctc tgc atg ggc gcc gac ggc aag atg cag ggg ctg ctt   336
Val Arg Tyr Leu Cys Met Gly Ala Asp Gly Lys Met Gln Gly Leu Leu
            100                 105                 110

| | | | | | | | | | | | | | | | | |
|---|---|---|---|---|---|---|---|---|---|---|---|---|---|---|---|---|
| cag | tac | tcg | gag | gaa | gac | tgt | gct | ttc | gag | gag | ctg | ctt | ctt | gag | gac | 384 |
| Gln | Tyr | Ser | Glu | Glu | Asp | Cys | Ala | Phe | Glu | Glu | Leu | Leu | Leu | Glu | Asp | |
| | | 115 | | | | 120 | | | | | 125 | | | | | |
| gga | tac | aat | gtt | tac | cag | tcc | gaa | gcc | cac | ggc | ctc | ccg | ctg | cac | ctg | 432 |
| Gly | Tyr | Asn | Val | Tyr | Gln | Ser | Glu | Ala | His | Gly | Leu | Pro | Leu | His | Leu | |
| 130 | | | | | 135 | | | | | 140 | | | | | | |
| cca | ggg | aac | aag | tcc | cca | cac | cgg | gac | cct | gca | ccc | cga | gga | cca | gct | 480 |
| Pro | Gly | Asn | Lys | Ser | Pro | His | Arg | Asp | Pro | Ala | Pro | Arg | Gly | Pro | Ala | |
| 145 | | | | | 150 | | | | | 155 | | | | | 160 | |
| cgc | ttc | ctg | cca | cta | cca | ggc | ctg | ccc | ccg | gca | ccc | cgg | gag | cca | ccc | 528 |
| Arg | Phe | Leu | Pro | Leu | Pro | Gly | Leu | Pro | Pro | Ala | Pro | Pro | Glu | Pro | Pro | |
| | | | | 165 | | | | | 170 | | | | | 175 | | |
| gga | atc | ctg | gcc | ccc | cag | ccc | ccc | gat | gtg | ggc | tcc | tcg | gac | cct | ctg | 576 |
| Gly | Ile | Leu | Ala | Pro | Gln | Pro | Pro | Asp | Val | Gly | Ser | Ser | Asp | Pro | Leu | |
| | | 180 | | | | 185 | | | | | 190 | | | | | |
| agc | atg | gtg | gga | cct | tcc | cag | ggc | cga | agc | ccc | agc | tac | gct | tcc | tga | 624 |
| Ser | Met | Val | Gly | Pro | Ser | Gln | Gly | Arg | Ser | Pro | Ser | Tyr | Ala | Ser | | |
| | | 195 | | | | 200 | | | | | 205 | | | | | |

<210> SEQ ID NO 22
<211> LENGTH: 207
<212> TYPE: PRT
<213> ORGANISM: Artificial
<220> FEATURE:
<223> OTHER INFORMATION: Synthetic Construct

<400> SEQUENCE: 22

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Asp Asp Ala Gln Gln Thr Glu Cys Phe Leu Arg Ile Arg Ala Asp
    50                  55                  60

Gly Val Val Asp Cys Ala Arg Gly Gln Ser Ala His Ser Leu Leu Glu
65                  70                  75                  80

Ile Lys Ala Val Ala Leu Arg Thr Val Ala Ile Lys Gly Val His Ser
                85                  90                  95

Val Arg Tyr Leu Cys Met Gly Ala Asp Gly Lys Met Gln Gly Leu Leu
            100                 105                 110

Gln Tyr Ser Glu Glu Asp Cys Ala Phe Glu Glu Leu Leu Leu Glu Asp
        115                 120                 125

Gly Tyr Asn Val Tyr Gln Ser Glu Ala His Gly Leu Pro Leu His Leu
130                 135                 140

Pro Gly Asn Lys Ser Pro His Arg Asp Pro Ala Pro Arg Gly Pro Ala
145                 150                 155                 160

Arg Phe Leu Pro Leu Pro Gly Leu Pro Pro Ala Pro Pro Glu Pro Pro
                165                 170                 175

Gly Ile Leu Ala Pro Gln Pro Pro Asp Val Gly Ser Ser Asp Pro Leu
            180                 185                 190

Ser Met Val Gly Pro Ser Gln Gly Arg Ser Pro Ser Tyr Ala Ser
        195                 200                 205

<210> SEQ ID NO 23
<211> LENGTH: 627
<212> TYPE: DNA
<213> ORGANISM: Artificial
<220> FEATURE:
<223> OTHER INFORMATION: chimeric fusion protein

<220> FEATURE:
<221> NAME/KEY: CDS
<222> LOCATION: (1)..(627)

<400> SEQUENCE: 23

```
atg cgg agc ggg tgt gtg gtg gtc cac gta tgg atc ctg gcc ggc ctc       48
Met Arg Ser Gly Cys Val Val Val His Val Trp Ile Leu Ala Gly Leu
1               5                   10                  15 tgg ctg gcc gtg gcc ggg cgt cca ctt gct ttt tct gat gct ggt cca       96
Trp Leu Ala Val Ala Gly Arg Pro Leu Ala Phe Ser Asp Ala Gly Pro
            20                  25                  30 cac gtt cac tac ggc tgg ggc gac ccc atc cgc ctg cgg cac ctg tac      144
His Val His Tyr Gly Trp Gly Asp Pro Ile Arg Leu Arg His Leu Tyr
        35                  40                  45 acc tcc ggc ccc cac ggg ctc tcc agc tgc ttc ctg cgc atc cgt gcc      192
Thr Ser Gly Pro His Gly Leu Ser Ser Cys Phe Leu Arg Ile Arg Ala
    50                  55                  60 gac ggc gtc gtg gac tgc gcg cgg ggc cag agc gcg cac agt ttg ctg      240
Asp Gly Val Val Asp Cys Ala Arg Gly Gln Ser Ala His Ser Leu Leu
65                  70                  75                  80 cag ctg aaa gcc ttg aag ccg gga gtt att caa atc ttg gga gtc aag      288
Gln Leu Lys Ala Leu Lys Pro Gly Val Ile Gln Ile Leu Gly Val Lys
                85                  90                  95 aca tcc agg ttc ctg tgc cag cgg cca gat ggg gcc ctg tat gga tcg      336
Thr Ser Arg Phe Leu Cys Gln Arg Pro Asp Gly Ala Leu Tyr Gly Ser
            100                 105                 110 ctc cac ttt gac cct gag gcc tgc agc ttc cgg gag ctg ctt ctt gag      384
Leu His Phe Asp Pro Glu Ala Cys Ser Phe Arg Glu Leu Leu Leu Glu
        115                 120                 125 gac gga tac aat gtt tac cag tcc gaa gcc cac ggc ctc ccg ctg cac      432
Asp Gly Tyr Asn Val Tyr Gln Ser Glu Ala His Gly Leu Pro Leu His
    130                 135                 140 ctg cca ggg aac aag tcc cca cac cgg gac cct gca ccc cga gga cca      480
Leu Pro Gly Asn Lys Ser Pro His Arg Asp Pro Ala Pro Arg Gly Pro
145                 150                 155                 160 gct cgc ttc ctg cca cta cca ggc ctg ccc cca gca ccc cgg agc cca      528
Ala Arg Phe Leu Pro Leu Pro Gly Leu Pro Pro Ala Pro Pro Glu Pro
                165                 170                 175 ccc gga atc ctg gcc ccc cag ccc ccc gat gtg ggc tcc tcg gac cct      576
Pro Gly Ile Leu Ala Pro Gln Pro Pro Asp Val Gly Ser Ser Asp Pro
            180                 185                 190 ctg agc atg gtg gga cct tcc cag ggc cga agc ccc agc tac gct tcc      624
Leu Ser Met Val Gly Pro Ser Gln Gly Arg Ser Pro Ser Tyr Ala Ser
        195                 200                 205 tga                                                                   627
```

<210> SEQ ID NO 24
<211> LENGTH: 208
<212> TYPE: PRT
<213> ORGANISM: Artificial
<220> FEATURE:
<223> OTHER INFORMATION: Synthetic Construct

<400> SEQUENCE: 24

```
Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
```

```
                50                  55                  60
Asp Gly Val Val Asp Cys Ala Arg Gly Gln Ser Ala His Ser Leu Leu
 65                  70                  75                  80

Gln Leu Lys Ala Leu Lys Pro Gly Val Ile Gln Ile Leu Gly Val Lys
                 85                  90                  95

Thr Ser Arg Phe Leu Cys Gln Arg Pro Asp Gly Ala Leu Tyr Gly Ser
            100                 105                 110

Leu His Phe Asp Pro Glu Ala Cys Ser Phe Arg Glu Leu Leu Leu Glu
        115                 120                 125

Asp Gly Tyr Asn Val Tyr Gln Ser Glu Ala His Gly Leu Pro Leu His
    130                 135                 140

Leu Pro Gly Asn Lys Ser Pro His Arg Asp Pro Ala Pro Arg Gly Pro
145                 150                 155                 160

Ala Arg Phe Leu Pro Leu Pro Gly Leu Pro Pro Ala Pro Pro Glu Pro
                165                 170                 175

Pro Gly Ile Leu Ala Pro Gln Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205

<210> SEQ ID NO 25
<211> LENGTH: 624
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(624)

<400> SEQUENCE: 25 atg cgg agc ggg tgt gtg gtg gtc cac gta tgg atc ctg gcc ggc ctc    48
Met Arg Ser Gly Cys Val Val Val His Val Trp Ile Leu Ala Gly Leu
  1               5                  10                  15 tgg ctg gcc gtg gcc ggg cgt cca ctt gct ttt tct gat gct ggt cca    96
Trp Leu Ala Val Ala Gly Arg Pro Leu Ala Phe Ser Asp Ala Gly Pro
             20                  25                  30 cac gtt cac tac ggc tgg ggc gac ccc atc cgc ctg cgg cac ctg tac   144
His Val His Tyr Gly Trp Gly Asp Pro Ile Arg Leu Arg His Leu Tyr
         35                  40                  45 acc gat gat gcc cag cag aca gaa gcc cac ctg gag atc agg gag gat   192
Thr Asp Asp Ala Gln Gln Thr Glu Ala His Leu Glu Ile Arg Glu Asp
     50                  55                  60 ggg acg gtg ggg ggc gct gct gac cag agc ccc gaa agt ctc ctg cag   240
Gly Thr Val Gly Gly Ala Ala Asp Gln Ser Pro Glu Ser Leu Leu Gln
 65                  70                  75                  80 ctg aaa gcc ttg aag ccg gga gtt att caa atc ttg gga gtc aag aca   288
Leu Lys Ala Leu Lys Pro Gly Val Ile Gln Ile Leu Gly Val Lys Thr
                 85                  90                  95 tcc agg ttc ctg tgc cag cgg cca gat ggg gcc ctg tat gga tcg ctc   336
Ser Arg Phe Leu Cys Gln Arg Pro Asp Gly Ala Leu Tyr Gly Ser Leu
            100                 105                 110 cac ttt gac cct gag gcc tgc agc ttc cgg gag ctg ctt ctt gag gac   384
His Phe Asp Pro Glu Ala Cys Ser Phe Arg Glu Leu Leu Leu Glu Asp
        115                 120                 125 gga tac aat gtt tac cag tcc gaa gcc cac ggc ctc ccg ctg cac ctg   432
Gly Tyr Asn Val Tyr Gln Ser Glu Ala His Gly Leu Pro Leu His Leu
    130                 135                 140 cca ggg aac aag tcc cca cac cgg gac cct gca ccc cga gga cca gct   480
Pro Gly Asn Lys Ser Pro His Arg Asp Pro Ala Pro Arg Gly Pro Ala
```

```
                145                 150                 155                 160
cgc ttc ctg cca cta cca ggc ctg ccc ccc gca ccc ccg gag cca ccc         528
Arg Phe Leu Pro Leu Pro Gly Leu Pro Pro Ala Pro Pro Glu Pro Pro
                165                 170                 175 gga atc ctg gcc ccc cag ccc ccc gat gtg ggc tcg tcg gac cct ctg         576
Gly Ile Leu Ala Pro Gln Pro Pro Asp Val Gly Ser Ser Asp Pro Leu
                180                 185                 190 agc atg gtg gga cct tcc cag ggc cga agc ccc agc tac gct tcc tga         624
Ser Met Val Gly Pro Ser Gln Gly Arg Ser Pro Ser Tyr Ala Ser
                195                 200                 205

<210> SEQ ID NO 26
<211> LENGTH: 207
<212> TYPE: PRT
<213> ORGANISM: Artificial
<220> FEATURE:
<223> OTHER INFORMATION: Synthetic Construct

<400> SEQUENCE: 26

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
                35                  40                  45

Thr Asp Asp Ala Gln Gln Thr Glu Ala His Leu Glu Ile Arg Glu Asp
            50                  55                  60

Gly Thr Val Gly Gly Ala Ala Asp Gln Ser Pro Glu Ser Leu Leu Gln
65                  70                  75                  80

Leu Lys Ala Leu Lys Pro Gly Val Ile Gln Ile Leu Gly Val Lys Thr
                85                  90                  95

Ser Arg Phe Leu Cys Gln Arg Pro Asp Gly Ala Leu Tyr Gly Ser Leu
                100                 105                 110

His Phe Asp Pro Glu Ala Cys Ser Phe Arg Glu Leu Leu Leu Glu Asp
                115                 120                 125

Gly Tyr Asn Val Tyr Gln Ser Glu Ala His Gly Leu Pro Leu His Leu
            130                 135                 140

Pro Gly Asn Lys Ser Pro His Arg Asp Pro Ala Pro Arg Gly Pro Ala
145                 150                 155                 160

Arg Phe Leu Pro Leu Pro Gly Leu Pro Pro Ala Pro Pro Glu Pro Pro
                165                 170                 175

Gly Ile Leu Ala Pro Gln Pro Pro Asp Val Gly Ser Ser Asp Pro Leu
                180                 185                 190

Ser Met Val Gly Pro Ser Gln Gly Arg Ser Pro Ser Tyr Ala Ser
                195                 200                 205

<210> SEQ ID NO 27
<211> LENGTH: 624
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(624)

<400> SEQUENCE: 27 atg cgg agc ggg tgt gtg gtg gtc cac gta tgg atc ctg gcc ggc ctc         48
Met Arg Ser Gly Cys Val Val Val His Val Trp Ile Leu Ala Gly Leu
1               5                   10                  15
```

```
tgg ctg gcc gtg gcc ggg cgt cca ctt gct ttt tct gat gct ggt cca      96
Trp Leu Ala Val Ala Gly Arg Pro Leu Ala Phe Ser Asp Ala Gly Pro
         20                  25                  30 cac gtt cac tac ggc tgg gga gac ccc atc cgg cag cgg tac ctc tac     144
His Val His Tyr Gly Trp Gly Asp Pro Ile Arg Gln Arg Tyr Leu Tyr
     35                  40                  45 aca gat gat gcc cag cag aca gaa gcc cac ctg gag atc agg gag gat     192
Thr Asp Asp Ala Gln Gln Thr Glu Ala His Leu Glu Ile Arg Glu Asp
 50                  55                  60 ggg acg gtg ggg ggc gct gct gac cag agc ccc gaa agt ctc ctg cag     240
Gly Thr Val Gly Gly Ala Ala Asp Gln Ser Pro Glu Ser Leu Leu Gln
 65                  70                  75                  80 ctg aaa gcc ttg aag ccg gga gtt att caa atc ttg gga gtc aag aca     288
Leu Lys Ala Leu Lys Pro Gly Val Ile Gln Ile Leu Gly Val Lys Thr
             85                  90                  95 tcc agg ttc ctg tgc cag cgg cca gat ggg gcc ctg tat gga tcg ctc     336
Ser Arg Phe Leu Cys Gln Arg Pro Asp Gly Ala Leu Tyr Gly Ser Leu
        100                 105                 110 cac ttt gac cct gag gcc tgc agc ttc cgg gag ctg ctt ctt gag gac     384
His Phe Asp Pro Glu Ala Cys Ser Phe Arg Glu Leu Leu Leu Glu Asp
        115                 120                 125 gga tac aat gtt tac cag tcc gaa gcc cac ggc ctc ccg ctg cac ctg     432
Gly Tyr Asn Val Tyr Gln Ser Glu Ala His Gly Leu Pro Leu His Leu
130                 135                 140 cca ggg aac aag tcc cca cac cgg gac cct gca ccc cga gga cca gct     480
Pro Gly Asn Lys Ser Pro His Arg Asp Pro Ala Pro Arg Gly Pro Ala
145                 150                 155                 160 cgc ttc ctg cca cta cca ggc ctg ccc ccc gca ccc ccg gag cca ccc     528
Arg Phe Leu Pro Leu Pro Gly Leu Pro Pro Ala Pro Pro Glu Pro Pro
                165                 170                 175 gga atc ctg gcc ccc cag ccc ccc gat gtg ggc tcc tcg gac cct ctg     576
Gly Ile Leu Ala Pro Gln Pro Pro Asp Val Gly Ser Ser Asp Pro Leu
            180                 185                 190 agc atg gtg gga cct tcc cag ggc cga agc ccc agc tac gct tcc tga     624
Ser Met Val Gly Pro Ser Gln Gly Arg Ser Pro Ser Tyr Ala Ser
        195                 200                 205
```

<210> SEQ ID NO 28
<211> LENGTH: 207
<212> TYPE: PRT
<213> ORGANISM: Artificial
<220> FEATURE:
<223> OTHER INFORMATION: Synthetic Construct

<400> SEQUENCE: 28

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Gln Arg Tyr Leu Tyr
        35                  40                  45

Thr Asp Asp Ala Gln Gln Thr Glu Ala His Leu Glu Ile Arg Glu Asp
 50                  55                  60

Gly Thr Val Gly Gly Ala Ala Asp Gln Ser Pro Glu Ser Leu Leu Gln
 65                  70                  75                  80

Leu Lys Ala Leu Lys Pro Gly Val Ile Gln Ile Leu Gly Val Lys Thr
             85                  90                  95

Ser Arg Phe Leu Cys Gln Arg Pro Asp Gly Ala Leu Tyr Gly Ser Leu
        100                 105                 110

His Phe Asp Pro Glu Ala Cys Ser Phe Arg Glu Leu Leu Leu Glu Asp
```

```
                     115                 120                 125
Gly Tyr Asn Val Tyr Gln Ser Glu Ala His Gly Leu Pro Leu His Leu
        130                 135                 140

Pro Gly Asn Lys Ser Pro His Arg Asp Pro Ala Pro Arg Gly Pro Ala
145                 150                 155                 160

Arg Phe Leu Pro Leu Pro Gly Leu Pro Pro Ala Pro Glu Pro Pro
                165                 170                 175

Gly Ile Leu Ala Pro Gln Pro Pro Asp Val Gly Ser Ser Asp Pro Leu
                180                 185                 190

Ser Met Val Gly Pro Ser Gln Gly Arg Ser Pro Ser Tyr Ala Ser
            195                 200                 205

<210> SEQ ID NO 29
<211> LENGTH: 618
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(618)

<400> SEQUENCE: 29 atg cgg agc ggg tgt gtg gtg gtc cac gta tgg atc ctg gcc ggc ctc      48
Met Arg Ser Gly Cys Val Val Val His Val Trp Ile Leu Ala Gly Leu
1               5                   10                  15 tgg ctg gcc gtg gcc ggg cgt cca ctt gct ttt tct gat gct ggt cca      96
Trp Leu Ala Val Ala Gly Arg Pro Leu Ala Phe Ser Asp Ala Gly Pro
            20                  25                  30 ctc ctg caa ttc ggg ggc caa gtc cgg cag cgg tac ctc tac aca gat     144
Leu Leu Gln Phe Gly Gly Gln Val Arg Gln Arg Tyr Leu Tyr Thr Asp
        35                  40                  45 gat gcc cag cag aca gaa gcc cac ctg gag atc agg gag gat ggg acg     192
Asp Ala Gln Gln Thr Glu Ala His Leu Glu Ile Arg Glu Asp Gly Thr
    50                  55                  60 gtg ggg ggc gct gct gac cag agc ccc gaa agt ctc ctg cag ctg aaa     240
Val Gly Gly Ala Ala Asp Gln Ser Pro Glu Ser Leu Leu Gln Leu Lys
65                  70                  75                  80 gcc ttg aag ccg gga gtt att caa atc ttg gga gtc aag aca tcc agg     288
Ala Leu Lys Pro Gly Val Ile Gln Ile Leu Gly Val Lys Thr Ser Arg
                85                  90                  95 ttc ctg tgc cag cgg cca gat ggg gcc ctg tat gga tcg ctc cac ttt     336
Phe Leu Cys Gln Arg Pro Asp Gly Ala Leu Tyr Gly Ser Leu His Phe
            100                 105                 110 gac cct gag gcc tgc agc ttc agg gag ctg ctt ctt gag gac gga tac     384
Asp Pro Glu Ala Cys Ser Phe Arg Glu Leu Leu Leu Glu Asp Gly Tyr
        115                 120                 125 aat gtt tac cag tcc gaa gcc cac ggc ctc ccg ctg cac ctg cca ggg     432
Asn Val Tyr Gln Ser Glu Ala His Gly Leu Pro Leu His Leu Pro Gly
    130                 135                 140 aac aag tcc cca cac cgg gac cct gca ccc gga cca gct cgc ttc         480
Asn Lys Ser Pro His Arg Asp Pro Ala Pro Arg Gly Pro Ala Arg Phe
145                 150                 155                 160 ctg cca cta cca ggc ctg ccc ccc gca ccc ccg gag cca ccc gga atc     528
Leu Pro Leu Pro Gly Leu Pro Pro Ala Pro Pro Glu Pro Pro Gly Ile
                165                 170                 175 ctg gcc ccc cag ccc ccc gat gtg ggc tcc tcg gac cct ctg agc atg     576
Leu Ala Pro Gln Pro Pro Asp Val Gly Ser Ser Asp Pro Leu Ser Met
            180                 185                 190 gtg gga cct tcc cag ggc cga agc ccc agc tac gct tcc tga             618
Val Gly Pro Ser Gln Gly Arg Ser Pro Ser Tyr Ala Ser
        195                 200                 205
```

<210> SEQ ID NO 30
<211> LENGTH: 205
<212> TYPE: PRT
<213> ORGANISM: Artificial
<220> FEATURE:
<223> OTHER INFORMATION: Synthetic Construct

<400> SEQUENCE: 30

```
Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

Leu Leu Gln Phe Gly Gly Gln Val Arg Gln Arg Tyr Leu Tyr Thr Asp
            35                  40                  45

Asp Ala Gln Gln Thr Glu Ala His Leu Glu Ile Arg Glu Asp Gly Thr
        50                  55                  60

Val Gly Gly Ala Ala Asp Gln Ser Pro Glu Ser Leu Leu Gln Leu Lys
65                  70                  75                  80

Ala Leu Lys Pro Gly Val Ile Gln Ile Leu Gly Val Lys Thr Ser Arg
                85                  90                  95

Phe Leu Cys Gln Arg Pro Asp Gly Ala Leu Tyr Gly Ser Leu His Phe
            100                 105                 110

Asp Pro Glu Ala Cys Ser Phe Arg Glu Leu Leu Leu Glu Asp Gly Tyr
        115                 120                 125

Asn Val Tyr Gln Ser Glu Ala His Gly Leu Pro Leu His Leu Pro Gly
    130                 135                 140

Asn Lys Ser Pro His Arg Asp Pro Ala Pro Arg Gly Pro Ala Arg Phe
145                 150                 155                 160

Leu Pro Leu Pro Gly Leu Pro Pro Ala Pro Pro Glu Pro Pro Gly Ile
                165                 170                 175

Leu Ala Pro Gln Pro Pro Asp Val Gly Ser Ser Asp Pro Leu Ser Met
            180                 185                 190

Val Gly Pro Ser Gln Gly Arg Ser Pro Ser Tyr Ala Ser
        195                 200                 205
```

<210> SEQ ID NO 31
<211> LENGTH: 636
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(636)

<400> SEQUENCE: 31

```
atg gac tcg gac gag acc ggg ttc gag cac tca gga ctg tgg gtt tct    48
Met Asp Ser Asp Glu Thr Gly Phe Glu His Ser Gly Leu Trp Val Ser
1               5                   10                  15 gtg ctg gct ggt ctt ctg ctg gga gcc tgc cag gca cat cca att cca    96
Val Leu Ala Gly Leu Leu Leu Gly Ala Cys Gln Ala His Pro Ile Pro
                20                  25                  30 gat tct tct cca tta tta caa ttc ggg tgg ggc gac ccc atc cgg cag    144
Asp Ser Ser Pro Leu Leu Gln Phe Gly Trp Gly Asp Pro Ile Arg Gln
            35                  40                  45 cgg tac ctc tac aca gat gat gcc cag cag aca gaa gcc cac ctg gag    192
Arg Tyr Leu Tyr Thr Asp Asp Ala Gln Gln Thr Glu Ala His Leu Glu
        50                  55                  60
```

```
atc agg gag gat ggg acg gtg ggg ggc gct gct gac cag agc ccc gaa      240
Ile Arg Glu Asp Gly Thr Val Gly Gly Ala Ala Asp Gln Ser Pro Glu
65              70                  75                  80 agt ctc ctg cag ctg aaa gcc ttg aag ccg gga gtt att caa atc ttg      288
Ser Leu Leu Gln Leu Lys Ala Leu Lys Pro Gly Val Ile Gln Ile Leu
            85                  90                  95 gga gtc aag aca tcc agg ttc ctg tgc cag cgg cca gat ggg gcc ctg      336
Gly Val Lys Thr Ser Arg Phe Leu Cys Gln Arg Pro Asp Gly Ala Leu
        100                 105                 110 tat gga tcg ctc cac ttt gac cct gag gcc tgc agc ttc cgg gag ctg      384
Tyr Gly Ser Leu His Phe Asp Pro Glu Ala Cys Ser Phe Arg Glu Leu
    115                 120                 125 ctt ctt gag gac gga tac aat gtt tac cag tcc gaa gcc cac ggc ctc      432
Leu Leu Glu Asp Gly Tyr Asn Val Tyr Gln Ser Glu Ala His Gly Leu
130                 135                 140 ccg ctg cac ctg cca ggg aac aag tcc cca cac cgg gac cct gca ccc      480
Pro Leu His Leu Pro Gly Asn Lys Ser Pro His Arg Asp Pro Ala Pro
145                 150                 155                 160 cga gga cca gct cgc ttc ctg cca cta cca ggc ctg ccc ccc gca ccc      528
Arg Gly Pro Ala Arg Phe Leu Pro Leu Pro Gly Leu Pro Pro Ala Pro
            165                 170                 175 ccg gag cca ccc gga atc ctg gcc ccc cag ccc ccc gat gtg ggc tcc      576
Pro Glu Pro Pro Gly Ile Leu Ala Pro Gln Pro Pro Asp Val Gly Ser
        180                 185                 190 tcg gac cct ctg agc atg gtg gga cct tcc cag ggc cga agc ccc agc      624
Ser Asp Pro Leu Ser Met Val Gly Pro Ser Gln Gly Arg Ser Pro Ser
    195                 200                 205 tac gct tcc tga                                                      636
Tyr Ala Ser
    210

<210> SEQ ID NO 32
<211> LENGTH: 211
<212> TYPE: PRT
<213> ORGANISM: Artificial
<220> FEATURE:
<223> OTHER INFORMATION: Synthetic Construct

<400> SEQUENCE: 32

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Trp Gly Asp Pro Ile Arg Gln
        35                  40                  45

Arg Tyr Leu Tyr Thr Asp Asp Ala Gln Gln Thr Glu Ala His Leu Glu
    50                  55                  60

Ile Arg Glu Asp Gly Thr Val Gly Gly Ala Ala Asp Gln Ser Pro Glu
65              70                  75                  80

Ser Leu Leu Gln Leu Lys Ala Leu Lys Pro Gly Val Ile Gln Ile Leu
            85                  90                  95

Gly Val Lys Thr Ser Arg Phe Leu Cys Gln Arg Pro Asp Gly Ala Leu
        100                 105                 110

Tyr Gly Ser Leu His Phe Asp Pro Glu Ala Cys Ser Phe Arg Glu Leu
    115                 120                 125

Leu Leu Glu Asp Gly Tyr Asn Val Tyr Gln Ser Glu Ala His Gly Leu
130                 135                 140

Pro Leu His Leu Pro Gly Asn Lys Ser Pro His Arg Asp Pro Ala Pro
145                 150                 155                 160
```

```
Arg Gly Pro Ala Arg Phe Leu Pro Leu Pro Gly Leu Pro Ala Pro
            165                 170                 175

Pro Glu Pro Pro Gly Ile Leu Ala Pro Gln Pro Pro Asp Val Gly Ser
        180                 185                 190

Ser Asp Pro Leu Ser Met Val Gly Pro Ser Gln Gly Arg Ser Pro Ser
        195                 200                 205

Tyr Ala Ser
    210

<210> SEQ ID NO 33
<211> LENGTH: 645
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(645)

<400> SEQUENCE: 33 atg cgg agc ggg tgt gtg gtg gtc cac gta tgg atc ctg gcc ggc ctc      48
Met Arg Ser Gly Cys Val Val Val His Val Trp Ile Leu Ala Gly Leu
1               5                   10                  15 tgg ctg gcc gtg gcc ggg cgt cca ctt gct ttt tct gat gct ggt cca      96
Trp Leu Ala Val Ala Gly Arg Pro Leu Ala Phe Ser Asp Ala Gly Pro
            20                  25                  30 cac gtt cac tac ggc ggc caa gtc cgc ctg cgg cac ctg tac acc tcc     144
His Val His Tyr Gly Gly Gln Val Arg Leu Arg His Leu Tyr Thr Ser
        35                  40                  45 ggc ccc cac ggg ctc tcc agc tgc ttc ctg cgc atc cgt gcc gac ggc     192
Gly Pro His Gly Leu Ser Ser Cys Phe Leu Arg Ile Arg Ala Asp Gly
    50                  55                  60 gtc gtg gac tgc gcg cgg ggc cag agc gcg cac agt ttg ctg gag atc     240
Val Val Asp Cys Ala Arg Gly Gln Ser Ala His Ser Leu Leu Glu Ile
65                  70                  75                  80 aag gca gtc gct ctg cgg acc gtg gcc atc aag ggc gtg cac agc gtg     288
Lys Ala Val Ala Leu Arg Thr Val Ala Ile Lys Gly Val His Ser Val
                85                  90                  95 cgg tac ctc tgc atg ggc gcc gac ggc aag atg cag ggg ctg ctt cag     336
Arg Tyr Leu Cys Met Gly Ala Asp Gly Lys Met Gln Gly Leu Leu Gln
            100                 105                 110 tac tcg gag gaa gac tgt gct ttc gag gag gag atc cgc cca gat ggc     384
Tyr Ser Glu Glu Asp Cys Ala Phe Glu Glu Glu Ile Arg Pro Asp Gly
        115                 120                 125 tac aat gtg tac cga tcc gag aag cac cgc ctc ccg gtc tcc ctg agc     432
Tyr Asn Val Tyr Arg Ser Glu Lys His Arg Leu Pro Val Ser Leu Ser
    130                 135                 140 agt gcc aaa cag cgg cag ctg tac aag aac aga ggc ttt ctt cca ctc     480
Ser Ala Lys Gln Arg Gln Leu Tyr Lys Asn Arg Gly Phe Leu Pro Leu
145                 150                 155                 160 tct cat ttc ctg ccc atg ctg ccc atg gtc cca gag gag cct gag gac     528
Ser His Phe Leu Pro Met Leu Pro Met Val Pro Glu Glu Pro Glu Asp
                165                 170                 175 ctc agg ggc cac ttg gaa tct gac atg ttc tct tcg ccc ctg gag acc     576
Leu Arg Gly His Leu Glu Ser Asp Met Phe Ser Ser Pro Leu Glu Thr
            180                 185                 190 gac agc atg gac cca ttt ggg ctt gtc acc gga ctg gag gcc gtg agg     624
Asp Ser Met Asp Pro Phe Gly Leu Val Thr Gly Leu Glu Ala Val Arg
        195                 200                 205 agt ccc agc ttt gag aag taa                                         645
Ser Pro Ser Phe Glu Lys
    210
```

-continued

```
<210> SEQ ID NO 34
<211> LENGTH: 214
<212> TYPE: PRT
<213> ORGANISM: Artificial
<220> FEATURE:
<223> OTHER INFORMATION: Synthetic Construct

<400> SEQUENCE: 34

Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Gly Gln Val Arg Leu Arg His Leu Tyr Thr Ser
        35                  40                  45

Gly Pro His Gly Leu Ser Ser Cys Phe Leu Arg Ile Arg Ala Asp Gly
    50                  55                  60

Val Val Asp Cys Ala Arg Gly Gln Ser Ala His Ser Leu Leu Glu Ile
65                  70                  75                  80

Lys Ala Val Ala Leu Arg Thr Val Ala Ile Lys Gly Val His Ser Val
                85                  90                  95

Arg Tyr Leu Cys Met Gly Ala Asp Gly Lys Met Gln Gly Leu Leu Gln
            100                 105                 110

Tyr Ser Glu Glu Asp Cys Ala Phe Glu Glu Ile Arg Pro Asp Gly
        115                 120                 125

Tyr Asn Val Tyr Arg Ser Glu Lys His Arg Leu Pro Val Ser Leu Ser
    130                 135                 140

Ser Ala Lys Gln Arg Gln Leu Tyr Lys Asn Arg Gly Phe Leu Pro Leu
145                 150                 155                 160

Ser His Phe Leu Pro Met Leu Pro Met Val Pro Glu Glu Pro Glu Asp
                165                 170                 175

Leu Arg Gly His Leu Glu Ser Asp Met Phe Ser Ser Pro Leu Glu Thr
            180                 185                 190

Asp Ser Met Asp Pro Phe Gly Leu Val Thr Gly Leu Glu Ala Val Arg
        195                 200                 205

Ser Pro Ser Phe Glu Lys
    210

<210> SEQ ID NO 35
<211> LENGTH: 648
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(648)

<400> SEQUENCE: 35 atg cgg agc ggg tgt gtg gtg gtc cac gta tgg atc ctg gcc ggc ctc     48
Met Arg Ser Gly Cys Val Val Val His Val Trp Ile Leu Ala Gly Leu
1               5                   10                  15 tgg ctg gcc gtg gcc ggg cgt cca ctt gct ttt tct gat gct ggt cca     96
Trp Leu Ala Val Ala Gly Arg Pro Leu Ala Phe Ser Asp Ala Gly Pro
            20                  25                  30 cac gtt cac tac ggc tgg ggc gac ccc atc cgc ctg cgg cac ctg tac    144
His Val His Tyr Gly Trp Gly Asp Pro Ile Arg Leu Arg His Leu Tyr
        35                  40                  45 acc gat gat gcc cag cag aca gaa tgc ttc ctg cgc atc cgt gcc gac    192
Thr Asp Asp Ala Gln Gln Thr Glu Cys Phe Leu Arg Ile Arg Ala Asp
```

```
                50                  55                  60
ggc gtc gtg gac tgc gcg cgg ggc cag agc gcg cac agt ttg ctg gag     240
Gly Val Val Asp Cys Ala Arg Gly Gln Ser Ala His Ser Leu Leu Glu
 65                  70                  75                  80 atc aag gca gtc gct ctg cgg acc gtg gcc atc aag ggc gtg cac agc     288
Ile Lys Ala Val Ala Leu Arg Thr Val Ala Ile Lys Gly Val His Ser
                 85                  90                  95 gtg cgg tac ctc tgc atg ggc gcc gac ggc aag atg cag ggg ctg ctt     336
Val Arg Tyr Leu Cys Met Gly Ala Asp Gly Lys Met Gln Gly Leu Leu
            100                 105                 110 cag tac tcg gag gaa gac tgt gct ttc gag gag gag atc cgc cca gat     384
Gln Tyr Ser Glu Glu Asp Cys Ala Phe Glu Glu Glu Ile Arg Pro Asp
        115                 120                 125 ggc tac aat gtg tac cga tcc gag aag cac cgc ctc ccg gtc tcc ctg     432
Gly Tyr Asn Val Tyr Arg Ser Glu Lys His Arg Leu Pro Val Ser Leu
    130                 135                 140 agc agt gcc aaa cag cgg cag ctg tac aag aac aga ggc ttt ctt cca     480
Ser Ser Ala Lys Gln Arg Gln Leu Tyr Lys Asn Arg Gly Phe Leu Pro
145                 150                 155                 160 ctc tct cat ttc ctg ccc atg ctg ccc atg gtc cca gag gag cct gag     528
Leu Ser His Phe Leu Pro Met Leu Pro Met Val Pro Glu Glu Pro Glu
                165                 170                 175 gac ctc agg ggc cac ttg gaa tct gac atg ttc tct tcg ccc ctg gag     576
Asp Leu Arg Gly His Leu Glu Ser Asp Met Phe Ser Ser Pro Leu Glu
            180                 185                 190 acc gac agc atg gac cca ttt ggg ctt gtc acc gga ctg gag gcc gtg     624
Thr Asp Ser Met Asp Pro Phe Gly Leu Val Thr Gly Leu Glu Ala Val
        195                 200                 205 agg agt ccc agc ttt gag aag taa                                     648
Arg Ser Pro Ser Phe Glu Lys
    210                 215

<210> SEQ ID NO 36
<211> LENGTH: 215
<212> TYPE: PRT
<213> ORGANISM: Artificial
<220> FEATURE:
<223> OTHER INFORMATION: Synthetic Construct

<400> SEQUENCE: 36

Met Arg Ser Gly Cys Val Val His Val Trp Ile Leu Ala Gly Leu
 1               5                  10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Asp Asp Ala Gln Gln Thr Glu Cys Phe Leu Arg Ile Arg Ala Asp
        50                  55                  60

Gly Val Val Asp Cys Ala Arg Gly Gln Ser Ala His Ser Leu Leu Glu
 65                  70                  75                  80

Ile Lys Ala Val Ala Leu Arg Thr Val Ala Ile Lys Gly Val His Ser
                 85                  90                  95

Val Arg Tyr Leu Cys Met Gly Ala Asp Gly Lys Met Gln Gly Leu Leu
            100                 105                 110

Gln Tyr Ser Glu Glu Asp Cys Ala Phe Glu Glu Glu Ile Arg Pro Asp
        115                 120                 125

Gly Tyr Asn Val Tyr Arg Ser Glu Lys His Arg Leu Pro Val Ser Leu
    130                 135                 140

Ser Ser Ala Lys Gln Arg Gln Leu Tyr Lys Asn Arg Gly Phe Leu Pro
```

```
                145                 150                 155                 160
Leu Ser His Phe Leu Pro Met Leu Pro Met Val Pro Glu Glu Pro Glu
                    165                 170                 175

Asp Leu Arg Gly His Leu Glu Ser Asp Met Phe Ser Ser Pro Leu Glu
                180                 185                 190

Thr Asp Ser Met Asp Pro Phe Gly Leu Val Thr Gly Leu Glu Ala Val
            195                 200                 205

Arg Ser Pro Ser Phe Glu Lys
        210                 215

<210> SEQ ID NO 37
<211> LENGTH: 645
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(645)

<400> SEQUENCE: 37 atg cgg agc ggg tgt gtg gtg gtc cac gta tgg atc ctg gcc ggc ctc      48
Met Arg Ser Gly Cys Val Val Val His Val Trp Ile Leu Ala Gly Leu
1               5                   10                  15 tgg ctg gcc gtg gcc ggg cgt cca ctt gct ttt tct gat gct ggt cca      96
Trp Leu Ala Val Ala Gly Arg Pro Leu Ala Phe Ser Asp Ala Gly Pro
            20                  25                  30 cac gtt cac tac ggc tgg ggc gac ccc atc cgc ctg cgg cac ctg tac     144
His Val His Tyr Gly Trp Gly Asp Pro Ile Arg Leu Arg His Leu Tyr
        35                  40                  45 acc tcc ggc ccc cac ggg ctc tcc agc tgc ttc ctg cgc atc cgt gcc     192
Thr Ser Gly Pro His Gly Leu Ser Ser Cys Phe Leu Arg Ile Arg Ala
    50                  55                  60 gac ggc gtc gtg gac tgc gcg cgg ggc cag agc gcg cac agt ttg ctg     240
Asp Gly Val Val Asp Cys Ala Arg Gly Gln Ser Ala His Ser Leu Leu
65                  70                  75                  80 gag atc aag gca gtc gct ctg cgg acc gtg gcc atc aag ggc gtg cac     288
Glu Ile Lys Ala Val Ala Leu Arg Thr Val Ala Ile Lys Gly Val His
                85                  90                  95 agc gtg cgg tac ctc tgc atg ggc gcc gac ggc aag atg cag ggg ctg     336
Ser Val Arg Tyr Leu Cys Met Gly Ala Asp Gly Lys Met Gln Gly Leu
            100                 105                 110 ctt cag tac tcg gag gaa gac tgt gct ttc gag gag gag atc cgc cca     384
Leu Gln Tyr Ser Glu Glu Asp Cys Ala Phe Glu Glu Glu Ile Arg Pro
        115                 120                 125 gat ggc tac aat gtg tac cga tcc gag aag cac cgc ctc ccg gtc tcc     432
Asp Gly Tyr Asn Val Tyr Arg Ser Glu Lys His Arg Leu Pro Val Ser
    130                 135                 140 ctg cca ggg aac aag tcc cca cac cgg gac cct gca ccc cga gga cca     480
Leu Pro Gly Asn Lys Ser Pro His Arg Asp Pro Ala Pro Arg Gly Pro
145                 150                 155                 160 tct cat ttc ctg ccc atg ctg ccc atg gtc cca gag gag cct gag gac     528
Ser His Phe Leu Pro Met Leu Pro Met Val Pro Glu Glu Pro Glu Asp
                165                 170                 175 ctc agg ggc cac ttg gaa tct gac atg ttc tct tcg ccc ctg gag acc     576
Leu Arg Gly His Leu Glu Ser Asp Met Phe Ser Ser Pro Leu Glu Thr
            180                 185                 190 gac agc atg gac cca ttt ggg ctt gtc acc gga ctg gag gcc gtg agg     624
Asp Ser Met Asp Pro Phe Gly Leu Val Thr Gly Leu Glu Ala Val Arg
        195                 200                 205 agt ccc agc ttt gag aag taa                                         645
```

Ser Pro Ser Phe Glu Lys
    210

<210> SEQ ID NO 38
<211> LENGTH: 214
<212> TYPE: PRT
<213> ORGANISM: Artificial
<220> FEATURE:
<223> OTHER INFORMATION: Synthetic Construct

<400> SEQUENCE: 38

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Pro Gly Asn Lys Ser Pro His Arg Asp Pro Ala Pro Arg Gly Pro
145                 150                 155                 160

Ser His Phe Leu Pro Met Leu Pro Met Val Pro Glu Glu Pro Glu Asp
                165                 170                 175

Leu Arg Gly His Leu Glu Ser Asp Met Phe Ser Ser Pro Leu Glu Thr
            180                 185                 190

Asp Ser Met Asp Pro Phe Gly Leu Val Thr Gly Leu Glu Ala Val Arg
        195                 200                 205

Ser Pro Ser Phe Glu Lys
    210

<210> SEQ ID NO 39
<211> LENGTH: 642
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(642)

<400> SEQUENCE: 39

```
atg cgg agc ggg tgt gtg gtg gtc cac gta tgg atc ctg gcc ggc ctc      48
Met Arg Ser Gly Cys Val Val Val His Val Trp Ile Leu Ala Gly Leu
1               5                   10                  15 tgg ctg gcc gtg gcc ggg cgt cca ctt gct ttt tct gat gct ggt cca      96
Trp Leu Ala Val Ala Gly Arg Pro Leu Ala Phe Ser Asp Ala Gly Pro
            20                  25                  30 cac gtt cac tac ggc tgg ggc gac ccc atc cgc ctg cgg cac ctg tac     144
His Val His Tyr Gly Trp Gly Asp Pro Ile Arg Leu Arg His Leu Tyr
        35                  40                  45
```

```
acc gat gat gcc cag cag aca gaa tgc ttc ctg cgc atc cgt gcc gac    192
Thr Asp Asp Ala Gln Gln Thr Glu Cys Phe Leu Arg Ile Arg Ala Asp
 50                  55                  60 ggc gtc gtg gac tgc gcg cgg ggc cag agc gcg cac agt ttg ctg gag    240
Gly Val Val Asp Cys Ala Arg Gly Gln Ser Ala His Ser Leu Leu Glu
 65                  70                  75                  80 atc aag gca gtc gct ctg cgg acc gtg gcc atc aag ggc gtg cac agc    288
Ile Lys Ala Val Ala Leu Arg Thr Val Ala Ile Lys Gly Val His Ser
                 85                  90                  95 gtg cgg tac ctc tgc atg ggc gcc gac ggc aag atg cag ggg ctg ctt    336
Val Arg Tyr Leu Cys Met Gly Ala Asp Gly Lys Met Gln Gly Leu Leu
            100                 105                 110 cag tac tcg gag gaa gac tgt gct ttc gag gag gag atc cgc cca gat    384
Gln Tyr Ser Glu Glu Asp Cys Ala Phe Glu Glu Glu Ile Arg Pro Asp
        115                 120                 125 ggc tac aat gtg tac cga tcc gag aag cac cgc ctc ccg gtc tcc ctg    432
Gly Tyr Asn Val Tyr Arg Ser Glu Lys His Arg Leu Pro Val Ser Leu
130                 135                 140 cca ggg aac aag tcc cca cac cgg gac cct gca ccc cga gga cca tct    480
Pro Gly Asn Lys Ser Pro His Arg Asp Pro Ala Pro Arg Gly Pro Ser
145                 150                 155                 160 cat ttc ctg ccc atg ctg ccc atg gtc cca gag gag cct gag gac ctc    528
His Phe Leu Pro Met Leu Pro Met Val Pro Glu Glu Pro Glu Asp Leu
                165                 170                 175 agg ggc cac ttg gaa tct gac atg ttc tct tcg ccc ctg gag acc gac    576
Arg Gly His Leu Glu Ser Asp Met Phe Ser Ser Pro Leu Glu Thr Asp
            180                 185                 190 agc atg gac cca ttt ggg ctt gtc acc gga ctg gag gcc gtg agg agt    624
Ser Met Asp Pro Phe Gly Leu Val Thr Gly Leu Glu Ala Val Arg Ser
        195                 200                 205 ccc agc ttt gag aag taa                                            642
Pro Ser Phe Glu Lys
    210

<210> SEQ ID NO 40
<211> LENGTH: 213
<212> TYPE: PRT
<213> ORGANISM: Artificial
<220> FEATURE:
<223> OTHER INFORMATION: Synthetic Construct

<400> SEQUENCE: 40

Met Arg Ser Gly Cys Val Val His Val Trp Ile Leu Ala Gly Leu
  1               5                  10                  15

Trp Leu Ala Val Ala Gly Arg Pro Leu Ala Phe Ser Asp Ala Gly Pro
                 20                  25                  30

His Val His Tyr Gly Trp Gly Asp Pro Ile Arg Leu Arg His Leu Tyr
             35                  40                  45

Thr Asp Asp Ala Gln Gln Thr Glu Cys Phe Leu Arg Ile Arg Ala Asp
 50                  55                  60

Gly Val Val Asp Cys Ala Arg Gly Gln Ser Ala His Ser Leu Leu Glu
 65                  70                  75                  80

Ile Lys Ala Val Ala Leu Arg Thr Val Ala Ile Lys Gly Val His Ser
                 85                  90                  95

Val Arg Tyr Leu Cys Met Gly Ala Asp Gly Lys Met Gln Gly Leu Leu
            100                 105                 110

Gln Tyr Ser Glu Glu Asp Cys Ala Phe Glu Glu Glu Ile Arg Pro Asp
        115                 120                 125

Gly Tyr Asn Val Tyr Arg Ser Glu Lys His Arg Leu Pro Val Ser Leu
130                 135                 140
```

```
Pro Gly Asn Lys Ser Pro His Arg Asp Pro Ala Pro Arg Gly Pro Ser
145                 150                 155                 160

His Phe Leu Pro Met Leu Pro Met Val Pro Glu Glu Pro Glu Asp Leu
                165                 170                 175

Arg Gly His Leu Glu Ser Asp Met Phe Ser Ser Pro Leu Glu Thr Asp
            180                 185                 190

Ser Met Asp Pro Phe Gly Leu Val Thr Gly Leu Glu Ala Val Arg Ser
        195                 200                 205

Pro Ser Phe Glu Lys
    210

<210> SEQ ID NO 41
<211> LENGTH: 642
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(642)

<400> SEQUENCE: 41
```

| | | | | | | | | | | | | | | | | |
|---|---|---|---|---|---|---|---|---|---|---|---|---|---|---|---|---|
| atg | cgg | agc | ggg | tgt | gtg | gtc | cac | gta | tgg | atc | ctg | gcc | ggc | ctc | | 48 |
| Met | Arg | Ser | Gly | Cys | Val | Val | His | Val | Trp | Ile | Leu | Ala | Gly | Leu | | |
| 1 | | | | 5 | | | | | 10 | | | | | 15 | | |
| tgg | ctg | gcc | gtg | gcc | ggg | cgt | cca | ctt | gct | ttt | tct | gat | gct | ggt | cca | 96 |
| Trp | Leu | Ala | Val | Ala | Gly | Arg | Pro | Leu | Ala | Phe | Ser | Asp | Ala | Gly | Pro | |
| | | | 20 | | | | | 25 | | | | | 30 | | | |
| cac | gtt | cac | tac | ggc | ggc | caa | gtc | cgc | ctg | cgg | cac | ctg | tac | acc | gat | 144 |
| His | Val | His | Tyr | Gly | Gly | Gln | Val | Arg | Leu | Arg | His | Leu | Tyr | Thr | Asp | |
| | | 35 | | | | | 40 | | | | | 45 | | | | |
| gat | gcc | cag | cag | aca | gaa | tgc | ttc | ctg | cgc | atc | cgt | gcc | gac | ggc | gtc | 192 |
| Asp | Ala | Gln | Gln | Thr | Glu | Cys | Phe | Leu | Arg | Ile | Arg | Ala | Asp | Gly | Val | |
| | 50 | | | | | 55 | | | | | 60 | | | | | |
| gtg | gac | tgc | gcg | cgg | ggc | cag | agc | gcg | cac | agt | ttg | ctg | gag | atc | aag | 240 |
| Val | Asp | Cys | Ala | Arg | Gly | Gln | Ser | Ala | His | Ser | Leu | Leu | Glu | Ile | Lys | |
| 65 | | | | | 70 | | | | | 75 | | | | | 80 | |
| gca | gtc | gct | ctg | cgg | acc | gtg | gcc | atc | aag | ggc | gtg | cac | agc | gtg | cgg | 288 |
| Ala | Val | Ala | Leu | Arg | Thr | Val | Ala | Ile | Lys | Gly | Val | His | Ser | Val | Arg | |
| | | | | 85 | | | | | 90 | | | | | 95 | | |
| tac | ctc | tgc | atg | ggc | gcc | gac | ggc | aag | atg | cag | ggg | ctg | ctt | cag | tac | 336 |
| Tyr | Leu | Cys | Met | Gly | Ala | Asp | Gly | Lys | Met | Gln | Gly | Leu | Leu | Gln | Tyr | |
| | | | 100 | | | | | 105 | | | | | 110 | | | |
| tcg | gag | gaa | gac | tgt | gct | ttc | gag | gag | gag | atc | cgc | cca | gat | ggc | tac | 384 |
| Ser | Glu | Glu | Asp | Cys | Ala | Phe | Glu | Glu | Glu | Ile | Arg | Pro | Asp | Gly | Tyr | |
| | | 115 | | | | | 120 | | | | | 125 | | | | |
| aat | gtg | tac | cga | tcc | gag | aag | cac | cgc | ctc | ccg | gtc | tcc | ctg | agc | agt | 432 |
| Asn | Val | Tyr | Arg | Ser | Glu | Lys | His | Arg | Leu | Pro | Val | Ser | Leu | Ser | Ser | |
| | 130 | | | | | 135 | | | | | 140 | | | | | |
| gcc | aaa | cag | cgg | cag | ctg | tac | aag | aac | aga | ggc | ttt | ctt | cca | ctc | tct | 480 |
| Ala | Lys | Gln | Arg | Gln | Leu | Tyr | Lys | Asn | Arg | Gly | Phe | Leu | Pro | Leu | Ser | |
| 145 | | | | | 150 | | | | | 155 | | | | | 160 | |
| cat | ttc | ctg | ccc | atg | ctg | ccc | atg | gtc | cca | gag | gag | cct | gag | gac | ctc | 528 |
| His | Phe | Leu | Pro | Met | Leu | Pro | Met | Val | Pro | Glu | Glu | Pro | Glu | Asp | Leu | |
| | | | | 165 | | | | | 170 | | | | | 175 | | |
| agg | ggc | cac | ttg | gaa | tct | gac | atg | ttc | tct | tcg | ccc | ctg | gag | acc | gac | 576 |
| Arg | Gly | His | Leu | Glu | Ser | Asp | Met | Phe | Ser | Ser | Pro | Leu | Glu | Thr | Asp | |
| | | | 180 | | | | | 185 | | | | | 190 | | | |
| agc | atg | gac | cca | ttt | ggg | ctt | gtc | acc | gga | ctg | gag | gcc | gtg | agg | agt | 624 |
| Ser | Met | Asp | Pro | Phe | Gly | Leu | Val | Thr | Gly | Leu | Glu | Ala | Val | Arg | Ser | |
| | | 195 | | | | | 200 | | | | | 205 | | | | |

-continued

```
ccc agc ttt gag aag taa                                              642
Pro Ser Phe Glu Lys
    210

<210> SEQ ID NO 42
<211> LENGTH: 213
<212> TYPE: PRT
<213> ORGANISM: Artificial
<220> FEATURE:
<223> OTHER INFORMATION: Synthetic Construct

<400> SEQUENCE: 42

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Gly Gln Val Arg Leu Arg His Leu Tyr Thr Asp
        35                  40                  45

Asp Ala Gln Gln Thr Glu Cys Phe Leu Arg Ile Arg Ala Asp Gly Val
    50                  55                  60

Val Asp Cys Ala Arg Gly Gln Ser Ala His Ser Leu Leu Glu Ile Lys
65                  70                  75                  80

Ala Val Ala Leu Arg Thr Val Ala Ile Lys Gly Val His Ser Val Arg
                85                  90                  95

Tyr Leu Cys Met Gly Ala Asp Gly Lys Met Gln Gly Leu Leu Gln Tyr
            100                 105                 110

Ser Glu Glu Asp Cys Ala Phe Glu Glu Ile Arg Pro Asp Gly Tyr
            115                 120                 125

Asn Val Tyr Arg Ser Glu Lys His Arg Leu Pro Val Ser Leu Ser Ser
130                 135                 140

Ala Lys Gln Arg Gln Leu Tyr Lys Asn Arg Gly Phe Leu Pro Leu Ser
145                 150                 155                 160

His Phe Leu Pro Met Leu Pro Met Val Pro Glu Pro Glu Asp Leu
                165                 170                 175

Arg Gly His Leu Glu Ser Asp Met Phe Ser Ser Pro Leu Glu Thr Asp
            180                 185                 190

Ser Met Asp Pro Phe Gly Leu Val Thr Gly Leu Glu Ala Val Arg Ser
            195                 200                 205

Pro Ser Phe Glu Lys
    210

<210> SEQ ID NO 43
<211> LENGTH: 639
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(639)

<400> SEQUENCE: 43 atg cgg agc ggg tgt gtg gtg gtc cac gta tgg atc ctg gcc ggc ctc    48
Met Arg Ser Gly Cys Val Val His Val Trp Ile Leu Ala Gly Leu
1               5                   10                  15 tgg ctg gcc gtg gcc ggg cgt cca ctt gct ttt tct gat gct ggt cca    96
Trp Leu Ala Val Ala Gly Arg Pro Leu Ala Phe Ser Asp Ala Gly Pro
            20                  25                  30 cac gtt cac tac ggc ggc caa gtc cgc ctg cgg cac ctg tac acc tcc   144
His Val His Tyr Gly Gly Gln Val Arg Leu Arg His Leu Tyr Thr Ser
```

```
                  35                  40                  45
ggc ccc cac ggg ctc tcc agc tgc ttc ctg cgc atc cgt gcc gac ggc    192
Gly Pro His Gly Leu Ser Ser Cys Phe Leu Arg Ile Arg Ala Asp Gly
         50                  55                  60 gtc gtg gac tgc gcg cgg ggc cag agc gcg cac agt ttg ctg gag atc    240
Val Val Asp Cys Ala Arg Gly Gln Ser Ala His Ser Leu Leu Glu Ile
 65                  70                  75                  80 aag gca gtc gct ctg cgg acc gtg gcc atc aag ggc gtg cac agc gtg    288
Lys Ala Val Ala Leu Arg Thr Val Ala Ile Lys Gly Val His Ser Val
                 85                  90                  95 cgg tac ctc tgc atg ggc gcc gac ggc aag atg cag ggg ctg ctt cag    336
Arg Tyr Leu Cys Met Gly Ala Asp Gly Lys Met Gln Gly Leu Leu Gln
            100                 105                 110 tac tcg gag gaa gac tgt gct ttc gag gag gag atc cgc cca gat ggc    384
Tyr Ser Glu Glu Asp Cys Ala Phe Glu Glu Glu Ile Arg Pro Asp Gly
        115                 120                 125 tac aat gtg tac cga tcc gag aag cac cgc ctc ccg gtc tcc ctg cca    432
Tyr Asn Val Tyr Arg Ser Glu Lys His Arg Leu Pro Val Ser Leu Pro
    130                 135                 140 ggg aac aag tcc cca cac cgg gac cct gca ccc cga gga cca tct cat    480
Gly Asn Lys Ser Pro His Arg Asp Pro Ala Pro Arg Gly Pro Ser His
145                 150                 155                 160 ttc ctg ccc atg ctg ccc atg gtc cca gag gag cct gag gac ctc agg    528
Phe Leu Pro Met Leu Pro Met Val Pro Glu Glu Pro Glu Asp Leu Arg
                165                 170                 175 ggc cac ttg gaa tct gac atg ttc tct tcg ccc ctg gag acc gac agc    576
Gly His Leu Glu Ser Asp Met Phe Ser Ser Pro Leu Glu Thr Asp Ser
            180                 185                 190 atg gac cca ttt ggg ctt gtc acc gga ctg gag gcc gtg agg agt ccc    624
Met Asp Pro Phe Gly Leu Val Thr Gly Leu Glu Ala Val Arg Ser Pro
        195                 200                 205 agc ttt gag aag taa                                                639
Ser Phe Glu Lys
    210
```

<210> SEQ ID NO 44
<211> LENGTH: 212
<212> TYPE: PRT
<213> ORGANISM: Artificial
<220> FEATURE:
<223> OTHER INFORMATION: Synthetic Construct

<400> SEQUENCE: 44

```
Met Arg Ser Gly Cys Val Val His Val Trp Ile Leu Ala Gly Leu
 1               5                  10                  15

Trp Leu Ala Val Ala Gly Arg Pro Leu Ala Phe Ser Asp Ala Gly Pro
                 20                  25                  30

His Val His Tyr Gly Gly Gln Val Arg Leu Arg His Leu Tyr Thr Ser
             35                  40                  45

Gly Pro His Gly Leu Ser Ser Cys Phe Leu Arg Ile Arg Ala Asp Gly
         50                  55                  60

Val Val Asp Cys Ala Arg Gly Gln Ser Ala His Ser Leu Leu Glu Ile
 65                  70                  75                  80

Lys Ala Val Ala Leu Arg Thr Val Ala Ile Lys Gly Val His Ser Val
                 85                  90                  95

Arg Tyr Leu Cys Met Gly Ala Asp Gly Lys Met Gln Gly Leu Leu Gln
            100                 105                 110

Tyr Ser Glu Glu Asp Cys Ala Phe Glu Glu Glu Ile Arg Pro Asp Gly
        115                 120                 125
```

```
Tyr Asn Val Tyr Arg Ser Glu Lys His Arg Leu Pro Val Ser Leu Pro
            130                 135                 140

Gly Asn Lys Ser Pro His Arg Asp Pro Ala Pro Arg Gly Pro Ser His
145                 150                 155                 160

Phe Leu Pro Met Leu Pro Met Val Pro Glu Glu Pro Glu Asp Leu Arg
                165                 170                 175

Gly His Leu Glu Ser Asp Met Phe Ser Ser Pro Leu Glu Thr Asp Ser
            180                 185                 190

Met Asp Pro Phe Gly Leu Val Thr Gly Leu Glu Ala Val Arg Ser Pro
        195                 200                 205

Ser Phe Glu Lys
    210

<210> SEQ ID NO 45
<211> LENGTH: 636
<212> TYPE: DNA
<213> ORGANISM: Artificial
<220> FEATURE:
<223> OTHER INFORMATION: chimeric fusion protein
<220> FEATURE:
<221> NAME/KEY: CDS
<222> LOCATION: (1)..(636)

<400> SEQUENCE: 45 atg cgg agc ggg tgt gtg gtc cac gta tgg atc ctg gcc ggc ctc         48
Met Arg Ser Gly Cys Val Val Val His Val Trp Ile Leu Ala Gly Leu
1               5                   10                  15 tgg ctg gcc gtg gcc ggg cgt cca ctt gct ttt tct gat gct ggt cca     96
Trp Leu Ala Val Ala Gly Arg Pro Leu Ala Phe Ser Asp Ala Gly Pro
            20                  25                  30 cac gtt cac tac ggc ggc caa gtc cgc ctg cgg cac ctg tac acc gat    144
His Val His Tyr Gly Gly Gln Val Arg Leu Arg His Leu Tyr Thr Asp
        35                  40                  45 gat gcc cag cag aca gaa tgc ttc ctg cgc atc cgt gcc gac ggc gtc    192
Asp Ala Gln Gln Thr Glu Cys Phe Leu Arg Ile Arg Ala Asp Gly Val
    50                  55                  60 gtg gac tgc gcg cgg ggc cag agc gcg cac agt ttg ctg gag atc aag    240
Val Asp Cys Ala Arg Gly Gln Ser Ala His Ser Leu Leu Glu Ile Lys
65                  70                  75                  80 gca gtc gct ctg cgg acc gtg gcc atc aag ggc gtg cac agc gtg cgg    288
Ala Val Ala Leu Arg Thr Val Ala Ile Lys Gly Val His Ser Val Arg
                85                  90                  95 tac ctc tgc atg ggc gcc gac ggc aag atg cag ggg ctg ctt cag tac    336
Tyr Leu Cys Met Gly Ala Asp Gly Lys Met Gln Gly Leu Leu Gln Tyr
            100                 105                 110 tcg gag gaa gac tgt gct ttc gag gag gag atc gcg cca gat ggc tac    384
Ser Glu Glu Asp Cys Ala Phe Glu Glu Glu Ile Arg Pro Asp Gly Tyr
        115                 120                 125 aat gtg tac cga tcc gag aag cac cgc ctc ccg gtc tcc ctg cca ggg    432
Asn Val Tyr Arg Ser Glu Lys His Arg Leu Pro Val Ser Leu Pro Gly
    130                 135                 140 aac aag tcc cca cac cgg gac cct gca ccc cga gga cca tct cat ttc    480
Asn Lys Ser Pro His Arg Asp Pro Ala Pro Arg Gly Pro Ser His Phe
145                 150                 155                 160 ctg ccc atg ctg ccc atg gtc cca gag gag cct gag gac ctc agg ggc    528
Leu Pro Met Leu Pro Met Val Pro Glu Glu Pro Glu Asp Leu Arg Gly
                165                 170                 175 cac ttg gaa tct gac atg ttc tct tcg ccc ctg gag acc gac agc atg    576
His Leu Glu Ser Asp Met Phe Ser Ser Pro Leu Glu Thr Asp Ser Met
            180                 185                 190 gac cca ttt ggg ctt gtc acc gga ctg gag gcc gtg agg agt ccc agc    624
```

```
Asp Pro Phe Gly Leu Val Thr Gly Leu Glu Ala Val Arg Ser Pro Ser
        195                 200                 205 ttt gag aag taa                                                        636
Phe Glu Lys
    210

<210> SEQ ID NO 46
<211> LENGTH: 211
<212> TYPE: PRT
<213> ORGANISM: Artificial
<220> FEATURE:
<223> OTHER INFORMATION: Synthetic Construct

<400> SEQUENCE: 46

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Gly Gln Val Arg Leu Arg His Leu Tyr Thr Asp
            35                  40                  45

Asp Ala Gln Gln Thr Glu Cys Phe Leu Arg Ile Arg Ala Asp Gly Val
        50                  55                  60

Val Asp Cys Ala Arg Gly Gln Ser Ala His Ser Leu Leu Glu Ile Lys
65                  70                  75                  80

Ala Val Ala Leu Arg Thr Val Ala Ile Lys Gly Val His Ser Val Arg
                85                  90                  95

Tyr Leu Cys Met Gly Ala Asp Gly Lys Met Gln Gly Leu Leu Gln Tyr
            100                 105                 110

Ser Glu Glu Asp Cys Ala Phe Glu Glu Ile Arg Pro Asp Gly Tyr
        115                 120                 125

Asn Val Tyr Arg Ser Glu Lys His Arg Leu Pro Val Ser Leu Pro Gly
130                 135                 140

Asn Lys Ser Pro His Arg Asp Pro Ala Pro Arg Gly Pro Ser His Phe
145                 150                 155                 160

Leu Pro Met Leu Pro Met Val Pro Glu Glu Pro Glu Asp Leu Arg Gly
                165                 170                 175

His Leu Glu Ser Asp Met Phe Ser Ser Pro Leu Glu Thr Asp Ser Met
            180                 185                 190

Asp Pro Phe Gly Leu Val Thr Gly Leu Glu Ala Val Arg Ser Pro Ser
        195                 200                 205

Phe Glu Lys
    210

<210> SEQ ID NO 47
<211> LENGTH: 21
<212> TYPE: PRT
<213> ORGANISM: Homo sapiens

<400> SEQUENCE: 47

Asp Ala Gly Pro His Val His Tyr Gly Trp Gly Asp Pro Ile Arg Leu
1               5                   10                  15

Arg His Leu Tyr Thr
            20

<210> SEQ ID NO 48
<211> LENGTH: 19
<212> TYPE: PRT
<213> ORGANISM: Homo sapiens

<400> SEQUENCE: 48
```

Asp Ser Ser Pro Leu Leu Gln Phe Gly Gly Gln Val Arg Gln Arg Tyr
1               5                   10                  15

Leu Tyr Thr

<210> SEQ ID NO 49
<211> LENGTH: 5
<212> TYPE: PRT
<213> ORGANISM: Homo sapiens

<400> SEQUENCE: 49

Trp Gly Asp Pro Ile
1               5

<210> SEQ ID NO 50
<211> LENGTH: 18
<212> TYPE: PRT
<213> ORGANISM: Homo sapiens

<400> SEQUENCE: 50

Asn Ala Ser Pro Leu Leu Gly Ser Ser Trp Gly Gly Leu Ile His Leu
1               5                   10                  15

Tyr Thr

<210> SEQ ID NO 51
<211> LENGTH: 14
<212> TYPE: PRT
<213> ORGANISM: Homo sapiens

<400> SEQUENCE: 51

Leu Tyr Thr Ser Gly Pro His Gly Leu Ser Ser Cys Phe Leu
1               5                   10

<210> SEQ ID NO 52
<211> LENGTH: 8
<212> TYPE: PRT
<213> ORGANISM: Homo sapiens

<400> SEQUENCE: 52

Ser Gly Pro His Gly Leu Ser Ser
1               5

<210> SEQ ID NO 53
<211> LENGTH: 13
<212> TYPE: PRT
<213> ORGANISM: Homo sapiens

<400> SEQUENCE: 53

Leu Tyr Thr Asp Asp Ala Gln Gln Thr Glu Ala His Leu
1               5                   10

<210> SEQ ID NO 54
<211> LENGTH: 7
<212> TYPE: PRT
<213> ORGANISM: Homo sapiens

<400> SEQUENCE: 54

Asp Asp Ala Gln Gln Thr Glu
1               5

<210> SEQ ID NO 55
<211> LENGTH: 12
<212> TYPE: PRT
<213> ORGANISM: Homo sapiens

```
<400> SEQUENCE: 55

Leu Tyr Thr Ala Thr Ala Arg Asn Ser Tyr His Leu
1               5                   10

<210> SEQ ID NO 56
<211> LENGTH: 6
<212> TYPE: PRT
<213> ORGANISM: Homo sapiens

<400> SEQUENCE: 56

Ala Thr Ala Arg Asn Ser
1               5

<210> SEQ ID NO 57
<211> LENGTH: 26
<212> TYPE: PRT
<213> ORGANISM: Homo sapiens

<400> SEQUENCE: 57

Leu Pro Leu His Leu Pro Gly Asn Lys Ser Pro His Arg Asp Pro Ala
1               5                   10                  15

Pro Arg Gly Pro Ala Arg Phe Leu Pro Leu
            20                  25

<210> SEQ ID NO 58
<211> LENGTH: 17
<212> TYPE: PRT
<213> ORGANISM: Homo sapiens

<400> SEQUENCE: 58

Ser Ser Ala Lys Gln Arg Gln Leu Tyr Lys Asn Arg Gly Phe Leu Pro
1               5                   10                  15

Leu

<210> SEQ ID NO 59
<211> LENGTH: 28
<212> TYPE: PRT
<213> ORGANISM: Homo sapiens

<400> SEQUENCE: 59

Leu Pro Val Ser Leu Ser Ser Ala Lys Gln Arg Gln Leu Tyr Lys Asn
1               5                   10                  15

Arg Gly Phe Leu Pro Leu Ser His Phe Leu Pro Met
            20                  25

<210> SEQ ID NO 60
<211> LENGTH: 15
<212> TYPE: PRT
<213> ORGANISM: Homo sapiens

<400> SEQUENCE: 60

Pro Gly Asn Lys Ser Pro His Arg Asp Pro Ala Pro Arg Gly Pro
1               5                   10                  15

<210> SEQ ID NO 61
<211> LENGTH: 27
<212> TYPE: PRT
<213> ORGANISM: Homo sapiens

<400> SEQUENCE: 61

Phe Leu Val Ser Leu Gly Arg Ala Lys Arg Ala Phe Leu Pro Gly Met
1               5                   10                  15

Asn Pro Pro Pro Tyr Ser Gln Phe Leu Ser Arg
```

```
                    20                  25

<210> SEQ ID NO 62
<211> LENGTH: 16
<212> TYPE: PRT
<213> ORGANISM: Homo sapiens

<400> SEQUENCE: 62

Gly Arg Ala Lys Arg Ala Phe Leu Pro Gly Met Asn Pro Pro Pro Tyr
1               5                   10                  15

<210> SEQ ID NO 63
<211> LENGTH: 4
<212> TYPE: PRT
<213> ORGANISM: Artificial Sequence
<220> FEATURE:
<223> OTHER INFORMATION: linker peptide

<400> SEQUENCE: 63

Gly Gly Gly Gly
1

<210> SEQ ID NO 64
<211> LENGTH: 5
<212> TYPE: PRT
<213> ORGANISM: Artificial Sequence
<220> FEATURE:
<223> OTHER INFORMATION: peptide linker

<400> SEQUENCE: 64

Gly Gly Gly Gly Gly
1               5

<210> SEQ ID NO 65
<211> LENGTH: 15
<212> TYPE: PRT
<213> ORGANISM: Artificial Sequence
<220> FEATURE:
<223> OTHER INFORMATION: peptide linker

<400> SEQUENCE: 65

Gly Gly Gly Gly Gly Ser Gly Gly Gly Ser Gly Gly Gly Gly Ser
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: peptide linker

<400> SEQUENCE: 66

Gly Gly Gly Gly Ser Gly Gly Gly Ser Gly Gly Gly Gly Ser
1               5                   10                  15

<210> SEQ ID NO 67
<211> LENGTH: 8
<212> TYPE: PRT
<213> ORGANISM: Artificial Sequence
<220> FEATURE:
<223> OTHER INFORMATION: peptide linker

<400> SEQUENCE: 67

Gly Gly Gly Lys Gly Gly Gly Gly
1               5

<210> SEQ ID NO 68
```

```
<211> LENGTH: 8
<212> TYPE: PRT
<213> ORGANISM: Artificial Sequence
<220> FEATURE:
<223> OTHER INFORMATION: peptide linker

<400> SEQUENCE: 68

Gly Gly Gly Asn Gly Ser Gly Gly
1               5

<210> SEQ ID NO 69
<211> LENGTH: 8
<212> TYPE: PRT
<213> ORGANISM: Artificial Sequence
<220> FEATURE:
<223> OTHER INFORMATION: peptide linker

<400> SEQUENCE: 69

Gly Gly Gly Cys Gly Gly Gly Gly
1               5

<210> SEQ ID NO 70
<211> LENGTH: 5
<212> TYPE: PRT
<213> ORGANISM: Artificial Sequence
<220> FEATURE:
<223> OTHER INFORMATION: peptide linker

<400> SEQUENCE: 70

Gly Pro Asn Gly Gly
1               5

<210> SEQ ID NO 71
<211> LENGTH: 4
<212> TYPE: PRT
<213> ORGANISM: Homo sapiens

<400> SEQUENCE: 71

Trp Gly Pro Ile
1

<210> SEQ ID NO 72
<211> LENGTH: 5
<212> TYPE: PRT
<213> ORGANISM: Homo sapiens

<400> SEQUENCE: 72

Trp Gly Asp Pro Val
1               5

<210> SEQ ID NO 73
<211> LENGTH: 4
<212> TYPE: PRT
<213> ORGANISM: Homo sapiens

<400> SEQUENCE: 73

Trp Gly Asp Ile
1

<210> SEQ ID NO 74
<211> LENGTH: 5
<212> TYPE: PRT
<213> ORGANISM: Homo sapiens

<400> SEQUENCE: 74

Trp Gly Gln Pro Ile
1               5
```

```
<210> SEQ ID NO 75
<211> LENGTH: 5
<212> TYPE: PRT
<213> ORGANISM: Homo sapiens

<400> SEQUENCE: 75

Trp Gly Ala Pro Ile
1               5

<210> SEQ ID NO 76
<211> LENGTH: 5
<212> TYPE: PRT
<213> ORGANISM: Homo sapiens

<400> SEQUENCE: 76

Ala Gly Asp Pro Ile
1               5

<210> SEQ ID NO 77
<211> LENGTH: 5
<212> TYPE: PRT
<213> ORGANISM: Homo sapiens

<400> SEQUENCE: 77

Trp Ala Asp Pro Ile
1               5

<210> SEQ ID NO 78
<211> LENGTH: 5
<212> TYPE: PRT
<213> ORGANISM: Homo sapiens

<400> SEQUENCE: 78

Trp Gly Asp Ala Ile
1               5

<210> SEQ ID NO 79
<211> LENGTH: 5
<212> TYPE: PRT
<213> ORGANISM: Homo sapiens

<400> SEQUENCE: 79

Trp Gly Asp Pro Ala
1               5

<210> SEQ ID NO 80
<211> LENGTH: 4
<212> TYPE: PRT
<213> ORGANISM: Homo sapiens

<400> SEQUENCE: 80

Trp Asp Pro Ile
1

<210> SEQ ID NO 81
<211> LENGTH: 4
<212> TYPE: PRT
<213> ORGANISM: Homo sapiens

<400> SEQUENCE: 81

Trp Gly Asp Ile
1

<210> SEQ ID NO 82
```

```
-continued

<211> LENGTH: 4
<212> TYPE: PRT
<213> ORGANISM: Homo sapiens

<400> SEQUENCE: 82

Trp Gly Asp Pro
1

<210> SEQ ID NO 83
<211> LENGTH: 5
<212> TYPE: PRT
<213> ORGANISM: Homo sapiens

<400> SEQUENCE: 83

Phe Gly Asp Pro Ile
1               5

<210> SEQ ID NO 84
<211> LENGTH: 4
<212> TYPE: PRT
<213> ORGANISM: Homo sapiens

<400> SEQUENCE: 84

Gly Asp Pro Ile
1
```

CHIMERIC POLYPEPTIDES AND USES THEREOF

This application claims the benefit of U.S. Provisional Appln. No. 61/187,767 filed Jun. 17, 2009 and U.S. Provisional Appln. No. 61/265,548 filed Dec. 1, 2009, which are incorporated by reference herein.

REFERENCE TO THE SEQUENCE LISTING

The present application is being filed along with a Sequence Listing in electronic format. The Sequence Listing is provided as a file entitled A-1498-US-NP_Substitute_Sequence_Listing_ST25_.txt, created Feb. 8, 2012, which is 122 KB in size. The information in the electronic format of the Sequence Listing is incorporated herein by reference in its entirety.

FIELD OF THE INVENTION

The invention relates to nucleic acid molecules encoding chimeric polypeptides, chimeric polypeptides, pharmaceutical compositions comprising chimeric polypeptides and methods for treating a variety of metabolic disorders using such nucleic acids, polypeptides or pharmaceutical compositions.

BACKGROUND OF THE INVENTION

FGF19, FGF21, and FGF23 form a unique subfamily of fibroblast growth factors (FGFs). Unlike other FGFs, all three have been shown to function as endocrine hormones in the regulation of various metabolic processes (Fukumoto, (2008). *Endocr. J.* 55:23-31). For example, FGF23 originates in bone and regulates phosphate homeostasis in kidney (Fukumoto & Yamashita, (2007) *Bone* 40:1190-1195), FGF21 is expressed predominantly in liver but can signal in adipose tissue (Ogawa et al., (2007) *Proc. Natl. Acad. Sci. U.S.A.* 104:7432-7437), and FGF19 is secreted from ileum and functions as an enterohepatic signal for the regulation of bile acid metabolism (Inagaki et al. (2005) *Cell. Metab.* 2:217-225).

FGF19 and FGF21 appear to share many similarities with reported effects on the regulation of glucose, lipid, and energy metabolism. Both FGF19 and FGF21 transgenic mice are resistant to diet induced obesity, have lower body fat mass, and improved insulin sensitivity, glucose disposal, and plasma lipid parameters (Tomlinson et al., (2002) *Endocrinology* 143:1741-1747; Fu et al., (2004) *Endocrinology* 145:2594-2603; Kharitonenkov et al. (2005) *J Clin Invest* 115:1627-1635; Xu et al., (2008) *Diabetes* 58:250-59). Injection of recombinant FGF19 or FGF21 proteins in diabetic mouse models resulted in the reduction of serum glucose and insulin levels, improvements in glucose tolerance and liver steatosis, and reduction in body weight (Kharitonenkov et al., (2005) *J. Clin. Invest.* 115:1627-1635; Xu et al. (2008) *Diabetes* 58:250-59). In addition, FGF21 has also been shown to improve glucose, insulin and lipid profiles with reduced body weight in diabetic rhesus monkeys (Kharitonenkov et al., (2007) *Endocrinology* 148:774-781). Taken together, these observations signify the potential utility of these molecules as novel therapies for the treatment of diabetes and obesity.

Although this subfamily displays unique features as compared to other FGF molecules (Kurosu & Kuro-o, (2008) *Curr. Opin. Nephrol. Hypertens.* 17:368-372 (2008); Wu et al., (2008) *J. Biol. Chem.* 283(48):33304-9), FGF19, hepatocellular carcinoma (HCC) formation was observed in transgenic mice overexpressing FGF19 in skeletal muscle (Nicholes et al., (2002) *Am. J. Pathol.* 160:2295-2307). This has been a consideration in developing FGF19 as a therapy for diabetes, obesity and other metabolic disorders.

A chimeric polypeptide that exhibits potential for therapeutic use, while at the same time does not exhibit undesirable properties, such as mitogenicity, that would compromise the use of the polypeptide as a therapeutic, is therefore desirable.

SUMMARY OF THE INVENTION

A chimeric polypeptide comprising a wild type mature FGF19 polypeptide scaffold comprising SEQ ID NO:4, further comprising a modification that decreases FGFR4-mediated signaling activity is provided.

In one embodiment, one or more of the residues WGDPI (SEQ ID NO:49) at positions 16-20 of the FGF19 polypeptide scaffold has been substituted with (a) no amino acid; or (b) an amino acid other than the amino acid located at the position in the wild type amino acid sequence. The tryptophan residue of the WGDPI sequence can be deleted. Additionally, the residues WGDPI (SEQ ID NO:49) can be substituted with 1-5 contiguous residues present in either a wild type FGF21 or a wild type FGF23 amino acid sequence. The 1-5 contiguous residues can be present in a wild type FGF21 amino acid sequence, for example the 1-5 contiguous residues are GQV.

In a further embodiment one or more of the residues SGPHGLSS (SEQ ID NO:52) at positions 28-35 of the FGF19 polypeptide scaffold has been substituted with either (a) no amino acid; or (b) an amino acid other than the amino acid located at the position in the wild type amino acid sequence. The residues SGPHGLSS (SEQ ID NO:52) can be substituted with 1-8 contiguous residues present in either a wild type FGF21 or a wild type FGF23 amino acid sequence. The 1-8 contiguous residues can be present in a wild type FGF21 amino acid sequence, for example the 1-8 contiguous residues can be DDAQQTE (SEQ ID NO:54).

In another embodiment one or more of the residues SSAKQRQLYKNRGFLPL (SEQ ID NO:58) at positions 124-140 of the FGF19 polypeptide scaffold can be been substituted with either (a) no amino acid; or (b) an amino acid other than the amino acid located at the position in the wild type amino acid sequence. The residues SSAKQRQLYKN-RGFLPL (SEQ ID NO:58) can be substituted with 1-17 contiguous residues present in either a wild type FGF21 or a wild type FGF23 amino acid sequence. When the 1-17 contiguous residues are present in a wild type FGF21 amino acid sequence the 1-17 contiguous residues can be PGNK-SPHRDPAPRGP (SEQ ID NO:60).

Also provided is a chimeric polypeptide comprising a wild type FGF19 polypeptide scaffold comprising SEQ ID NO:4, wherein one or more of the residues WGDPI (SEQ ID NO:49) at positions 16-20 of SEQ ID NO:4 has been substituted with either (a) no amino acid; or (b) an amino acid other than the amino acid located at the position in the wild type amino acid sequence, and one or both of: (i) one or more of the residues SGPHGLSS (SEQ ID NO:52) at positions 28-35 of SEQ ID NO:4 has been substituted with either (1) no amino acid; or (2) an amino acid other than the amino acid located at the position in the wild type amino acid sequence; and (ii) one or more of the residues SSAKQRQLYKNRGFLPL (SEQ ID NO:58) at positions 124-140 of SEQ ID NO:4 has been substituted with either (1) no amino acid; or (2) an amino acid other than the amino acid located at the position in the wild type amino acid.

The residues WGDPI (SEQ ID NO:49) can be substituted with 1-5 contiguous residues present in either FGF21 or FGF23. The 1-5 contiguous residues can be present in wild type FGF21 amino acid sequence. The 1-5 contiguous residues can be GQV. Further, the tryptophan residue of the WGDPI (SEQ ID NO:49) sequence can be deleted.

The residues SGPHGLSS (SEQ ID NO:52) can be substituted with 1-8 contiguous residues present in either a wild type FGF21 or a wild type FGF23 amino acid sequence. The 1-8 contiguous residues can be present in a wild type FGF21 amino acid sequence. The 1-8 contiguous residues are DDAQQTE (SEQ ID NO:54).

The residues SSAKQRQLYKNRGFLPL (SEQ ID NO:58) can be substituted with 1-17 contiguous residues present in either a wild typd FGF21 or wild type FGF23 amino acid sequence. The 1-17 contiguous residues can be present in a wild type FGF21 amino acid sequence. The 1-17 contiguous residues can be PGNKSPHRDPAPRGP (SEQ ID NO:60).

In one particular embodiment, the residues WGDPI (SEQ ID NO:49) at positions 16-20 of SEQ ID NO:4 are substituted with GQV, and one or both of: (a) the residues SGPHGLSS (SEQ ID NO:52) at positions 28-35 of SEQ ID NO:4 are substituted with DDAQQTE (SEQ ID NO:54); and (b) the residues SSAKQRQLYKNRGFLPL (SEQ ID NO:58) at positions 124-140 of SEQ ID NO:4 are substituted with PGNKSPHRDPAPRGP (SEQ ID NO:60).

In other embodiments of a chimeric polypeptide provided herein, the polypeptide scaffold of SEQ ID NO:4 is truncated on the N terminus by 1-5 amino acids, on the C terminus by 1-15 amino acids or on both N terminus by 1-15 amino acids and on the C terminus by 1-15 amino acids. In yet another embodiment of a chimeric polypeptide except for the modification that decreases FGFR4-mediated signaling activity, the chimeric polypeptide comprises a polypeptide scaffold that is 95% or more identical to SEQ ID NO:4.

Nucleic acid molecules encoding the chimeric polypeptides are also disclosed, as well as vectors and host cells comprising the nucleic acid molecules.

Pharmaceutical compositions comprising the chimeric polypeptides and a pharmaceutically acceptable carrier are also disclosed. In another aspect, methods of treating diabetes and obesity comprising administering to a human patient in need thereof such pharmaceutical compositions are also disclosed.

Antibodies that specifically binds to the disclosed chimeric polypeptides are also disclosed. A kit for detecting the presence of the disclosed chimeric polypeptides comprising such antibodies are also disclosed.

Chimeric fusion polypeptides comprising the chimeric polypeptides fused to a heterogenous moiety, such as a Fc region of an IgG molecule or a PEG molecule are also disclosed.

BRIEF DESCRIPTION OF THE DRAWINGS

FIG. 1A shows liver sections from FGF19 and FGF21 treated animals and FIG. 1B is a bar graph depicting BrdU label incorporation in each test group.

FIG. 3 depicts the structure and activity a C-terminally truncated form of FGF19; FIG. 3A is a diagram graphically depicting the structure of the C-terminally truncated form of FGF19; FIG. 3B is a series of Western blots depicting FGF19 or truncated FGF19-mediated activation of FGFR4 or FGFR1c; FIG. 3C is a bar graph depicting BrdU incorporation by FGF19 or the truncated form of FGF19.

FIG. 4 depicts the structure of several FGF19/FGF21 chimeric polypeptides and the effect of each on FGFR4-mediated activity and BrdU incorporation; FIG. 4A is a graphical depiction of the FGF 19/21-1, FGF19/21-2, FGF19/21-3, FGF19/21-4 and FGF19/21-5 chimeric proteins, with FGF19 shown in white and FGF21 shown as gray;

FIG. 4B is a series of Western blots showing the effect of the FGF19/21-1, FGF19/21-2, FGF19/21-3, FGF19/21-4 and FGF19/21-5 chimeric polypeptides on FGFR1c (top panel) and FGFR4 (lower panel) mediated activity.

FIG. 5 depicts the structure and activity of the FGF21/19$^{38\text{-}42}$ chimeric polypeptide in which residues 42-44 of FGF21 were replaced by residues 38-42 of FGF19.

FIG. 6 depicts the structure and activity of two chimeric polypeptides, the FGF21/19$^{38\text{-}42}$ chimeric polypeptide in which either residues 42-44 of FGF21 were replaced by residues 38-42 of FGF19, and the FGF19/21$^{42\text{-}44}$ chimeric polypeptide in which residues 38-42 of FGF19 were replaced with residues 42-44 of FGF21; FIG. 6A is a graphical depiction of the chimeric polypeptides and indicates FGFR4 activity and BrdU incorporation; FIG. 6B depicts regions of FGF19 (DAGPHVHYGWGDPIRLRHLYT; SEQ ID NO:47) and FGF21 (DSSPLLQFGGQVRQRYLYT; SEQ ID NO:48), subsequences of which (WGDPI; SEQ ID NO:49 for FGF19) were exchanged in two chimeric polypeptides, FGF21/19$^{38\text{-}42}$ and FGF19/21$^{42\text{-}44}$, and analogous regions of FGF23 (NASPLLGSSWGGLIHLYT; SEQ ID NO:50) are also shown.

FIG. 7 depicts the β1-β2 loop region (LYTSGPHGLSS-CFL; SEQ ID NO:51) and the loop itself (underlined, SEQ ID NO:52; SGPHGLSS), and β10-β12 segment region (LPVSLSSAKQRQLYKNRGFLPLSHFLPM, SEQ ID NO:59) and the segment itself (underlined, SEQ ID NO:58; SSAKQRQLYKNRGFLPL) in FGF19, and analogous sequences in FGF21 (β1-β2 loop region: LYTD-DAQQTEAHL, SEQ ID NO:53, loop underlined, DDAQQTE. SEQ ID NO:54; β10-β12 segment region: LPLHLPGNKSPHRDPAPRGPARFLPL, SEQ ID NO:57, segment underlined, PGNKSPHROPAPRGP, SEQ ID NO:60) and FGF23 (β1-β2 loop region: LYTATARNSYHL, SEQ ID NO:55, loop underlined, ATARNS SEQ ID NO:56; β10-β12 segment region: FLVSLGRAKRAFLPGMNPP-PYSQFLSR, SEQ ID NO:61, segment underlined, SEQ ID NO:62).

FIG. 8 depicts the structure and activity of the three chimeric polypeptides, FGF19-1, FGF19-2 and FGF19-3, in which residues 50-57 of FGF19 were replaced with residues 52-58 of FGF21 (FGF19-1), residues 146-162 of FGF19 were replaced with residues 147-161 of FGF21 (FGF-2), or residues 50-57 of FGF19 were replaced with residues 52-58 of FGF21 and residues 146-162 of FGF19 were replaced with residues 147-161 of FGF21 (FGF19-3); FIG. 8D is a series of Western blots showing FGFR1c and FGFR4-mediated activity of the FGF19-1, FGF19-2 and FGF19-3 chimeric polypeptides in the presence and absence of βKlotho.

FIG. 9 depicts the structure and activity of the three chimeric polypeptides FGF19-4, FGF19-5 and FGF19-6 in which residues 38-42 of FGF19 were replaced with residues 42-44 of FGF21 and residues 50-57 of FGF19 were replaced with residues 52-58 of FGF21 (FGF19-4), residues 38-42 of FGF19 were replaced with residues 42-44 of FGF21 and residues 146-162 of FGF19 were replaced with residues 147-161 of FGF21 (FGF19-5), and residues 38-42 of FGF19 were replaced with residues 42-44 of FGF21, residues 50-57 of FGF19 were replaced with residues 52-58 of FGF21, and residues 146-162 of FGF19 were replaced with residues 147-161 of FGF21 (FGF19-6); FIG. 9B is a series of Western blots showing FGFR1c and FGFR4-mediated activity of the FGF19-4, FGF19-5 and FGF19-6 chimeric polypeptides in the presence and absence of βKlotho; FIG. 9C is a bar graph showing BrdU incorporation mediated by FGF19 and FGF19-4, FGF19-5 and FGF19-6.

FIG. 10 is a series of plots depicting the results of several assays performed on FGF19, FGF19-1 and FGF19-4; FIG. 10A depicts the effect of FGF19 and the FGF19-4 chimeric polypeptide on glucose uptake in a 3T3L1 cell-based assay; FIG. 10B shows the effect of FGF19 and FGF19-4 on plasma glucose in a ob/ob mouse model.

FIG. 11 is a plot depicting the pharmacokinetic properties of various FGF19/21 chimeric proteins.

FIG. 12 is a table showing the binding response of various FGF19 mutants having one or more mutations or deletions in the WGDPI (SEQ ID NO:49) region to FGFR1c and FGFR4.

DETAILED DESCRIPTION OF THE INVENTION

Figure 2A:
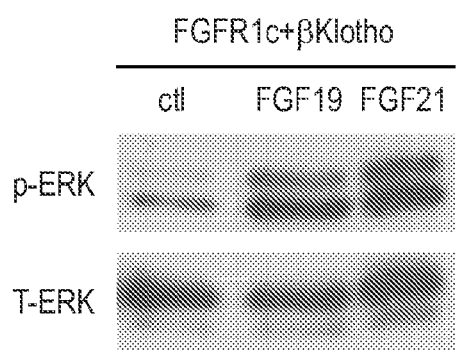
FIG. 2 is a series of Western blots depicting FGF21 or FGF19-mediated activation of FGFR1c (FIG. 2A), FGFR2c (FIG. 2B), FGFR3c (FIG. 2C), and FGFR4 (FIG. 2D).
Figure 2B:
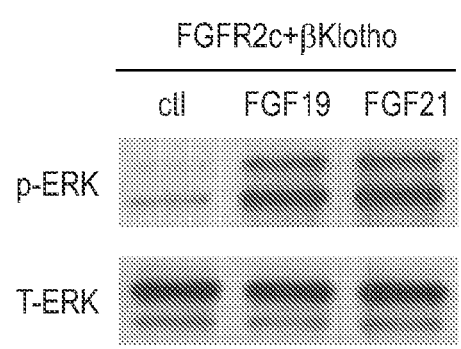
Figure 2C:
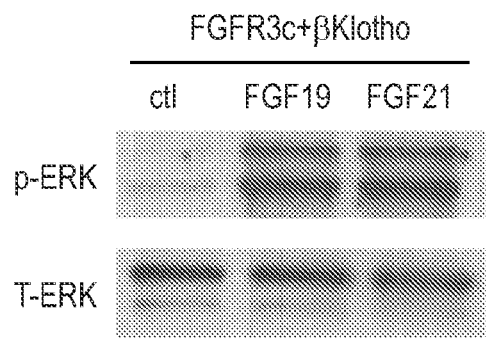
Figure 2D:
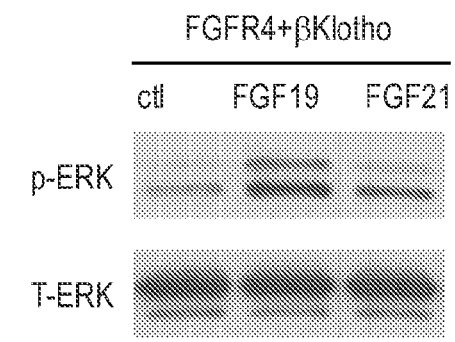

It has been suggested that constitutive hepatocellular proliferation is a prerequisite for transformation (Fausto, (1999) *Seminars in Liver Disease* 19:243-252). Accordingly, it is noted that dramatic increases in the proliferation of pericentral hepatocytes, as measured by enhanced BrdU labeling, was observed as early as 2 to 4 months of age in FGF19 transgenic animals as well as in normal mice subjected to six daily injections of recombinant FGF19 (Nicholes et al., (2002) *Am. J. Pathol.* 160:2295-2307). Cell lineage analysis of FGF19 induced tumors suggest that dysplastic and neoplastic hepatocytes originated from around the central veins, coincident with the increased pericentral proliferation observed by BrdU labeling (Nicholes et al., (2002) *Am. J. Pathol.* 160:2295-2307). Thus the relatively shorter BrdU labeling assay could serve as a marker to study mitogenic potential of these molecules in vivo. FGF21 has been shown to lack potential for cell proliferation in vitro (Kharitonenkov et al., (2005) *J. Clin. Invest.* 115:1627-1635).

The receptors for the FGF19, FGF21, FGF23 subfamily have been elucidated in recent years. Both FGF19 and FGF21 utilize βKlotho, a single transmembrane protein, as a co-receptor required for signaling mediated through FGFRs 1c, 2c, and 3c (Kurosu & Kuro-o, (2009) *Mol. Cell. Endocrinol.* 299:72-78). Because FGFR1c and 2c are the predominant receptors expressed in adipose tissue, induction of ERK phosphorylation and increased glucose uptake in adipocytes in vitro and in vivo upon treatment with either FGF19 or FGF21 are likely mediated through these receptors complexed with βKlotho in adipocytes (Kurosu et al., (2007) *J. Biol. Chem.* 282:26687-26695). Despite these similarities, a major difference between FGF19 and FGF21 exists with respect to FGFR4. Although both FGF19 and FGF21 appear to be able to bind to βKlotho/FGFR4 complexes, only FGF19 signals efficiently through FGFR4 (Kurosu et al., (2007) *J. Biol. Chem.* 282:26687-26695). Consistent with these in vitro observations, FGF19, but not FGF21, activates liver ERK phosphorylation, which is likely mediated through FGFR4, the predominant receptor expressed in liver (Kurosu et al., (2007) *J. Biol. Chem.* 282:26687-26695). Additionally, it has been suggested that FGFR4 could contribute to hepatocellular carcinoma progression, and increased production of alpha-fetoprotein, a hepatocellular carcinoma biomarker, has been observed with FGF19 stimulated liver cancer cell lines (Ho et al., (2009) *J. Hepatol.* 50:118-127).

As disclosed herein, a C-terminally truncated FGF19 and a series of FGF19 and FGF21 chimeric proteins was prepared and it was possible to identify three regions in FGF19 that are responsible for FGFR4 activation. A correlation between FGFR4 activation and hepatocellular proliferation, as indicated by BrdU incorporation, is disclosed. These results provide a direct link between liver FGFR4 activity and hepatocyte proliferation in vivo. Furthermore, it is disclosed that in contrast to FGF19, FGF21 does not activate FGFR4 and does not induce hepatocyte proliferation in vivo, making the various forms of FGF19 disclosed herein a unique potential therapeutic approach for the treatment metabolic diseases, such as obesity, diabetes and dyslipidemia.

Recombinant nucleic acid methods used herein, including in the Examples, are generally those set forth in Sambrook et al., *Molecular Cloning: A Laboratory Manual* (Cold Spring Harbor Laboratory Press, 1989) or *Current Protocols in Molecular Biology* (Ausubel et al., eds., Green Publishers Inc. and Wiley and Sons 1994), all of which are incorporated herein by reference for any purpose.

I. Definitions

As used herein, the terms "a" and "an" mean one or more unless specifically indicated otherwise.

As used herein, the term "chimeric polypeptide" refers to a polypeptide scaffold in which at least one amino acid of one or more regions comprising between 1 to 20 contiguous amino acids has been replaced with either no amino acid or an amino acid that is not found at the replaced amino acid's position in the region in a wild type polypeptide scaffold. In one example of a chimeric polypeptide, residues 38-42 of an FGF19 polypeptide scaffold are replaced with three residues from an FGF21 polypeptide, for example GQV, which is found at positions 42-44 of FGF21 or three residues from a FGF23 polypeptide, for example WGG which is found at positions 36-38 of FGF23. In another example the tryptophan residue at position 38 of a FGF19 polypeptide scaffold is replaced by an amino acid other than a tryptophan.

As used herein, the term "isolated nucleic acid molecule" refers to a nucleic acid molecule of the present disclosure that (1) has been separated from at least about 50, 60, 70, 80, 90, 95 or more percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecules or other contaminants that are found in its natural environment that would interfere with its use in polypeptide production or its therapeutic, diagnostic, prophylactic or research use.

The terms "polynucleotide" and "nucleic acid" are generally used interchangeably herein and refer to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Common bases include inosine, adenosine, guanosine, cytosine, uracil and thymidine.

As used herein, the term "isolated polypeptide" refers to a polypeptide of the present invention that (1) has been separated from at least about 50, 60, 70, 80, 90, 95 or more percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The terms "polypeptide" and "protein" are used interchangeably and refer to a compound made up of a single chain of amino acid residues linked by peptide bonds. A polypeptide or protein can, but need not, comprise non-naturally occurring amino acids and amino acid derivatives. A non-limiting lists of examples of non-naturally occurring amino acids that can be inserted into a protein or polypeptide (including chimeric polypeptides disclosed herein) include β-amino acids, homoamino acids, cyclic amino acids and amino acids with derivatized side chains. Examples include (in the L-form or D-form; abbreviated as in parentheses): para-acetyl-phenylalanine, para-azido-phenylalanine, para-bromo-phenylalanine, para-iodo-phenylalanine and para-ethynyl-phenylalanine, citrulline (Cit), homocitrulline (hCit), Nα-methylcitrulline (NMeCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK), Nα-methylglutamine(NMeQ), norleucine (Nle), norvaline (Nva), 1,2,3,4-tetrahydroisoquinoline (Tic), Octahydroindole-2-carboxylic acid (Oic), 3-(1-naphthyl)alanine (1-Nal), 3-(2-naphthyl)alanine (2-Nal), 1,2,3,4-tetrahydroisoquinoline (Tic), 2-indanylglycine (Igl), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α,β-diaminopropionoic acid (Dpr), α,γ-diaminobutyric acid (Dab), diaminopropionic acid (Dap), cyclohexylalanine (Cha), 4-methyl-phenylalanine (MePhe), β,β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), and other similar amino acids, and derivatized forms of any of those specifically listed.

As used herein, the term "vector" is used to refer to any molecule (e.g., nucleic acid, plasmid, or virus) used to transfer coding information to a host cell.

As used herein, the term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

As used herein, the term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

As used herein, the term "naturally occurring" when used in connection with biological materials such as nucleic acid molecules, polypeptides, host cells, and the like, refers to materials which are found in nature and are not manipulated by man. Similarly, "non-naturally occurring" as used herein refers to a material that is not found in nature or that has been structurally modified or synthesized by man. When used in connection with nucleotides, the term "naturally occurring" refers to the bases adenine (A), cytosine (C), guanine (G), thymine (T), and uracil (U). When used in connection with amino acids, the term "naturally occurring" refers to the 20 amino acids alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine(Q), arginine (R), serine (S), threonine (T), valine (V), tryptophan (W), and tyrosine (Y).

As used herein, the term "FGF19 polypeptide" refers to a polypeptide expressed in any species, including humans. For purposes of this disclosure, the term "FGF19 polypeptide" can be used interchangeably to refer to any full-length FGF19 polypeptide, e.g., SEQ ID NO:2, which consists of 216 amino acid residues and which is encoded by the nucleotide sequence of SEQ ID NO: 1, and any mature form of the polypeptide, e.g., SEQ ID NO:4, which consists of 194 amino acid residues and which is encoded by the nucleotide sequence of SEQ ID NO:3, and in which the 22 amino acid residues at the amino-terminal end of the full-length FGF19 polypeptide (i.e., those residues which constitute the signal peptide) have been removed. A bacterially expressed form of a mature FGF19 polypeptide can be produced from the nucleotide of SEQ ID NO:5 and have the amino acid sequence of SEQ ID NO:6, and which will comprise an N-terminal methionine residue. A "FGF19 polypeptide" can be encoded by SEQ ID NOs:1, 3 and 5, for example, as well as any polynucleotide sequence that, due to the degeneracy of the genetic code, has a polynucleotide sequence that is altered by one or more bases from the polynucleotide sequences of SEQ ID NOs:1, 3 and 5, as well as allelic variants of SEQ ID NOs:1, 3 and 5. The term "FGF19 polypeptide" also encompasses naturally-occurring FGF19 variants. A "FGF19" polypeptide can but need not incorporate one or more non-naturally occurring amino acids.

As used herein, the term "FGF21 polypeptide" refers to a polypeptide expressed in any species, including humans. For purposes of this disclosure, the term "FGF21 polypeptide" can be used interchangeably to refer to any full-length FGF21 polypeptide, e.g., SEQ ID NO:8, which consists of 209 amino acid residues and which is encoded by the nucleotide sequence of SEQ ID NO:7; any mature form of the polypeptide, e.g., SEQ ID NO:10, which consists of 181 amino acid residues and which is encoded by the nucleotide sequence of SEQ ID NO:9, and in which the 28 amino acid residues at the amino-terminal end of the full-length FGF21 polypeptide (i.e., those residues which constitute the signal peptide) have been removed. A bacterially expressed form of a mature FGF21 polypeptide can be produced from the nucleotide of SEQ ID NO:11 and have the amino acid sequence of SEQ ID NO:12 and will comprise an N-terminal methionine residue. A "FGF21 polypeptide" can be encoded by SEQ ID NOs:7, 9 and 11, for example, as well as any polynucleotide sequence that, due to the degeneracy of the genetic code, has a polynucleotide sequence that is altered by one or more bases from the polynucleotide sequence of SEQ ID NOs:7, 9 and 11, as well as allelic variants of SEQ ID NOs:7, 9 and 11. The term "FGF21 polypeptide" also encompasses naturally-occurring variants. A "FGF21" polypeptide can but need not incorporate one or more non-naturally occurring amino acids.

As used herein, the term "FGF23 polypeptide" refers to a polypeptide expressed in any species, including humans. For purposes of this disclosure, the term "FGF23 polypeptide" can be used interchangeably to refer to any full-length FGF23 polypeptide, e.g., SEQ ID NO:14, which consists of 251 amino acid residues and which is encoded by the nucleotide sequence of SEQ ID NO:13; any mature form of the polypeptide, e.g., SEQ ID NO:16, which consists of 227 amino acid residues and which is encoded by the nucleotide sequence of SEQ ID NO:15, and in which the 24 amino acid residues at the amino-terminal end of the full-length FGF23 polypeptide (i.e., those residues which constitute the signal peptide) have been removed. A bacterially expressed form of a mature FGF23 polypeptide can be produced from the nucleotide of SEQ ID NO:18 and have the amino acid sequence of SEQ ID NO:17, and will comprise an N-terminal methionine residue. A "FGF23 polypeptide" can be encoded by SEQ ID NOs: 13, 15 and 17, for example, as well as any polynucleotide sequence that, due to the degeneracy of the genetic code, has a polynucleotide sequence that is altered by one or more bases from the polynucleotide sequence of SEQ ID NOs:13, 15 and 17, as well as allelic variants of SEQ ID NOs:13, 15 and 17. The term "FGF23 polypeptide" also encompasses naturally-occurring variants. A "FGF23" polypeptide can but need not incorporate one or more non-naturally occurring amino acids.

As used herein, the terms "effective amount" and "therapeutically effective amount" each refer to the amount of a chimeric polypeptide disclosed herein used to support an observable level of one or more biological activities of the wild-type polypeptide scaffold, such as the ability to lower blood glucose, insulin, triglyceride, or cholesterol levels; reduce body weight; or improve glucose tolerance, energy expenditure, or insulin sensitivity in a human or non-human subject.

As used herein, the term "pharmaceutically acceptable carrier" or "physiologically acceptable carrier" as used herein refers to one or more formulation materials suitable for accomplishing or enhancing the delivery of a chimeric polypeptide disclosed herein.

As used herein, the terms "biological activity" and "biologically active" when used in connection with a polypeptide scaffold or a chimeric polypeptide of the instant disclosure mean that the polypeptide scaffold or chimeric polypeptide possesses an activity of the polypeptide scaffold, such as the ability to lower blood glucose, insulin, triglyceride, or cholesterol; to reduce body weight; or to improve glucose tolerance, energy expenditure, or enhance insulin sensitivity when assayed in an appropriate assay such as those provided herein, regardless of the type or number of modifications that have been introduced into the chimeric polypeptide. Chimeric polypeptides possessing a somewhat decreased level of activity relative to the polypeptide scaffold can nonetheless be considered to be biologically active chimeric polypeptides. One particular example of a biological activity is the ability to increase glucose uptake in 3T3L1 cells by 1.2 fold or higher over basal levels in an in vitro glucose uptake assay as shown in Example 10.

As used herein, the term "polypeptide scaffold" means a polypeptide which has been modified to form a chimeric polypeptide as described herein. Examples of polypeptide scaffolds that can form the basis of a chimeric polypeptide include wild type FGF19, FGF21 and FGF23 polypeptide sequences.

As used herein, the term "conservative amino acid substitution" means a substitution of a native amino acid residue (i.e., a residue found in a given position of a wild-type polypeptide scaffold sequence) with a normative residue (i.e., a residue that is not found in a given position of the wild type polypeptide scaffold sequence) such that there is little or no effect on the polarity or charge of the amino acid residue at that position. Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues can be divided into classes based on common side chain properties:
  (1) hydrophobic: norleucine, Met, Ala, Val, Leu, Ile;
  (2) neutral hydrophilic: Cys, Ser, Thr;
  (3) acidic: Asp, Glu;
  (4) basic: Asn, Gln, His, Lys, Arg;
  (5) residues that influence chain orientation: Gly, Pro; and
  (6) aromatic: Trp, Tyr, Phe.

Conservative substitutions can involve the exchange of a member of one of these classes for another member of the same class. Non-conservative substitutions can involve the exchange of a member of one of these classes for a member from another class.

Desired amino acid substitutions (whether conservative or non-conservative) can be determined by those skilled in the art at the time such substitutions are desired. An exemplary (but not limiting) list of amino acid substitutions is set forth in Table 1.

TABLE 1

Amino Acid Substitutions

| Original Residue | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

II. Chimeric Polypeptides

In one aspect of the present disclosure, a series of chimeric polypeptides are described. These chimeric polypeptides are based on a wild type FGF19, FGF21 or FGF23 polypeptide scaffold wherein one or more of the residues in a contiguous region of 1-20 amino acids of the polypeptide scaffold, e.g., 1, 2, 3, 4, 5, 6, 7, 8, 9, 10, 11, 12, 13, 14, 15, 16, 17, 18, 19 or 20 amino acids, have been replaced with (a) no amino acid (a deletion); or (b) an amino acid other than the amino acid located at the position in the wild type sequence (i.e., a substitution or a mutation).

In addition to having a modulating effect on particular biological activities of a polypeptide scaffold, the chimeric polypeptides described herein can have other retained or enhanced biological activities of the polypeptide scaffold, such as the ability to lower blood glucose in vivo. For example, the chimeric polypeptides disclosed herein can exhibit an enhanced or decreased degree of FGFR4 activation and yet still retain any glucose lowering effects inherent to the polypeptide scaffold, possibly making such a molecule more therapeutically attractive than the unmodified polypeptide scaffold. In the case of a FGF19 polypeptide scaffold, for example, a chimeric polypeptide built on the FGF19 scaffold can have decreased ability to activate FGFR4 and/or decreased hepatocyte mitogenicity, while at the same time still showing the glucose lowering effects inherent to FGF19. In another example, a chimeric polypeptide built on a FGF21 scaffold can have an increased ability to activate FGFR4 and/or enhanced hepatocyte mitogenicity, while at the same time showing the glucose lowering effects inherent in FGF21. Thus, in some embodiments the chimeric polypeptides disclosed herein, comprise molecules in which properties deemed desirable in a given circumstance have been maintained or augmented, while properties deemed undesirable in the same circumstance have been decreased or eliminated.

In any of the disclosed chimeric polypeptides, a substitution can comprise any naturally or non-naturally occurring amino acid. Such a substitution can be a conservative substitution, as described herein, or non-conservative. In some cases, in which it is desired to disrupt a particular effect it may be desirable to make a non-conservative substitution at a given position or insert a non-naturally occurring amino acid. In other cases, a conservative substitution may mitigate or enhance a particular effect to a desired degree. In still other cases, a substitution of no amino acid at one or more positions (a deletion) may mitigate or enhance a particular effect to a desired degree.

Over the span of a contiguous region of a polypeptide scaffold in which two or more amino acid residues are being replaced with amino acids or no amino acid, any combination can be employed without restriction. That is, a two or more amino acids in a contiguous region can be replaced with no amino acid, a naturally occurring amino acid, a non-naturally occurring amino acid, a conservative substitution, a non-conservative substitution or any combination thereof. In fact, in some cases an omission at a given position in a region of a polypeptide scaffold coupled with a conservative and/or non-conservative substitution at one or more other positions in the same region of the scaffold may mitigate or enhance a particular effect to a desired degree, allowing a level of control over the activity of a chimeric polypeptide.

The present disclosure, therefore, encompasses not only chimeric polypeptides that fully impart a desired effect or property, but also that that partially impart a desired effect or property. By way of example, the present disclosure encompasses both chimeric polypeptides that completely eliminate an effect such as the mitogenicity or FGFR4 activation normally associated with a FGF19 polypeptide scaffold, and chimeric polypeptides that partially eliminate the same effects, which can be desirable in some circumstances. Also encompassed are chimeric polypeptides that enhance an effect such as mitogenicity or FGFR4 activation, which can be desirable in some circumstances.

The biological activity of the chimeric polypeptides disclosed herein can be assayed in any assay appropriate to the metric desired. For example, a binding assay such as an in vitro or in vivo ERK or FRS2 assay can be employed to examine FGFR activity, target gene expression analysis can be performed in vitro or in vivo, glucose uptake can be studied in adipocytes, and glucose lowering ability, as shown herein in Examples 2.3 and 10, effects on body weight, plasma lipid profiles, energy expenditures, can be studied in other in vitro or in vivo functional assays. Various in vivo assays can also be employed to study the biological activity of polypeptide scaffolds and chimeric polypeptides, including histopathological analysis to examine BrdU incorporation in the livers of test animals. This assay is demonstrated in Example 2.4 and exemplary results are shown in FIG. 1A.

II.A. Chimeric Polypeptides that do not Signal Through FGFR4

The present disclosure relates to chimeric polypeptides that do not signal through FGFR4. In one embodiment, an isolated chimeric polypeptide comprises the amino acid sequence of a wild type FGF19 (e.g., SEQ ID NOs:2, 4 or 6) polypeptide scaffold, which has been modified such that it does not signal through FGFR4. As shown in the Examples presented herein, three regions or a subset thereof, are sufficient for FGFR4 signaling in a FGF19 polypeptide scaffold, namely residues 38-42, 50-57 and 146-162 of SEQ ID NO:2 (residues 16-20, 28-35 and 124-140 of SEQ ID NO:4 and residues 17-21, 29-36 and 125-141 of SEQ ID NO:6). Thus, a chimeric polypeptide based on a FGF19 polypeptide scaffold that signals through FGFR1c but not FGFR4 will have at least one of these regions modified. In one example, at least one of these regions of the FGF19 polypeptide scaffold can be modified by replacing at least one amino acid in the region with either no amino acid or an amino acid not found at the position in the region of the scaffold. Thus, in this example at least one residue of residues 38-42 of the FG19 scaffold will be replaced with either no amino acid or an amino acid not found at the position in the scaffold. In one particular embodiment, the tryptophan residue at position 38 is mutated to a residue other than tryptophan or is deleted (see Example 12).

Similarly, if it is desired to impart the ability to signal through FGFR4 but not FGFR1c, residues 38-42, 50-57 and 146-162 of SEQ ID NO:2 (residues 16-20, 28-35 and 124-140 of SEQ ID NO:4 and residues 17-21, 29-36 and 125-141 of SEQ ID NO:6) can be used to replace the analogous regions of a non-FGF19 polypeptide scaffold, such as a FGF21 or FGF23 polypeptide scaffold.

It is noted that although the disclosed regions of FGF19 are sufficient for FGFR4-mediated signaling, additional regions of FGF19 may also contribute to FGFR4-mediated signaling. The present disclosure, therefore, contemplates that additional residues and/or regions of a scaffold polypeptide may play a role in FGFR4-mediated signaling, in conjunction with the disclosed regions. Accordingly, chimeric polypeptides comprising substitutions and/or deletions at those regions form an embodiment of the present disclosure.

II.B. Chimeric Polypeptides Lacking or Incorporating FGF19 Residues 38-42

In one aspect, the present disclosure relates to chimeric polypeptides that are based on an FGF21 polypeptide scaffold. In one embodiment, such a chimeric polypeptide comprises the amino acid sequence of a wild type FGF21 (e.g., SEQ ID NOs:8, 10 and 12) polypeptide scaffold, wherein one or more of the residues of GQV at positions 42-44 of SEQ ID NO:8 (positions 14-16 of SEQ ID NO:10 and 15-17 of SEQ ID NO:12) has been replaced with (a) no amino acid (a deletion); or (b) an amino acid other than the amino acid located at the position in the wild type sequence. In another example, the residues at positions 42-44 of a wild type FGF21 polypeptide (i.e., GQV) are replaced by residues at position 38-42 of a wild type FGF19 sequence (i.e., WGDPI) (SEQ ID NO:49). In this particular chimeric polypeptide, it is noted that three residues in a region of a FGF21 polypeptide scaffold are replaced by five residues from a FGF19 polypeptide, highlighting the option of replacing a particular residue at a particular position in a polypeptide scaffold with more than one amino acid, i.e., replacing three amino acids in a region with five amino acids.

The present disclosure also relates to chimeric polypeptides that are based on a FGF19 polypeptide scaffold. In one embodiment, such a chimeric polypeptide comprises the amino acid sequence of a wild type FGF19 (SEQ ID NOs:2, 4 or 6) polypeptide scaffold, wherein one or more of the residues of WGDPI (SEQ ID NO:49) at positions 38-42 of SEQ ID NO:2 (positions 16-20 of SEQ ID NO:4 and 17-21 of SEQ ID NO:6) has been replaced with (a) no amino acid (a deletion); or (b) an amino acid other than the amino acid located at the position in the wild type sequence. In another example, the residues of FGF21 at positions 42-44 of SEQ ID NO:8 (positions 14-16 of SEQ ID NO:10 and 15-17 of SEQ ID NO:12), i.e., the residues GQV, are inserted at position 38-42 of SEQ ID NO:2 (positions 16-20 of SEQ ID NO:4 and 17-21 of SEQ ID NO:6). In this particular chimeric polypeptide, it is noted that five residues of a FGF19 polypeptide scaffold are being replaced by three residues from a FGF21 polypeptide, highlighting the option of replacing a particular residue at a particular position in a polypeptide scaffold with no amino acid (i.e., making a deletion). Such chimeric polypeptides can exhibit the properties of reduced FGF4 activation and/or hepatocyte mitogenicity.

In another embodiment, a chimeric polypeptide comprises the amino acid sequence of a wild type FGF23 (SEQ ID NOs:14, 16 or 18) polypeptide scaffold, wherein one or more of the residues of WGG at positions 36-38 of SEQ ID NO:14 (positions 12-14 in SEQ ID NO:16 and 13-15 in SEQ ID NO:18) has been replaced with at (a) no amino acid (a deletion); or (b) an amino acid other than the amino acid located at the position in the wild type sequence. In another example, the residues of FGF23 at positions 36-38 of SEQ ID NO:14 (positions 12-14 of SEQ ID NO:16 and 13-15 in SEQ ID NO:18), e.g., the residues WGG, are replaced by the FGF19 residues at position 38-42 of SEQ ID NO:2 (positions 16-20 of SEQ ID NO:4 and 17-21 of SEQ ID NO:6), e.g., WGDPI (SEQ ID NO:49). In this particular chimeric polypeptide, it is noted that three residues of a FGF23 polypeptide scaffold are being replaced by five residues from a FGF19 polypeptide, highlighting the option of replacing a particular residue at a particular position in a region of a polypeptide scaffold with more than one amino acid, i.e., replacing three amino acids in a region with five amino acids.

As with all of the chimeric polypeptides of the present invention, the particular amino acids to be replaced in a FGF19, FGF21 or FGF23 polypeptide scaffold can be substituted with either no amino acid or with any amino acid other than the residue that appears at that position in the wild type sequence. For example, FGF19 residues 38-42 of SEQ ID NO:2 (positions 16-20 of SEQ ID NO:4 and 17-21 of SEQ ID NO:6) comprise the five residue sequence WGDPI (SEQ ID NO:49), and can be substituted with any sequence other than WGDPI.(SEQ ID NO:49) and can also comprise less than five residues or more than five residues. A more specific example is the replacement of the five residues of FGF19, namely WGDPI (SEQ ID NO:49) with the three residues normally found in FGF21 at positions 42-44 of SEQ ID NO:8 (positions 14-16 of SEQ ID NO:10 and 15-17 of SEQ ID NO:12), namely GQV.

II.C. Chimeric Polypeptides Lacking or Incorporating the FGF19 β1-β2 Loop

The β1-β2 loop of FGF19 is thought to contribute to heparin binding activity, and analogous regions are found in FGF21 and FGF23. A chimeric polypeptide comprising this loop region is expected contribute to the activation of FGFR4, which is not normally activated by FGF21 or FGF23, for example, and can contribute to hepatocyte mitogenicity, again, a property not normally observed in FGF21 or FGF23. Similarly, a chimeric polypeptide lacking this loop region, in conjunction with other modifications, is expected to lack the ability to signal through FGFR4.

In one aspect, the present disclosure relates to chimeric polypeptides that are based on an FGF21 scaffold. In one aspect, a chimeric polypeptide comprises the amino acid sequence of a wild type FGF21 (SEQ ID NOs: 8, 10 or 12) polypeptide scaffold wherein one or more of the residues DDAQQTE (SEQ ID NO:54) at positions 52-58 of SEQ ID NO:8 (positions 24-30 in SEQ ID NO:10 and 25-31 in SEQ ID NO:12) has been replaced with (a) no amino acid (a deletion); or (b) an amino acid other than the amino acid located at the position in the wild type sequence.

The present disclosure relates, in one aspect, to chimeric polypeptides that are based on an FGF23 scaffold. In one aspect, a chimeric polypeptide comprises the amino acid sequence of a wild type FGF23 (SEQ ID NOs:14, 16 or 18) polypeptide scaffold wherein one or more of the residues ATARNS (SEQ ID NO:56) at positions 45-50 of SEQ ID NO:14 (positions 21-26 of SEQ ID NO:16 and 22-27 of SEQ ID NO:18) has been replaced with at least one of (a) no amino acid (a deletion); or (b) an amino acid other than the amino acid located at the position in the wild type sequence.

The present disclosure also relates to chimeric polypeptides that are based on a FGF19 scaffold. In one embodiment such a chimeric polypeptide comprises the amino acid sequence of a wild type FGF19 (SEQ ID NOs:2, 4 or 6) polypeptide scaffold wherein one or more of the residues SGPHGLSS (SEQ ID NO:52) at positions 50-57 of SEQ ID NO:2 (positions 28-35 of SEQ ID NO:4 and positions 29-36 of SEQ ID NO:6) has been replaced with at least one of (a) no amino acid (a deletion); or (b) an amino acid other than the amino acid located at the position in the wild type sequence. In one example, the FGF21 residues at positions 52-58 of SEQ ID NO:8 (positions 24-30 of SEQ ID NO:10 and 25-31 of SEQ ID NO:12), e.g., the residues DDAQQTE, (SEQ ID NO:54) are inserted at position 50-57 of a wild type FGF19 sequence. In this particular chimeric polypeptide, it is noted that eight residues of a FGF19 polypeptide are being replaced by seven residues from a FGF21 polypeptide, highlighting the option of replacing a particular residue at a particular position in a polypeptide scaffold with no amino acid. Such chimeric polypeptides can exhibit the properties of reduced FGF4 activation and/or hepatocyte mitogenicity in and of itself, or such a substitution can form one element in a combination chimeric polypeptide, as described herein.

As with all of the chimeric polypeptides of the present invention, the particular amino acids to be replaced can be substituted with either no amino acid or with any amino acid other than the residue that appears at that position in the wild type sequence. For example, FGF19 residues 50-57 of SEQ ID NO:2 (positions 28-35 of SEQ ID NO:4 and positions 29-36 of SEQ ID NO:6) is the eight residue sequence SGPHGLSS, and could be substituted with any sequence other than SGPHGLSS (SEQ ID NO:52) and could also comprise less than eight residues. A more specific example is the replacement of these residues with the seven FGF21 residues found at positions 52-58 of SEQ ID NO:8 (positions 24-30 of SEQ ID NO:10 and 25-31 of SEQ ID NO:12), namely DDAQQTE (SEQ ID NO:54).

II.D. Chimeric Polypeptides Lacking or Incorporating the FGF19 β10-β12 Segment

The β10-β12 segment of FGF19 is thought to contribute to heparin binding activity and is a region found analogously in FGF19, FGF21 and FGF23. Such a chimeric polypeptide can contribute to the activation of FGFR4, which is not normally activated by FGF21, as well as contribute to hepatocyte mitogenicity, again, a property not normally observed in FGF21.

In various embodiments, the present disclosure relates to chimeric polypeptides that are based on FGF19, FGF21 and FGF23 scaffolds.

In one aspect, a chimeric polypeptide comprising the amino acid sequence of a wild type FGF21 polypeptide scaffold (e.g., SEQ ID NOs:10, 12 or 14) wherein one or more of the residues PGNKSPHRDPAPRGP (SEQ ID NO:60) at positions 147-161 of SEQ ID NO:8 (positions 119-133 in SEQ ID NO:10 and 120-134 in SEQ ID NO:12) has been replaced with at least one of (a) no amino acid (a deletion); or (b) an amino acid other than the amino acid located at the position in the wild type amino acid sequence.

In one aspect, a chimeric polypeptide comprising the amino acid sequence of a wild type FGF23 polypeptide scaffold (e.g., SEQ ID NOs:14, 16 or 18) wherein one or more of the residues GRAKRAFLPGMNPPPY (SEQ ID NO:62) at positions 139-154 of SEQ ID NO:14 (positions 115-130 in SEQ ID NO:16 and 116-131 in SEQ ID NO:18) has been replaced with (a) no amino acid (a deletion); or (b) an amino acid other than the amino acid located at the position in the wild type amino acid sequence.

The present disclosure also relates to chimeric polypeptides that are based on a FGF19 scaffold. In one embodiment of such a chimeric polypeptide comprises the amino acid sequence of a wild type FGF19 polypeptide scaffold (e.g., SEQ ID NOs:2, 4 or 6) wherein one or more of the residues SSAKQRQLYKNRGFLPL (SEQ ID NO:58) at positions 146-163 of SEQ ID NO:2 (positions 124-140 in SEQ ID NO:4 and 125-141 in SEQ ID NO:6) has been replaced with (a) no amino acid (a deletion); or (b) an amino acid other than the amino acid located at the position in the wild type amino acid sequence. In one example, the FGF21 residues at positions 147-161 of SEQ ID NO:8 (corresponding to positions 119-133 of SEQ ID NO:10 and 120-134 of SEQ ID NO:12), e.g., PGNKSPHRDPAPRGP (SEQ ID NO:60), are inserted at position 146-162 of FGF19 sequence SEQ ID NO:2 (corresponding to positions 124-140 of SEQ ID NO:4 and 125-141 of SEQ ID NO:6). In this particular chimeric polypeptide, it is noted that 17 residues of a FGF19 polypeptide are being replaced by 15 residues from a FGF21 polypeptide, highlighting the option of replacing a particular residue at a particular position in a polypeptide scaffold with no amino acid. Such chimeric polypeptides are expected to exhibit the properties of reduced FGFR4 activation and/or hepatocyte mitogenicity in and of itself, or such a substitution can form one element in a combination chimeric polypeptide, as described herein.

As with all of the chimeric polypeptides of the present invention, the particular amino acids to be replaced can be substituted with either no amino acid or with any amino acid other than the residue that appears at that position in the wild type sequence. For example, FGF19 residues 146-162 of SEQ ID NO:2 (corresponding to positions 124-140 of SEQ ID NO:4 and 125-141 of SEQ ID NO:6) is the 17 residue sequence SSAKQRQLYKNRGFLPL (SEQ ID NO:58), and could be substituted with any sequence other than SSAKQRQLYKNRGFLPL and could also comprise less than 17 residues. A more specific example is the replacement of these residues with the 15 FGF21 residues found at positions 147-161 of SEQ ID NO:8 (corresponding to positions 119-133 of SEQ ID NO:10 and 120-134 of SEQ ID NO:12), namely PGNKSPHRDPAPRGP (SEQ ID NO:60).

II.E. Chimeric Combination Polypeptides

The present disclosure also relates to chimeric combination polypeptides. A chimeric combination polypeptide is a chimeric polypeptide in which two or more regions of a polypeptide scaffold have been replaced at each position of each region with either no amino acid or an amino acid not normally found at the position in the wild type polypeptide scaffold. Chimeric combination polypeptides can therefore be engineered to demonstrate enhanced or reduced properties normally associated with the polypeptide scaffold, or properties not normally associated with the polypeptide scaffold. In various embodiments, a chimeric combination polypeptide can have the property of exhibiting decreased FGFR4-mediated signaling.

By way of example, a chimeric combination polypeptide can be built on a FGF19 scaffold. The amino acids in two or more particular regions of a FGF19 scaffold, such as the region comprising positions 38-42 and/or the regiOn comprising positions 50-57 and/or the region comprising positions 146-162 of SEQ ID NO:2 (corresponding to positions 16-20, 28-35 and 124-140 of SEQ ID NO:4 and 17-21, 29-36 and 125-141 of SEQ ID NO:6), can each be replaced by either residues not found at each of positions 38-42 and/or 50-57 and/or 146-162 in SEQ ID NO:2, (positions 16-20, 28-35 and 124-140 of SEQ ID NO:4, or positions 17-21, 29-36 and 125-141 of SEQ ID NO:6), or by no amino acid. In one particular embodiment, a chimeric combination polypeptide can have amino acids from regions of FGF21 substituted for the wild type regions of the FGF19 polypeptide scaffold. One possible sequence of this chimeric polypeptide comprises an FGF19 scaffold in which (a) one or more of the residues WGDPI (SEQ ID NO:49) at positions 38-42 of SEQ ID NO:2 has been substituted with (i) no amino acid (a deletion); or (ii) an amino acid other than the amino acid located at the position in the wild type amino acid sequence; (b) one or more of the residues SGPHGLSS (SEQ ID NO:52) at positions 50-57 of SEQ ID NO:2 (corresponding to positions 28-35 of SEQ ID NO:4 and positions 29-36 of SEQ ID NO:6) has been substituted with (i) no amino acid (a deletion); or (ii) an amino acid other than the amino acid located at the position in the wild type amino acid sequence; and (c) one or more of the residues SSAKQRQLYKNRGFLPL (SEQ ID NO:58) at positions 146-163 of SEQ ID NO:2 (corresponding to positions 124-140 of SEQ ID NO:4 and 125-141 of SEQ ID NO:6) has been substituted with (i) no amino acid; or (ii) an amino acid other than the amino acid located at the position in the wild type amino acid.

As disclosed herein, by replacing at least one amino acid of the 38-42 region of a FGF19 polypeptide scaffold of SEQ ID NO:2 (corresponding to positions 14-20 of SEQ ID NO:4 and 15-21 of SEQ ID NO:6) with either no amino acid or a non wild type residue at least one of these positions, the ability of FGF19 to activate FGFR4 is diminished and hepatocyte mitogenicity is also diminished. By replacing at least one of the 50-57 region of a FGF19 polypeptide scaffold of SEQ ID NO:2 (corresponding to positions 28-35 of SEQ ID NO:4 and 29-36 of SEQ ID NO:6), which comprises the heparin binding β1-β2 loop and/or at least one amino acid of the 146-162 region of a FGF19 polypeptide scaffold of SEQ ID NO:2 (corresponding to positions 124-140 of SEQ ID NO:4 and 125-141 of SEQ ID NO:6), which comprises the β10-β12 segment, with either no amino acid or a non-wild type residue at least one of these positions, FGFR4 activation and hepatocyte mitogenicity of FGF19 can be still further diminished or eliminated. It is significant to note, however, that a chimeric combination polypeptide comprising substitutions at one or more regions can still maintain other biological activities, such as the ability to lower blood glucose levels or decrease body weight. Thus, a chimeric combination polypeptide can be engineered to achieve various goals and to exhibit a desired activity profile by substituting the amino acids of two or more regions of a polypeptide scaffold with amino acids not found at each of the positions of the regions in the wild type polypeptide scaffold or with no amino acid (a deletion).

In another example, a chimeric combination polypeptide can be built on a FGF21 scaffold. The amino acids in two or more particular regions of a FGF21 scaffold (e.g., SEQ ID NOs:8, 10 or 12), such as the region comprising positions 42-44 and/or the region comprising positions 52-58 and/or the region comprising positions 147-161 of SEQ ID NO:8 (corresponding to positions 14-16, 24-30 and 119-133 of SEQ ID NO:10 and 15-17, 25-31 and 120-134 of SEQ ID NO:12), can each be replaced with residues not found at each of positions 42-44 and/or 52-58 and/or 147-161 of SEQ ID NO:8 (corresponding to positions 14-16, 24-30 and 119-133 of SEQ ID NO:10 and 15-17, 25-31 and 120-134 of SEQ ID NO:12), or with no amino acid. In one particular embodiment of such a chimeric combination polypeptide could have amino acids from regions of FGF19 substituted for the wild type regions of the FGF21 polypeptide scaffold. One possible sequence of such a chimeric polypeptide comprises a polypeptide scaffold in which (a) one or more of the residues GQV at positions 42-44 of SEQ ID NO:8 (corresponding to positions 14-16 of SEQ ID NO:10 and 15-17 of SEQ ID NO:12) has been substituted with (i) no amino acid (a deletion); or (ii) an amino acid other than the amino acid located at the position in the wild type amino acid sequence; (b) one or more of the residues DDAQQTE (SEQ ID NO:54) at positions 52-58 of SEQ ID NO:8 (corresponding to positions 24-30 in SEQ ID NO:10 and 25-31 of SEQ ID NO:12) has been substituted with (ii) no amino acid (a deletion); or (ii) an amino acid other than the amino acid located at the position in the wild type amino acid sequence; and (c) one or more of the residues PGNKSPHRDPAPRGP (SEQ ID NO:60) at positions 147-161 of SEQ ID NO:8 (corresponding to positions 119-133 in SEQ ID NO:10 and 120-134 in SEQ ID NO:12) has been substituted with (i) no amino acid (a deletion); or (ii) an amino acid other than the amino acid located at the position in the wild type amino acid.

As described herein, by replacing at least one amino acid of the 42-44 region of a FGF21 polypeptide scaffold of SEQ ID NO:8 (and corresponding residues in SEQ ID NOs:10 and 12) with either no amino acid or a non wild type residue at one or more of these positions, the ability of FGF21 to activate FGFR4 is imparted and hepatocyte mitogenicity is also imparted. By replacing at least one of the 52-58 region of a FGF21 polypeptide scaffold of SEQ ID NO:8 (and corresponding residues of SEQ ID NOs:10 and 12), which comprises the heparin binding β1-β2 loop, and/or one or more amino acids of the 147-161 region of a FGF19 polypeptide scaffold of SEQ ID NO:8 (and corresponding residues of SEQ ID NOs:10 and 12), which comprises the β10-β12 segment, with no amino acid or a non-wild type residue at one or more of these positions, FGFR4 activation and hepatocyte mitogenicity of FGF19 can be further augmented.

In yet another example, a chimeric combination polypeptide can be built on a FGF23 scaffold. The amino acids in two or more particular regions of a FGF23 scaffold (e.g., SEQ ID NOs:14, 16 or 18), such as the region comprising positions 36-38 and/or the region comprising positions 45-50 and/or the region comprising positions 139-154 of SEQ ID NO:14 (corresponding to positions 12-14, 21-26 and 115-130 of SEQ ID NO:16 and 13-15, 22-27 and 116-131 of SEQ ID NO:18), can each be replaced by residues not found at each of positions 36-38 and/or 45-50 and/or 139-154 in SEQ ID NO:14 (corresponding to positions 12-14, 21-26 and 115-130 of SEQ ID NO:16 and 13-15, 22-27 and 116-131 of SEQ ID NO:18), or by no amino acid. In one particular embodiment of such a chimeric combination polypeptide can have amino acids from regions of FGF19 substituted for the wild type regions of the FGF23 polypeptide scaffold. One possible sequence of such a chimeric polypeptide comprises a polypeptide scaffold in which (a) one or more of the residues WGG at positions 36-38 of SEQ ID NO:14 (corresponding to positions 12-14 in SEQ ID NO:16 and 13-15 in SEQ ID NO:18) has been substituted with (i) no amino acid; or (ii) an amino acid other than the amino acid located at the position in the wild type amino acid sequence; (b) one or more of the residues ATARNS (SEQ ID NO:56) at positions 45-50 of SEQ ID NO:14 (corresponding to positions 21-26 in SEQ ID NO:16 and 22-27 in SEQ ID NO:18) has been substituted with at least one of (i) no amino acid; or (ii) an amino acid other than the amino acid located at the position in the wild type amino acid sequence; and (c) one or more of the residues GRAKRAFLPGMNPPPY (SEQ ID NO:62) at positions 139-154 of SEQ ID NO:14 (corresponding to positions 115-130 of SEQ ID NO:16 and 116-131 of SEQ ID NO:18) has been substituted with at least one of (i) no amino acid; or (ii) an amino acid other than the amino acid located at the position in the wild type amino acid.

As described herein, by replacing at least one amino acid of the 36-38 region of a FGF23 polypeptide scaffold of SEQ ID NO:14 (corresponding to positions 12-14 in SEQ ID NO:16 and 13-15 in SEQ ID NO:18) with either no amino acid or a non wild type residue at least one of these positions, the ability of FGF23 to activate FGFR4 is imparted and hepatocyte mitogenicity is also imparted. By replacing one or more of the 45-50 region of a FGF23 polypeptide scaffold of SEQ ID NO:14 (corresponding to positions 21-26 in SEQ ID NO:16 and 22-27 in SEQ ID NO:18), which comprises the heparin binding β1-β2 loop and/or at least one amino acid of the 139-154 region of a FGF23 polypeptide sequence of SEQ ID NO:14 (corresponding to positions 115-130 of SEQ ID NO:16 and 116-131 of SEQ ID NO:18), which comprises the β10-β12 segment, with either no amino acid or a non-wild type residue at one or more of these positions, FGFR4 activation and hepatocyte mitogenicity of FGF23 can be further augmented.

III. Truncated Chimeric Polypeptides

N and C-terminally truncated forms of the chimeric polypeptides described herein form another aspect of the present disclosure. As used herein, the term "truncated chimeric polypeptide" refers to a chimeric polypeptide in which one or more amino acid residues have been removed from the amino-terminal (or N-terminal) end of the chimeric polypeptide, amino acid residues have been removed from the carboxyl-terminal (or C-terminal) end of the chimeric polypeptide, or one or more amino acid residues have been removed from both the amino-terminal and carboxyl-terminal ends of the chimeric polypeptide. A truncated chimeric polypeptide can be truncated, for example, by 1, 2, 3, 4, 5, 6, 7, 8, 9, 10, 11, 12, 13, 14, 15, 20 or more residues from the C-terminal end, N-terminal end or both C- and N-terminal ends of the polypeptide.

The activity of N-terminally truncated chimeric polypeptides and C-terminally truncated chimeric polypeptides can be assayed as described herein, for example by employing an in vitro ERK assay as described in Examples 2.1 and 2.2. Specific details of the in vitro assays that can be used to examine the activity of truncated chimeric polypeptides can be found in Example 2 and herein.

The activity of the truncated chimeric polypeptides disclosed herein can also be assessed in an in vivo assay as can be done for any of the chimeric polypeptides disclosed herein, for example in a BrdU incorporation assay as shown in Example 2.4, or by examining the effects of the truncated chimeric polypeptide on one or more metabolic parameters in a diseased model (e.g., ob/ob or DIO mice), or by examining the effects of a truncated chimeric polypeptide on tissues functions, such as ERK phosphorylation levels. Generally, to assess the in vivo activity of a truncated chimeric polypeptide, the truncated chimeric polypeptide can be administered to a test animal intraperitoneally. After a desired incubation period (e.g., 5, 10, 15, 20, 30, 40, 50 or 60 or more minutes), a blood sample can be drawn, and blood glucose levels can be measured and/or tissues can be harvested for subsequent analysis. Specific details of the in vivo assays that can be used to examine the activity of truncated chimeric polypeptides can be found in Example 10. In another assay, a test animal can be administered a BrdU label, subsequently sacrificed and the liver examined for BrdU incorporation and/or for observable morphological changes.

As with all chimeric polypeptides of the present disclosure, truncated chimeric polypeptides can optionally comprise an amino-terminal methionine residue, which can be introduced by directed mutation or as a result of a bacterial expression process.

The truncated chimeric polypeptides disclosed herein, and indeed all of the chimeric polypeptides disclosed herein, can be prepared as described in Example 1. Those of ordinary skill in the art, familiar with standard molecular biology techniques, can employ that knowledge, coupled with the instant disclosure, to make and use the truncated chimeric polypeptides described herein. Standard techniques can be used for recombinant DNA, oligonucleotide synthesis, tissue culture, and transformation (e.g., electroporation, lipofection). See, e.g., Sambrook et al., *Molecular Cloning: A Laboratory Manual*, supra, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The truncated chimeric polypeptides of the present invention can also be fused to another entity, which can impart additional properties to the truncated chimeric polypeptide. In one embodiment of the present invention, a truncated chimeric polypeptide can be fused to an Fc sequence as described herein. Such a fusion can be generated using known molecular biological methods and/or the guidance provided herein. The benefits of such fusion polypeptides, as well as methods for making such fusion polypeptides, are discussed in more detail herein.

IV. Chimeric Polypeptide Variants

In another aspect, chimeric polypeptide variants are provided. A chimeric polypeptide variant comprises an amino acid sequence that exhibits enhanced or decreased FGFR4-mediated signaling and is at least about 85 percent identical to the amino acid sequence of FGF19 (e.g., SEQ ID NO: 4), but wherein the specific residues comprising the modification(s) that enhance or decrease FGF19's FGFR4-mediated signaling activity have not been further modified. In other words, with the exception of residues in the chimeric polypeptide that have been modified in order to confer enhanced or decreased FGFR4-mediated signaling, about 15 percent of all other amino acid residues in the chimeric polypeptide sequence can be modified. In the particular example of a chimeric polypeptide exhibiting decreased FGFR4-mediated activity in which one or more of the residues WGDPI at positions 16-20 of the FGF19 polypeptide scaffold has been substituted with (a) no amino acid; or (b) an amino acid other than the amino acid located at the position in the wild type amino acid sequence (SEQ ID NO:4), up to 15 percent of all amino acid residues other than the residues changed at position 16-20 of the FGF19 polypeptide scaffold could be modified.

In still other embodiments, a chimeric polypeptide comprises an amino acid sequence that exhibits enhanced or decreased FGFR4-mediated signaling and that is at least about 90 percent, or about 95, 96, 97, 98, or 99 percent identical to the amino acid sequence of the polypeptide scaffold (e.g., SEQ ID NO: 4), but wherein the specific residues conferring the chimeric polypeptide's enhanced or decreased FGFR4-mediated signaling properties have not been further modified.

Also provided are nucleic acids encoding such chimeric polypeptide variants. Thus, a nucleic acid molecule encoding an amino acid sequence that exhibits enhanced or decreased FGFR4-mediated signaling and is at least about 85 percent identical to the amino acid sequence of FGF19 (e.g., SEQ ID NO: 4), but wherein the specific residues comprising the modification(s) that enhance or decrease FGF19's FGFR4-mediated signaling activity have not been further modified, is provided. In other words, with the exception of nucleotides that encode residues in the chimeric polypeptide that have been modified in order to confer decreased FGFR4-mediated signaling or other properties, nucleotides encoding about 15 percent of all other amino acids in the chimeric polypeptide can be modified. Again using the case of a chimeric polypeptide showing decreased FGFR4-mediated signaling in which one or more of the residues WGDPI at positions 16-20 of the FGF19 polypeptide scaffold has been substituted with (a) no amino acid; or (b) an amino acid other than the amino acid located at the position in the wild type amino acid sequence as an example, nucleotides encoding up to 15 percent of all amino acids other than the nucleotides encoding residues at positions 16-20 of the FGF19 polypeptide scaffold could be modified.

Also provided is a nucleic acid molecule encoding a chimeric polypeptide showing decreased FGFR4-mediated signaling and comprising an amino acid sequence that is at least about 90 percent, or about 95, 96, 97, 98, or 99 percent identical to the amino acid sequence of SEQ ID NO: 4, but wherein the specific residues comprising the modification(s) that decrease FGF19's FGFR4-mediated signaling activity have not been further modified.

V. Chimeric Fusion Polypeptides

Chimeric fusion polypeptides form another aspect of the present disclosure. As used herein, the term "chimeric fusion polypeptide" or "chimeric fusion protein" refers to a fusion of an amino acid sequence comprising one or more amino acid residues (including longer sequences such as a heterologous protein or peptide) at the N-terminus or C-terminus of any of the chimeric polypeptides disclosed herein.

Heterologous peptides and polypeptides include, but are not limited to, an epitope to allow for the detection and/or isolation of a chimeric polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region (an "Fc" domain); a functional or non-functional antibody, or a heavy or light chain thereof; and a polypeptide which has an activity, such as a therapeutic activity, different from the chimeric polypeptides of the present invention. Also encompassed by the present invention are chimeric polypeptides fused to human serum albumin (HSA).

Chimeric fusion polypeptides can be made by fusing heterologous sequences at either the N-terminus or at the C-terminus of a chimeric polypeptide. As described herein, a heterologous sequence can be an amino acid sequence or a non-amino acid-containing polymer. Heterologous sequences can be fused either directly to the chimeric polypeptide or via a linker or adapter molecule. A linker or adapter molecule can be one or more amino acid residues (or -mers), e.g., 1, 2, 3, 4, 5, 6, 7, 8, or 9 residues (or -mers), preferably from 10 to 50 amino acid residues (or -mers), e.g., 10, 11, 12, 13, 14, 15, 16, 17, 18, 19, 20, 25, 30, 35, 40, 45, or 50 residues (or -mers), and more preferably from 15 to 35 amino acid residues (or -mers). Examples of linkers include the peptides of SEQ ID NOs:63-70. A linker or adapter molecule can also be designed with a cleavage site for a DNA restriction endonuclease or for a protease to allow for the separation of the fused moieties.

V.A. Fc Fusions

In one embodiment of the present invention, a chimeric polypeptide is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas a Fab is short-lived (Capon et al., (1989) *Nature* 337: 525-31). When joined together with a therapeutic protein, an Fc domain can provide longer half-life or incorporate such functions as Fc receptor binding, protein A binding, complement fixation, and perhaps even placental transfer (Capon et al., 1989).

The resulting chimeric fusion polypeptide can be purified, for example, by the use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region can be a naturally occurring Fc region, or can be altered to improve certain qualities, such as therapeutic qualities, circulation time, or reduced aggregation.

Useful modifications of protein therapeutic agents by fusion with the "Fc" domain of an antibody are discussed in detail in International Publication No. WO 00/024782, which is hereby incorporated by reference in its entirety. This document discusses linkage to a "vehicle" such as polyethylene glycol (PEG), dextran, or an Fc region.

V.B. Fusion Protein Linkers

When forming a chimeric fusion polypeptide of the present disclosure, a linker can, but need not, be employed. When present, the linker's chemical structure may not always be critical, since it serves primarily as a spacer. The linker can be made up of amino acids linked together by peptide bonds. In some embodiments of the present invention, the linker is made up of from 1 to 20 amino acids linked by peptide bonds, wherein the amino acids are selected from the 20 naturally occurring amino acids. In various embodiments, the 1 to 20 amino acids are selected from the amino acids glycine, serine, alanine, proline, asparagine, glutamine, and lysine. In some embodiments, a linker is made up of a majority of amino acids that are sterically unhindered, such as glycine and alanine 1n some embodiments, linkers are polyglycines (such as (Gly)$_4$ (SEQ ID NO:63) and (Gly)$_5$ (SEQ ID NO:64)), polyalanines, combinations of glycine and alanine (such as poly(Gly-Ala)), or combinations of glycine and serine (such as poly(Gly-Ser)). Other suitable linkers include: (Gly)$_5$-Ser-(Gly)$_3$-Ser-(Gly)$_4$-Ser (SEQ ID NO:65), (Gly)$_4$-Ser-(Gly)$_4$-Ser-(Gly)$_4$-Ser (SEQ ID NO:66), (Gly)$_3$-Lys-(Gly)$_4$ (SEQ ID NO:67), (Gly)$_3$-Asn-Gly-Ser-(Gly)$_2$ (SEQ ID NO:68), (Gly)$_3$-Cys-(Gly)$_4$ (SEQ ID NO:69), and Gly-Pro-Asn-Gly-Gly (SEQ ID NO:70). Linkers of any length or composition can be employed in the formation of a chimeric fusion polypeptide.

The linkers described herein are exemplary, and linkers that are much longer and which include other residues are contemplated by the present invention. Non-peptide linkers are also contemplated by the present invention. For example, alkyl linkers such as —NH—(CH$_2$)$_s$—C(O)—, wherein s=2 to 20, could be used. These alkyl linkers can further be substituted by any non-sterically hindering group, including, but not limited to, a lower alkyl (e.g., C1-C6), lower acyl, halogen (e.g., Cl, Br), CN, NH$_2$, or phenyl. An exemplary non-peptide linker is a polyethylene glycol linker, wherein the linker has a molecular weight of 100 to 5000 kD, for example, 100 to 500 kD.

VI. Chemically Modified Chimeric Polypeptides

Chemically modified forms of the chimeric polypeptides described herein, including their truncated forms, can be prepared by one skilled in the art, using the present disclosure coupled with techniques known in the art. Such chemically modified chimeric polypeptides are altered such that the chemically modified chimeric polypeptide is different from the unmodified chimeric polypeptide, either in the type or location of the molecules naturally attached to the chimeric polypeptide. Chemically modified chimeric polypeptides can include molecules formed by the deletion of one or more naturally-attached chemical groups.

In one embodiment, chimeric polypeptides of the present invention can be modified by the covalent attachment of one or more polymers. For example, the polymer selected is often water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable. Non-water soluble polymers conjugated to the chimeric polypeptides of the present disclosure also form an aspect of the invention.

Exemplary polymers each can be of any molecular weight and can be branched or unbranched. The polymers each typically have an average molecular weight of between about 2 kDa to about 100 kDa (the term "about" indicating that in preparations of a water-soluble polymer, some molecules will weigh more and some less than the stated molecular weight). The average molecular weight of each polymer is preferably between about 5 kDa and about 50 kDa, more preferably between about 12 kDa and about 40 kDa, and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-(C$_1$-C$_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that can be used to prepare covalently attached chimeric polypeptides multimers. Also encompassed by the present invention are chimeric polypeptides covalently attached to polysialic acid.

In some embodiments of the present invention, a chimeric polypeptide is covalently, or chemically, modified to include one or more water-soluble polymers, including, but not limited to, polyethylene glycol (PEG), polyoxyethylene glycol, or polypropylene glycol. See, e.g., U.S. Pat. Nos. 4,640,835; 4,496,689; 4,301,144; 4,670,417; 4,791,192; and 4,179,337. In some embodiments of the present invention, a chimeric polypeptide comprises one or more polymers, including, but not limited to, monomethoxy-polyethylene glycol, dextran, cellulose, another carbohydrate-based polymer, poly-(N-vinyl pyrrolidone)-polyethylene glycol, propylene glycol homopolymers, a polypropylene oxide/ethylene oxide copolymer, polyoxyethylated polyols (e.g., glycerol), polyvinyl alcohol, or mixtures of such polymers.

In some embodiments of the present invention, a chimeric polypeptide is covalently-modified with PEG subunits. In other embodiments, one or more water-soluble polymers are bonded at one or more specific positions (for example, at the N-terminus) of the chimeric polypeptide. In still other embodiments, one or more water-soluble polymers are randomly attached to one or more side chains of a chimeric polypeptide. In some embodiments, PEG is used to improve the therapeutic capacity of a chimeric polypeptide. Certain such methods are discussed, for example, in U.S. Pat. No. 6,133,426, which is hereby incorporated by reference for any purpose.

In embodiments of the present invention wherein the polymer is PEG, the PEG group can be of any convenient molecular weight, and can be linear or branched. The average molecular weight of the PEG group will preferably range from about 2 kD to about 100 kDa, and more preferably from about 5 kDa to about 50 kDa, e.g., 10, 20, 30, 40, or 50 kDa. The PEG groups will generally be attached to the chimeric polypeptide via acylation or reductive alkylation through a reactive group on the PEG moiety (e.g., an aldehyde, amino, thiol, or ester group) to a reactive group on the chimeric polypeptide (e.g., an aldehyde, amino, or ester group).

The PEGylation of a polypeptide, including the chimeric polypeptides of the present invention, can be specifically carried out using any of the PEGylation reactions known in the art. Such reactions are described, for example, in the following references: Francis et al., (1992), *Focus on Growth Factors* 3: 4-10; European Patent Nos. 0 154 316 and 0 401 384; and U.S. Pat. No. 4,179,337. For example, PEGylation can be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono C$_1$-C$_{10}$ alkoxy or aryloxy derivatives thereof (see, e.g., U.S. Pat. No. 5,252,714).

In some embodiments of the present invention, a useful strategy for the attachment of the PEG group to a polypeptide involves combining, through the formation of a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water-soluble polymer that can be used for protein modification. Therefore, the chimeric polypeptides of the present invention fused to a polysaccharide polymer form embodiments of the present invention. Dextrans are polysaccharide polymers comprised of individual subunits of glucose predominantly linked by alpha 1-6 linkages. The dextran itself is available in many molecular weight ranges, and is readily available in molecular weights from about 1 kD to about 70 kD. Dextran is a suitable water-soluble polymer for use as a vehicle by itself or in combination with another vehicle (e.g., a Fc). See, e.g., International Publication No. WO 96/11953. The use of dextran conjugated to therapeutic or diagnostic immunoglobulins has been reported. See, e.g., European Patent Publication No. 0 315 456, which is hereby incorporated by reference. The present invention also encompasses the use of dextran of about 1 kD to about 20 kD.

In general, chemical modification can be performed under any suitable condition used to react a protein with an activated polymer molecule. Methods for preparing chemically modified polypeptides will generally comprise the steps of: (a) reacting the polypeptide with the activated polymer molecule (such as a reactive ester or aldehyde derivative of the polymer molecule) under conditions whereby a chimeric polypeptide becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment of the present invention, chemically modified chimeric polypeptides can have a single polymer molecule moiety at the amino-terminus (see, e.g., U.S. Pat. No. 5,234,784)

In another embodiment of the present invention, chimeric polypeptides can be chemically coupled to biotin. The biotin/chimeric polypeptides are then allowed to bind to avidin, resulting in tetravalent avidin/biotin/chimeric polypeptides. Chimeric polypeptides can also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that can be alleviated or modulated by the administration of the present chemically modified chimeric polypeptides include those described herein for chimeric polypeptides. However, the chemically modified chimeric polypeptides disclosed herein can have additional activities, enhanced or reduced biological activity, or other characteristics, such as increased or decreased half-life, as compared to unmodified chimeric polypeptides.

VII. Pharmaceutical Compositions

Therapeutic compositions comprising the disclosed chimeric polypeptides are within the scope of the present disclosure, and are specifically contemplated in light of the identification of several chimeric polypeptides exhibiting desirable properties. Such chimeric polypeptide pharmaceutical compositions can comprise a therapeutically effective amount of a chimeric polypeptide in admixture with a pharmaceutically or physiologically acceptable formulation agent (e.g., a carrier, formulation material, etc) selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., *Remington's Pharmaceutical Sciences* (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage (see, e.g., *Remington's Pharmaceutical Sciences*, supra). Such compositions can influence the physical state, stability, rate of in vivo release, and rate of in vivo clearance of the chimeric polypeptide.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the present disclosure, chimeric polypeptide compositions can be prepared for storage by mixing the selected composition having the desired degree of purity with optional formulation agents (*Remington's Pharmaceutical Sciences*, supra) in the form of a lyophilized cake or an aqueous solution. Further, the chimeric polypeptide product can be formulated as a lyophilizate using appropriate excipients such as sucrose.

The chimeric polypeptide pharmaceutical compositions can be selected for parenteral delivery. Alternatively, the compositions can be selected for inhalation or for delivery through the digestive tract, such as orally. The preparation of such pharmaceutically acceptable compositions is known to those of skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising the desired chimeric polypeptide in a pharmaceutically acceptable vehicle. A particularly suitable vehicle for parenteral injection is sterile distilled water in which a chimeric polypeptide is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a chimeric polypeptide can be formulated as a dry powder for inhalation. Chimeric polypeptide inhalation solutions can also be formulated with a propellant for aerosol delivery. In yet another embodiment, solutions can be nebulized. Pulmonary administration is further described in International Publication No. WO 94/20069, which describes the pulmonary delivery of chemically modified proteins.

It is also contemplated that certain formulations can be administered orally. In one embodiment of the present invention, chimeric polypeptides that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the chimeric polypeptide. Diluents, flavorings, low melting point waxes, vegetable oils, lubricants, suspending agents, tablet disintegrating agents, and binders can also be employed.

Another pharmaceutical composition can involve an effective quantity of chimeric polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional chimeric polypeptide pharmaceutical compositions will be evident to those skilled in the art, including formulations comprising chimeric polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO 93/15722, which describes the controlled release of porous polymeric microparticles for the delivery of pharmaceutical compositions, and Wischke & Schwendeman, (2008) *Int. J. Pharm.* 364:298-327, and Freiberg & Zhu, (2004) *Int. J. Pharm.* 282:1-18, which discuss microsphere/microparticle preparation and use).

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et al., (1983) *Biopolymers* 22: 547-56), poly(2-hydroxyethyl-methacrylate) (Langer et al., (1981) *J. Biomed. Mater. Res.* 15: 167-277 and Langer, 1982, *Chem. Tech.* 12: 98-105), ethylene vinyl acetate (Langer et al., supra) or poly-D(−)-3-hydroxybutyric acid (European Patent No. 0 133 988). Sustained-release compositions can also include liposomes, which can be prepared by any of several methods known in the art. See, e.g., Epstein et al., (1985) *Proc. Natl. Acad. Sci. U.S.A.* 82: 3688-92; and European Patent Nos. 0 036 676, 0 088 046, and 0 143 949.

The chimeric polypeptide pharmaceutical composition to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In a specific embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

The effective amount of a chimeric polypeptide pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the chimeric polypeptide is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg; or 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, up to about 100 mg/kg. In yet other embodiments, the dosage can be 50 µg/kg, 100 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850

μg/kg, 900 μg/kg, 950 μg/kg, 100 μg/kg, 200 μg/kg, 300 μg/kg, 400 μg/kg, 500 μg/kg, 600 μg/kg, 700 μg/kg, 800 μg/kg, 900 μg/kg, 1000 μg/kg, 2000 μg/kg, 3000 μg/kg, 4000 μg/kg, 5000 μg/kg, 6000 μg/kg, 7000 μg/kg, 8000 μg/kg, 9000 μg/kg, 10 mg/kg or more.

The frequency of dosing will depend upon the pharmacokinetic parameters of the chimeric polypeptide in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

VIII. Therapeutic and Other Uses of a Chimeric Polypeptide

Chimeric polypeptides can be used to treat, diagnose, ameliorate, or prevent a number of diseases, disorders, or conditions, including, but not limited to metabolic disorders and oncology-related disorders. In one embodiment, the metabolic disorder to be treated is diabetes, e.g., type 2 diabetes. In another embodiment, the metabolic disorder is obesity. Other embodiments include metabolic conditions or disorders such as dyslipidimia; hypertension; hepatosteaotosis, such as nonalcoholic steatohepatitis (NASH); cardiovascular disease, such as atherosclerosis; and aging. In another embodiment the oncology-related disorder is a form of cancer.

In application, a disorder or condition such as diabetes or obesity can be treated by administering a chimeric polypeptide as described herein to a patient in need thereof in the amount of a therapeutically effective dose. The administration can be performed as described herein, such as by IV injection, intraperitoneal injection, intramuscular injection, or orally in the form of a tablet or liquid formation. In most situations, a desired dosage can be determined by a clinician, as described herein, and can represent a therapeutically effective dose of the chimeric polypeptide. It will be apparent to those of skill in the art that a therapeutically effective dose of a given chimeric polypeptide will depend, inter alia, upon the administration schedule, the unit dose of antigen administered, whether the nucleic acid molecule or polypeptide is administered in combination with other therapeutic agents, the immune status and the health of the recipient. The term "therapeutically effective dose," as used herein, means that amount of a given chimeric polypeptide that elicits the biological or medicinal response in a tissue system, animal, or human being sought by a researcher, medical doctor, or other clinician, which includes alleviation of the symptoms of a disease or disorder being treated.

IX. Antigen Binding Proteins

As used herein, an antigen binding protein is a protein comprising a portion that binds to an antigen and, optionally, a scaffold or framework portion that allows the antigen binding portion to adopt a conformation that promotes binding of the antigen binding protein to the antigen. Examples of antigen binding proteins include human antibody, a humanized antibody; a chimeric antibody; a recombinant antibody; a single chain antibody; a diabody; a triabody; a tetrabody; a Fab fragment; a F(ab')2 fragment; an IgD antibody; an IgE antibody; an IgM antibody; an IgG1 antibody; an IgG2 antibody; an IgG3 antibody; or an IgG4 antibody, and fragments thereof. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, e.g., Korndorfer et al., 2003, *Proteins: Structure, Function, and Bioinformatics*, 53(1):121-129 (2003); Roque et al., *Biotechnol. Prog.* 20:639-654 (2004). In addition, peptide antibody mimetics ("PAMs") can be used, as well as scaffolds based on antibody mimetics utilizing fibronectin components as a scaffold.

Antigen binding proteins that specifically bind to the chimeric polypeptides of the present invention but do not specifically bind to wild-type polypeptide scaffolds are contemplated and are within the scope of the present disclosure. An antigen binding protein (e.g., an antibody) is said to "specifically bind" its target antigen when the dissociation constant ($K_D$) is $\leq 10^{-8}$ M. The antibody specifically binds antigen with "high affinity" when the $K_D$ is $\leq 5 \times 10^{-9}$ M, and with "very high affinity" when the $K_D$ is $\leq 5 \times 10^{-10}$ M.

When an antigen binding protein is an antibody, the antibody can be polyclonal, including monospecific polyclonal; monoclonal (MAbs); recombinant; chimeric; humanized, such as complementarity-determining region (CDR)-grafted; human; single chain; and/or bispecific; as well as fragments; variants; or chemically modified molecules thereof. Antibody fragments include those portions of the antibody that specifically bind to an epitope on a chimeric polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a chimeric polypeptide generally are produced in animals (e.g., rabbits or mice) by means of multiple subcutaneous or intraperitoneal injections of the chimeric polypeptide and an adjuvant. It can be useful to conjugate a chimeric polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-chimeric polypeptide antibody titer.

Monoclonal antibodies directed toward chimeric polypeptides can be produced using any method that provides for the production of antibody molecules by continuous cell lines in culture. Examples of suitable methods for preparing monoclonal antibodies include the hybridoma methods of Kohler et al., 1975, *Nature* 256: 495-97 and the human B-cell hybridoma method (Kozbor, 1984, *J. Immunol.* 133: 3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with chimeric polypeptides.

The anti-chimeric polypeptide antibodies of the invention can be employed in any known assay method, such as competitive binding assays, direct and indirect sandwich assays, and immunoprecipitation assays (see, e.g., Sola, *Monoclonal Antibodies: A Manual of Techniques* 147-158, CRC Press, Inc., 1987), incorporated herein by reference in its entirety) for the detection and quantitation of chimeric polypeptide polypeptides. The antibodies will bind chimeric polypeptides with an affinity that is appropriate for the assay method being employed.

For diagnostic applications, in certain embodiments, anti-chimeric polypeptide antibodies can be labeled with a detectable moiety. The detectable moiety can be any one that is capable of producing, either directly or indirectly, a detectable signal. For example, the detectable moiety can be a radioisotope, such as $^{3}H$, $^{14}C$, $^{32}P$, $^{35}S$, $^{125}I$, $^{99}Tc$, $^{111}In$, or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase (Bayer et al., (1990) *Meth. Enz.* 184: 138-63).

Competitive binding assays rely on the ability of a labeled standard (e.g., a chimeric polypeptide, or an immunologically reactive portion thereof) to compete with the test sample analyte (e.g., a chimeric polypeptide) for binding with a limited amount of anti-chimeric polypeptide antibody. The amount of a chimeric polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies can conveniently be separated from the standard and analyte that remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody that is immobilized on a solid support, and thereafter a second antibody binds to the analyte, thus forming an insoluble three-part complex. See, e.g., U.S. Pat. No. 4,376,110. The second antibody can itself be labeled with a detectable moiety (direct sandwich assays) or can be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The anti-chimeric polypeptide antibodies of the present invention are also useful for in vivo imaging. An antibody labeled with a detectable moiety can be administered to an animal, preferably into the bloodstream, and the presence and location of the labeled antibody in the host assayed. The antibody can be labeled with any moiety that is detectable in an animal, whether by nuclear magnetic resonance, radiology, or other detection means known in the art.

The invention also relates to a kit comprising anti-chimeric polypeptide antibodies and other reagents useful for detecting chimeric polypeptide levels in biological samples. Such reagents can include a detectable label, blocking serum, positive and negative control samples, and detection reagents. Such a kit can further comprise a set of instructions indicating how the reagents and kit can be used.

EXAMPLES

The Examples that follow are illustrative of specific embodiments of the invention, and various uses thereof. They are set forth for explanatory purposes only, and should not be construed as limiting the scope of the disclosed invention in any way.

Example 1

Expression and Purification of Recombinant Scaffold Polypeptides and Chimeric Proteins Nucleotide sequences encoding wild type FGF19 without the secretory leader peptide (residues 23-216, SEQ ID NO:4) and chimeric polypeptides were cloned into the pET30 vector (Novagen). Briefly, nucleotides for wild type FGF19 and chimeric polypeptides were generated through polymerase chain reaction (PCR), both PCR products and pET30 vector were digested with restriction enzyme Nde I and BamH I and ligated with ligase. DNA constructs were transformed into BL21 (DE3) *E. coli* (Novagen). Protein expression was induced with IPTG at 37° C. The purification process was the same as previously described (Wu et al., (2008) *J. Biol. Chem.* 283:33304-9). FGF21 without the secretory leader peptide, (residues 29-209, SEQ ID NO:10) was purified as previously described (Xu et al., (2008) *Diabetes* 58:250-59).

A description of some of the polypeptides that were generated is shown in Table 2:

TABLE 2

| Sequence Identifier | Composition of Sequence | SEQ ID NO: NT | SEQ ID NO: PP |
|---|---|---|---|
| FGF19 | hFGF19 | 1 | 2 |
| Mature FGF19 | hFGF19 lacking signal sequence | 3 | 4 |
| Mature FGF19 + N-terminal Met | hFGF19 lacking signal sequence with N-terminal Met added | 5 | 6 |
| FGF21 | hFGF21 | 7 | 8 |
| Mature FGF21 | hFGF21 lacking signal sequence | 9 | 10 |
| Mature FGF21 + N-terminal Met | hFGF21 lacking signal sequence with N-terminal Met added | 11 | 12 |
| FGF23 | hFGF23 | 13 | 14 |
| Mature FGF23 | hFGF23 lacking signal sequence | 15 | 16 |
| Mature FGF23 + N-terminal Met | hFGF23 lacking signal sequence with N-terminal Met added | 17 | 18 |
| FGF19dCTD | M::hFGF19(23-177) | 19 | 20 |
| FGF19/21-1 | M::hFGF19(23-80)::hFGF21(82-209) | 21 | 22 |
| FGF19/21-2 | M::hFGF19(23-49)::hFGF21(52-209) | 23 | 24 |

TABLE 2-continued

| Sequence Identifier | Composition of Sequence | SEQ ID NO: NT | SEQ ID NO: PP |
|---|---|---|---|
| FGF19/21-3 | M::hFGF19(23-42)::hFGF21(45-209) | 25 | 26 |
| FGF19/21-4 | M::hFGF19(23-37)::hFGF21(42-209) | 27 | 28 |
| FGF19/21-5 | M::hFGF19(23-32)::hFGF21(37-209) | 29 | 30 |
| FGF21/19$^{38-42}$ | M::hFGF21(29-41)::hFGF19(38-42)::hFGF21(45-209) | 31 | 32 |
| FGF19/21$^{42-44}$ | M::hFGF19(23-37)::hFGF21(42-44)::hFGF19(43-216) | 33 | 34 |
| FGF19-1 | M::hFGF19(23-49)::hFGF21(52-58)::hFGF19(58-216) | 35 | 36 |
| FGF19-2 | M::hFGF19(23-145)::hFGF21(147-161)::hFGF19(163-216) | 37 | 38 |
| FGF19-3 | M::hFGF19(23-49)::hFGF21(52-58)::hFGF19(58-145)::hFGF21(147-161)::hFGF19(163-216) | 39 | 40 |
| FGF19-4 | M::hFGF19(23-37)::hFGF21(42-44)::hFGF19(43-49)::hFGF21(52-58)::hFGF19(58-216) | 41 | 42 |
| FGF19-5 | M::hFGF19(23-37)::hFGF21(42-44)::hFGF19(43-145)::hFGF21(148-162)::hFGF19(163-216) | 43 | 44 |
| FGF19-6 | M::hFGF19(23-37)::hFGF21(42-44)::hFGF19(43-49)::hFGF21(52-58)::hFGF19(58-145)::hFGF21(148-162)::hFGF19(163-216) | 45 | 46 |

In Table 2, each construct is presented in the N to C terminal direction; "M" indicates an N-terminal methionine, hFGF19 (X-Y) indicates a region of human FGF19 stretching between residue X and residue Y of a wild type FGF19 amino acid sequence, and hFGF21 (X-Y) indicates a region of human FGF21 stretching between residue X and residue Y of a wild type FGF21 amino acid sequence. For example, in the case of FGF19/21-1 in Table 2, this sequence comprises M::hFGF19 (23-80)::hFGF21 (82-209) means sequence is composed of methionine, followed by human FGF19 sequences 23 to 80, then followed by human FGF21 sequences 82 to 209.

Example 2

Experimental Methods

The following experimental methods were employed in Examples 3-10.

2.1 Western-Blot Analysis of FGF Signaling

L6 cells were maintained in Dulbecco's modified Eagle's medium supplemented with 10% fetal bovine serum and penicillin/streptomycin. Cells were transfected with expression vectors using the Lipofectamine 2000 transfection reagent (Invitrogen) according to the manufacturer's protocol.

Analysis of FGF signaling in L6 cells were performed as described before. Cell cultures were collected 10 min after the treatment of FGF19 or chimeras and snap frozen in liquid nitrogen, homogenized in the lysis buffer and subjected to western blot analysis using anti-phospho-p44/42 MAP kinase (ERK1/2) antibody and anti-ERK antibody (Cell Signaling).

2.2 MSD Assay for FGF Signaling

L6 cells plated in 24 well plates ($10^6$ cells/well) were transfected with various FGF receptors, including FGFR1c and FGFR4 and αKlotho or βKlotho and serum starved in 0.2% bovine serum albumin overnight before FGF treatment. Media was aspirated after 10 min and plates were snap frozen in liquid nitrogen. Cells in each well were lysed in 60 μl of complete lysis buffer and total and phosphorylated ERK was measured using MSD whole cell lysate Phospho-ERK1/2 kit (Meso Scale Discovery, Gaithersburg, Md.) according to the manufacturer's instructions.

2.3 Glucose Uptake Assay

3T3L1 preadipocytes (ATCC CL-173) were cultured and induced to differentiate. Glucose uptake was assayed as described in Kharitonenkov, et al., (2005) *J Clin Invest* 115, 1627-1635.

2.4 In Vivo Hepatocyte BrdU Labeling Assay

For all BrDU studies described herein, on day 1 of the study an osmotic minipump (ALZET®, model 1007D) containing 5-bromo-2'-deoxyuridine (BrdU; Sigma Chemical Co., St. Louis, Mo.) (16 mg/mL) was implanted subcutaneously into each of 7-10 8 week-old female FVB mouse (Charles River Laboratories, Charles River, Mass.). Each mouse was given an IP injection of either phosphate-buffered saline (PBS; vehicle), or various proteins as indicated daily at 2 mg/kg/day beginning on day 2 of the study and continuing for 6 consecutive days. Samples of liver and duodenum were collected from each mouse on the day following the last IP injection and placed in 10% neutral-buffered formalin in preparation for paraffin-embedding, sectioning, and light microscopic evaluation. Sections of all collected tissues were stained by an immunohistochemical method described herein to visualize BrdU incorporation as a marker of mitotic activity. Tissue sections were examined at random by routine light microscopy without knowledge of treatment group. The number of hepatocyte nuclei stained for BrdU incorporation was assigned a score on a semiquantitative scale where 0=no increase above expected levels in vehicle-treated (control) mice and ±=equivocal, 1=minimal, 2=mild, 3=moderate, and 4=marked increase above control levels. The localization (centrilobular or diffusely scattered through hepatic lobules) of the hepatocytes stained for BrdU incorporation was also recorded.

Cellular incorporation of BrdU was detected by digesting deparaffinized tissue sections with 0.1% Protease (Sigma, St. Louis, Mo.) and treating the sections with 2N hydrochloric acid. Sections were blocked with CAS BLOCK (Zymed Laboratories, San Francisco, Calif.), incubated with rat antibody to BrdU (Accurate, Westbury, N.Y.; catalog no. OBT0030, lot no. H9180), and bound rat antibody was detected with biotinylated rabbit antibody to rat IgG (Vector Laboratories, Burlingame, Calif.; catalog no. BA 4001, lot no. S0907). Tissue sections were quenched with Peroxidase Blocking Solution (DAKO Corp., Carpinteria, Calif.) and retained biotin was detected with Vectastain Elite ABC kit (Vector Laboratories). Reaction sites were visualized with DAB+Substrate-Chromagen System (DAKO Corp.). Sections were counterstained with hematoxylin.

Example 3

FGF21 Does not Increase Hepatocyte Proliferation In Vivo

Because FGF21 is in the same subfamily with FGF19, and both show significant similarities in receptor/co-receptor requirements and in regulation of glucose and lipid metabolism, the effects of each on hepatocyte proliferation was studied. Using in vivo BrdU labeling, enhanced hepatocyte proliferation around the central vein was observed in FGF19 transgenic animals as well as in nontransgenic animals 6 days post daily injection of recombinant FGF19 protein. See, Nicholes et al., (2002) *Am J Pathol* 160, 2295-2307. Using a similar BrdU labeling method, we examined the effects of FGF21 treatment on hepatocyte proliferation and compared its activity to that of FGF19. As shown in FIG. 1A, histopathological examination of the liver sections from FGF19 treated animals showed increased BrdU labeled hepatocytes concentrating in centrilobular regions of hepatic lobules, consistent with published observations (see, e.g., Nicholes et al., (2002) *Am J Pathol* 160, 2295-2307). In contrast, livers from FGF21 treated animals did not show increased numbers of BrdU-labeled hepatocytes in pericentral regions, nor was increased BrdU labeling noted in any other area of the liver, suggesting that FGF21 did not enhance hepatocyte proliferation under the conditions tested and, therefore, is distinct from FGF19. FIG. 1B graphically depicts the incorporation level of the BrdU label at the conclusion of the experiment, and highlights the observation that FGF19 led to BrdU incorporation, while the PBS control and FGF21 did not.

Example 4

FGF19, but not FGF21, Activates FGFR4 Mediated ERK Phosphorylation, and Selective Activation of FGFR4 in Liver Induces Pericentral Hepatocyte Proliferation To better understand the mechanism for FGF19 induced hepatocyte proliferation and its differences from FGF21, the receptor and co-receptor requirements between FGF19 and FGF21 were first compared. The rat myoblast cell line L6, which expresses very low levels of endogenous FGF receptors, was transfected with FGFR1c, 2c, 3c or 4 together with βKlotho. Receptor activation was determined by Western blot analysis of phospho-ERK levels in treated cells. As shown in FIGS. 2A-2D, while both FGF19 and FGF21 were able to activate FGFR1c (FIG. 2A), 2c (FIG. 2B), and 3c (FIG. 2C), only FGF19 and not FGF21 induced ERK phosphorylation via FGFR4 (FIG. 2D) (see, e.g., Kurosu et al., (2007) *J. Biol. Chem.* 282, 26687-26695, and Lin et al., (2007) *J. Bio. Chem.* 282, 27277-27284). Given that FGFR4 is the predominant receptor expressed in hepatocytes, the effect of FGFR4 activation as measured by ERK phosphorylation on the enhanced hepatocyte proliferation observed in FGF19 treated animals was studied.

In this experiment a variant of FGF19, FGF19dCTD, identified as a selective FGFR4 agonist, was employed. As illustrated in FIG. 3A, FGF19dCTD is a truncated form of FGF19 in which the C-terminal residues 178-216 have been removed. Because this region is critical for co-receptor βKlotho interaction, FGF19dCTD cannot activate FGFRs 1c, 2c, and 3c which depend on βKlotho for activation by both FGF19 and FGF21 (FIG. 3B; see also Wu et al., (2008) *J. Biol. Chem.* 283(48):33304-9). FGF19dCTD can, however, still activate FGFR4 both in vitro (FIG. 3B) and in vivo. Accordingly FGF19dCTD was employed to examine the effects of selective FGFR4 activation on hepatocyte proliferation. Analysis of BrdU immunostained liver sections from FGF19dCTD treated animals also showed enhanced BrdU labeling indicating increased mitotic activity almost as defined as was observed in animals treated with wild type FGF19. Thus, activation of FGFR4 alone can be sufficient to cause increased hepatocyte proliferation.

Example 5

Identification of a Region of FGF19 that is Critical for FGFR4 Activation

Upon consideration of the results shown in Example 4, the region(s) of FGF19 responsible for FGFR4 signaling were identified and studied. Because FGF19 and FGF21 share significant sequence homology but differ in the ability to activate FGFR4 signaling, chimeric proteins comprising regions of FGF19 and FGF21 were generated. The approach taken was to sequentially replace regions of an FGF21 wild type sequence with regions of FGF19, in order to identify the region responsible for FGFR4 activity.

Figure 4C:
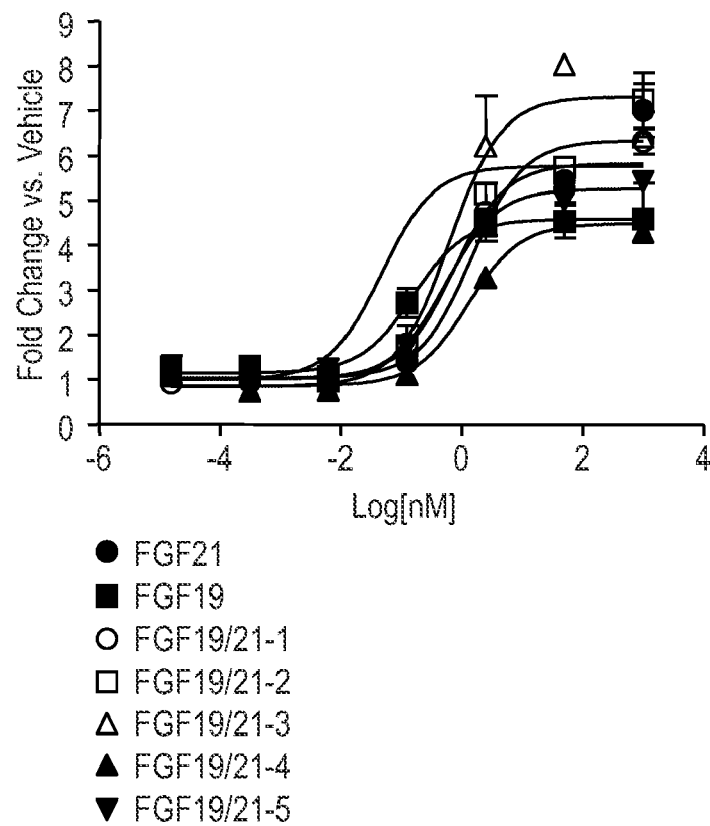
FIG. 4C is a plot showing the effect of the FGF19/21-1, FGF19/21-2, FGF19/21-3, FGF19/21-4 and FGF19/21-5 chimeric polypeptides on glucose uptake.

Results from experiments using FGF19dCTD indicated that the C-terminal region of FGF19 is not essential for FGFR4 activation; therefore, a series of FGF19/FGF21 chimeric polypeptides was generated which sequentially replaced the N-terminal region of FGF21 with the corresponding region of FGF19; these chimeric polypeptides are illustrated graphically in FIG. 4A. The properties of these chimeric polypeptides were then assessed in in vitro receptor activity assays, adipocyte glucose uptake assays, and in vivo hepatocyte proliferation assays. As shown in the top panel of FIG. 4B, all the chimeric polypeptides activated ERK phosphorylation in L6 cells transfected with FGFR1c and βKlotho. Consistently, because FGFR1c is the predominant receptor expressed in adipocytes, all the chimeric polypeptides induced glucose uptake in differentiated mouse 3T3-L1 adipocytes with similar potency and efficacy (see FIG. 4C). These results suggest that all the chimeric polypeptides are functional, and that fusions between FGF19 and FGF21 yielded properly folded and active proteins.

These chimeric polypeptides, however, displayed differences in FGFR4 selective assays. For example, in L6 cells transfected with FGFR4 and βKlotho, ERK-phosphorylation was only observed with the chimeric polypeptides FGF19/21-1, FGF19/21-2 and FGF19/21-3, which share FGF19 residues 23-42 (FIG. 4B). ERK-phosphorylation was not observed with FGF19/21-4 or FGF19/21-5, which comprise shorter N-terminal fragments derived from FGF19 (FIG. 4B, bottom panel). These results indicate that critical FGFR4 activating residues are contained within FGF19 residues 38 to 42.

Figure 4D:
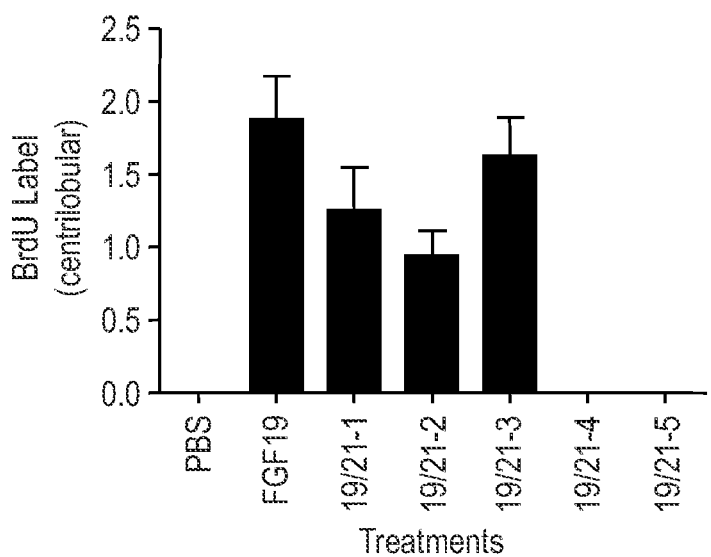
FIG. 4D is a bar graph depicting incorporation of BrdU by the FGF19/21-1, FGF19/21-2, FGF19/21-3, FGF19/21-4 and FGF19/21-5 chimeric polypeptides.

The effects of these chimeric polypeptides on hepatocyte proliferation were then tested in an in vivo BrdU incorporation assay. Examination of BrdU immunostained liver sections from treated animals showed that, like FGF19, the chimeric polypeptides FGF19/21-1, FGF19/21-2, FGF19/21-3, and FGF19/21-4 all exhibited increased BrdU labeling in the pericentral hepatocytes, however, such increases were not observed with animals treated with FGF19/21-5 and FGF19/21-6 (FIG. 4D). Therefore, BrdU labeling correlated directly with each molecule's ability to activate FGFR4 mediated ERK phosphorylation (as shown in FIG. 4A).

Example 6

Figure 5A:
FIG. 5A is a graphical depiction of the chimeric polypeptide with FGF21 shown in gray and FGF19 in white.
Figure 5B:
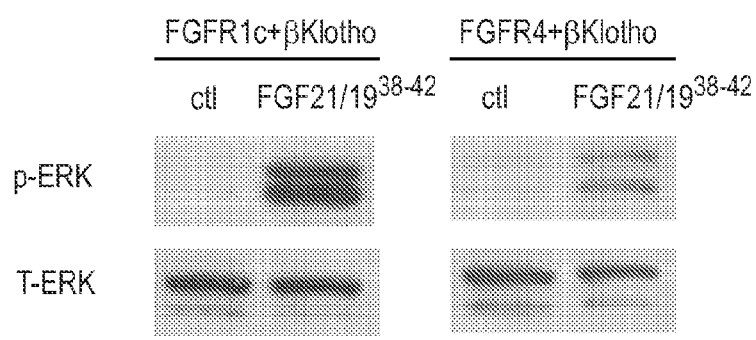
FIG. 5B is a series of Western blots showing FGFR1c and FGFR4-mediated activity of the chimeric FGF21/19$^{38\text{-}42}$ polypeptide.
Figure 5C:
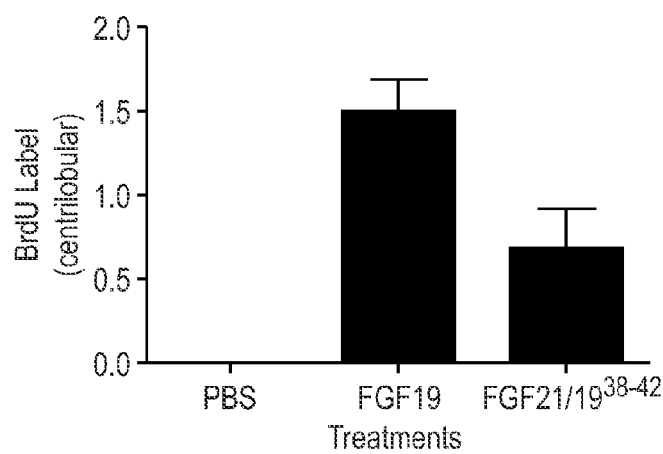
FIG. 5C is a bar graph depicting incorporation of BrdU by the chimeric FGF21/19$^{38\text{-}42}$ polypeptide.

Residues 38-42 of FGF19 Confer FGFR4Activation and Increased Hepatocyte Proliferation A comparison between FGF19/21-4 (containing the first 15 residues from a mature wild type FGF19 polypeptide) and FGF19/21-5 (containing the first 10 residues from a mature wild type FGF19 polypeptide) revealed a difference in each chimeric polypeptide's ability to activate FGFR4 and to induce hepatocyte proliferation. Because the two chimeric polypeptides only differ by 5 amino acids, a study was undertaken to determine whether these 5 residues, namely the residues at positions 38-42 a full length FGF19 (residues 16-20 in the mature form) were sufficient to confer FGFR4 activation. Another chimeric polypeptide designated "FGF21/19$^{38-42}$" (SEQ ID NO:32), comprising a FGF21 scaffold, in which residues 38-42 of a full length wild type FGF19 amino acid sequence (residues 16-20 in the mature form) replaced residues 42-44 of a full length FGF21 (residues 14-16 in the mature form), was constructed and is depicted graphically in FIG. 5A. Similar to FGF19 and FGF21, FGF21/19$^{38-42}$ induced ERK-phosphorylation in L6 cells transfected with FGFR1c and βKlotho (FIG. 5B) and was active in adipocyte glucose uptake assays. Similar to FGF19, however in contrast to FGF21, the FGF21/19$^{38-42}$ chimeric polypeptide induced ERK-phosphorylation in L6 cells transfected with FGFR4 and βKlotho (FIG. 5B). Histopathological examination analysis of liver sections from FGF21/19$^{38-42}$ treated animals showed enhanced BrdU labeling in pericentral hepatocytes similar to FGF19 treatment, distinct from FGF21 (FIG. 5C). These results indicate that introduction of these 5 residues from FGF19 conferred a gain-of-function phenotype on FGF21 with respect to FGFR4 activation in vitro and induction of hepatocyte proliferation in vivo.

Example 7

Replacing Residues 38-42 from FGF19 does not Completely Abolish FGFR4 Activation and Hepatocyte Proliferation Using a FGF19 C-terminal truncation variant and novel FGF19/FGF21 chimeric molecules, it was determined that hepatocyte FGFR4 activation measured by ERK phosphorylation may lead to increased hepatocyte proliferation. In side-by-side direct comparison studies, it was also determined that FGF21 is different from FGF19 and it lacks the ability to activate FGFR4 and does not induce hepatocyte proliferation as measured using in vivo BrdU labeling. In addition, these observations demonstrated the importance of the FGF19 N-terminal region to FGFR4 activation, and identified residues 38-42 of full length FGF19 to be sufficient to confer FGFR4 activation and to increase hepatocyte proliferation, as a construct in which the replacement of the corresponding region in FGF21 with these 5 amino acid residues (the construct designated FGF21/19$^{38-42}$ in FIG. 6A) provided gain-of-function activity to FGF21 in the form of FGFR4 activation and induction of increased hepatocyte proliferation (FIG. 6A). Additionally, the issue of whether the mutations in this region of FGF19 would abolish FGF19's ability to activate FGFR4 and eliminate its ability to induce hepatocyte proliferation was studied.

The alignment of FGF19, FGF21 and FGF23 around these 5 amino acid residues is shown in FIG. 6B. These 5 residues are underlined in FGF19 sequence, the corresponding region in FGF23 contains only 3 amino acids, WGG, and similarly, the corresponding region of FGF21 contains only 3 amino acids, $G^{42}Q^{43}V^{44}$. A construct comprising the swap of this region between FGF19 and FGF21 was constructed as shown in FIG. 6A. For FGF21/19$^{38-42}$, as described previously, the residues GQV at positions 42-44 in full length FGF21 (positions 14-16 in mature FGF21) were replaced with the corresponding FGF19 residues WGDPI (SEQ ID NO:49) at positions 38-42 of full length FGF19 (positions 16-20 of mature FGF19); and for FGF19/21$^{42-44}$ (SEQ ID NO:34), which is the reverse swap, the residues WGDPI at positions 38-42 in full length FGF19 (positions 16-20 in mature FGF19) were replaced with the corresponding residues GQV found at positions 42-44 of full length FGF21 (positions 14-16 of mature FGF21). If this region is the only region that contributes to FGFR4 activation, the substitution of FGF21 sequence into FGF19 would abolish that activity.

To test the activities of these chimeric FGF molecules in receptor activation assay, the previously described rat myoblast cell line L6, which expresses negligible levels of endogenous FGF receptors and βKlotho, was utilized. FGFRs were either transfected alone or together with βKlotho, and the signaling was monitored by the ERK phosphorylation levels (Wu et al., (2008) J. Biol. Chem. 283(48):33304-9). In this assay format, FGF19/21$^{42-44}$ still activated FGFR4 signaling in the presence of co-receptor βKlotho and its ability to activate FGFR1c/βKlotho complex was also unaffected. See FIGS. 6A and 6C.

The effects of FGF19/21$^{42-44}$ on hepatocyte proliferation was examined in vivo by measuring the incorporation of the label BrdU into hepatocytes post daily intraperitoneally (i.p.) injection of the recombinant protein for 7 days. Consistent with the previously observed link between liver FGFR4 activation and enhanced hepatocyte proliferation, histopathological examination of liver sections from FGF19/21$^{42-44}$ treated animals showed enhanced BrdU labeling in pericentral hepatocytes similar to FGF19 (FIG. 6E). There results indicate that additional regions of FGF19 can independently contribute to FGFR4 activation.

Figure 6C:
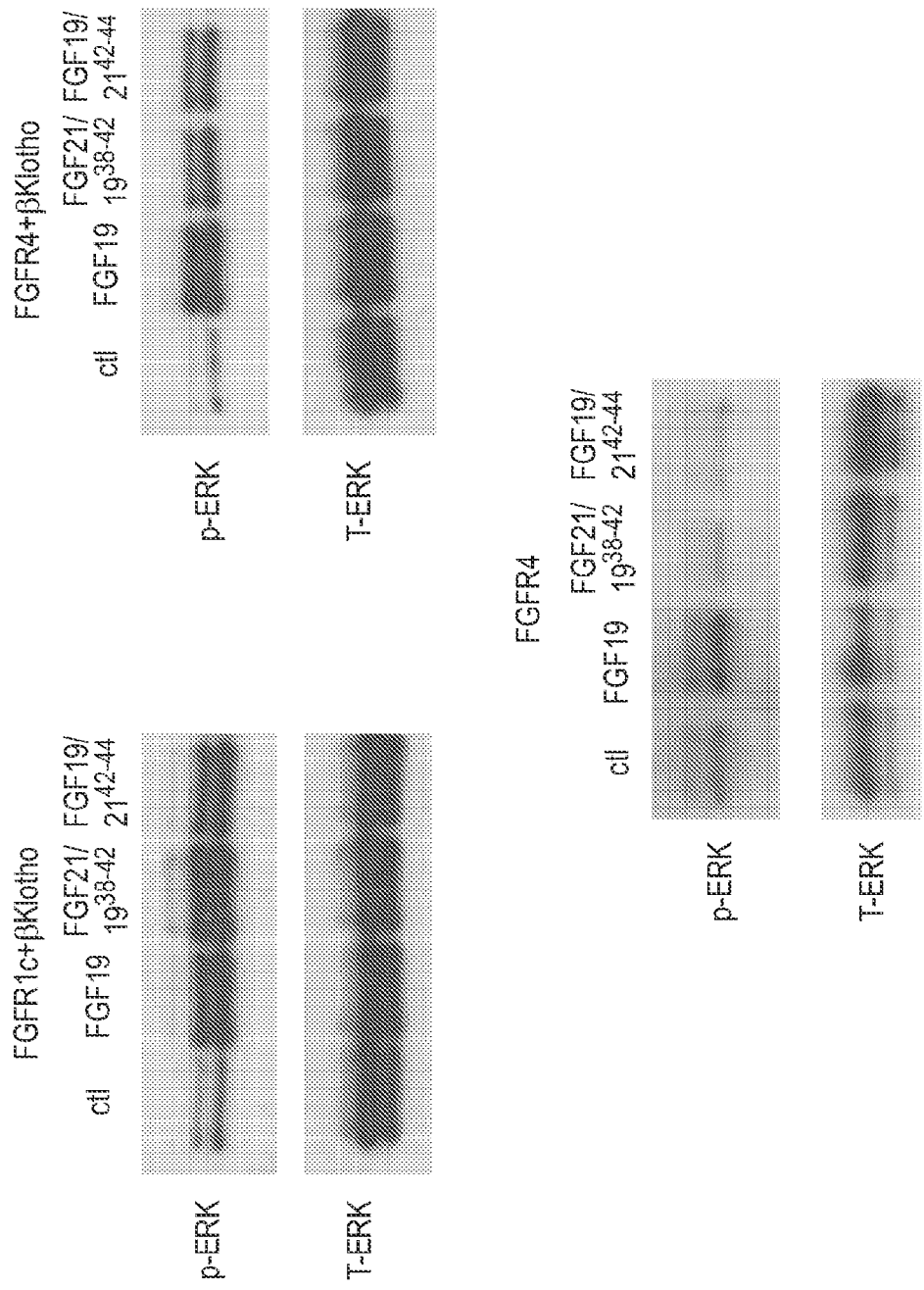
FIG. 6C is a series of Western blots showing FGFR1c and FGFR4-mediated activity of the FGF21/19$^{38\text{-}42}$ and FGF19/21$^{42\text{-}44}$ chimeric polypeptides.
Figures 1, 6D:
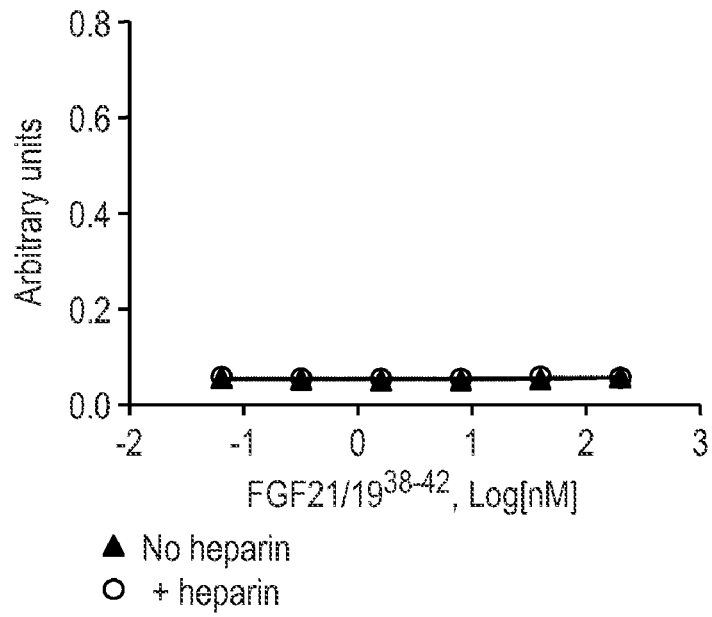
FIG. 1 shows the incorporation of BrdU by FGF19 and FGF21.
FIG. 6D is a series of plots showing the results of a solid-phase binding assay measuring the interaction between FGFR4 and FGF21/19$^{38\text{-}42}$ or FGF19/21$^{42\text{-}44}$ in the presence and absence of heparin.
Figures 2, 6D:
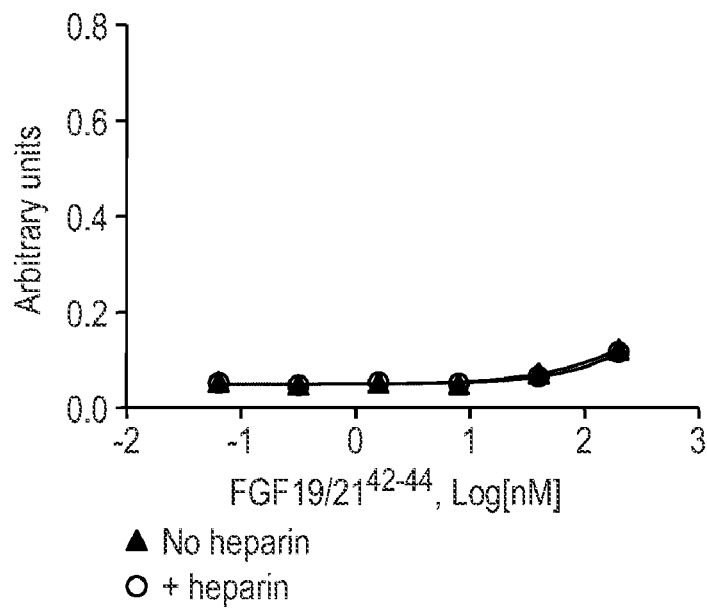
Figure 6E:
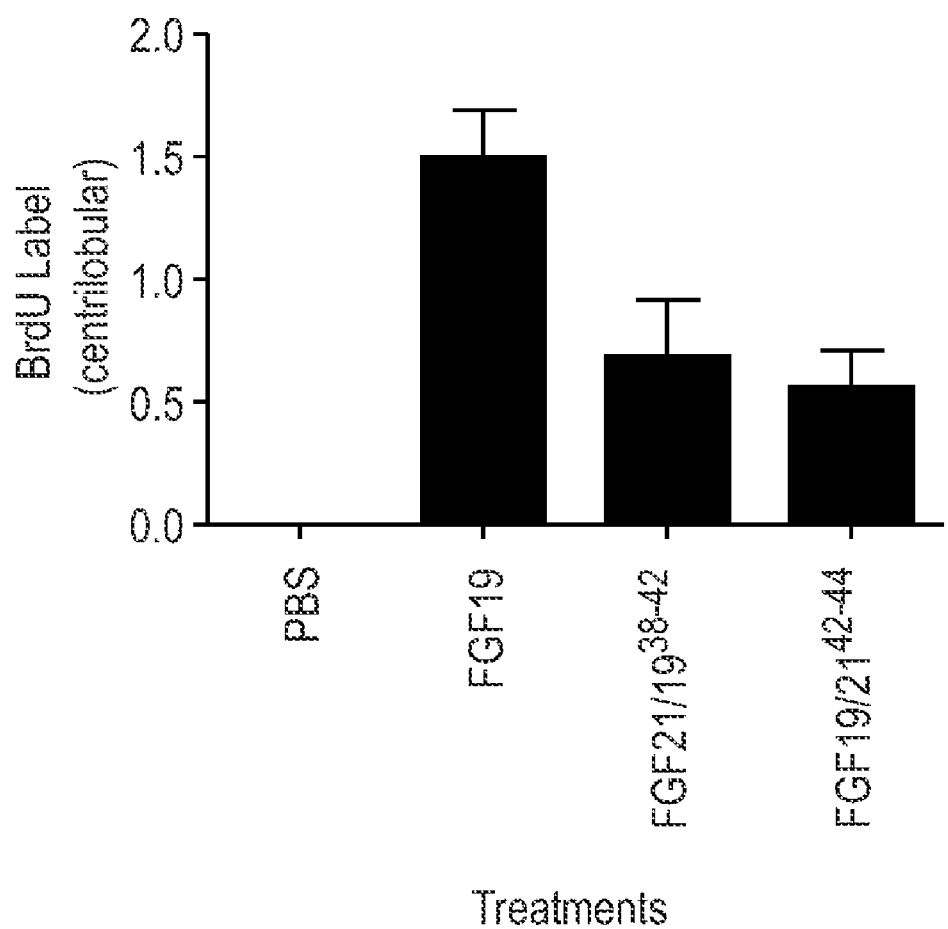
FIG. 6E is bar graph depicting the results of a semiquantitative analysis of BrdU immunostaining of livers from female FVB mice treated for 6 days with PBS, 2mg/kg/day recombinant FGF19, FGF21/19$^{38\text{-}42}$ or FGF19/21$^{42\text{-}44}$.

One surprising finding is that FGF19/21$^{42-44}$ is no longer able to activate FGFR4 in the absence of βKlotho (FIG. 6C lower panel FGFR4 alone transfection). This suggests that heparin induced FGF19/21$^{42-44}$/FGFR4 activation has been affected by this substitution. This is further confirmed by solid-phase binding assay where addition of heparin no longer stimulates FGF19/21$^{42-44}$ interaction with FGFR4 (FIG. 6D) similar to effects observed with mutations in the heparin binding sites of β1-β2 and β10-β12 regions shown in FIG. 7. Since FGF21/19$^{38-42}$ does not interact with or activate FGFR4 in the presence of heparin (FIG. 6D), the effect of the N-terminal 5 residues of FGF19 (38-42) on heparin induced FGFR4 interaction may be an indirect effect.

Example 8

Replacing Heparin Binding Loops in FGF19 Abolished βKlotho-Independent FGFR4 Activation by FGF19

FGF19 subfamily members have reduced affinity to heparin/heparin sulfate, and the presence of co-receptors a or βKlotho facilitate the binding and activation of FGFRs by this subfamily members to compensate for the weak heparin binding affinity. The only exception is the FGF19/FGFR4 interaction. At relatively high concentrations of heparin, FGF19 can bind and activate FGFR4 in the absence of βKlotho in both in vitro and in vivo.

The published apo-FGF19 and FGF23 structures (PDB codes:2P23 and 2P39; Goetz et al., (2007) Mol. Cell. Biol. 27:3417-28) provided some insights into the weakened affinity toward heparin for this subfamily. The β1-β2 loop (SEQ ID NOs:52, 54 and 56) and β10-β12 regions (SEQ ID NOs: 58, 60 and 62), which are shown in FIG. 7 and have been shown to be responsible for high affinity binding of heparin by other FGF family members, are much larger in this subfamily and could potentially form steric clashes with heparin in the ternary complex with FGFR, and therefore result in lower affinity toward heparin (Goetz et al., (2007) Mol. Cell. Biol. 27:3417-28).

A FGF21 model built based on the published apo-FGF19 structure revealed that in addition to the potential steric clash, the surface charges for FGF21 in these regions are also less favorable for heparin binding and may explain the even lower affinity of FGF21 toward heparin compared with FGF19 (Goetz et al., (2007) Mol. Cell. Biol. 27:3417-28). Since this is one of the major difference between FGF19 and FGF21, a modeled FGF19/FGFR structure based on the published FGF2/FGFR1 complex structure (PDB code: 1FQ9) revealed that these putative heparin binding domains are positioned opposite to the 5 amino acid residues at positions 38-42 in full length FGF19 and may also contact the receptor (Schlessinger et al., (2000) Mol. Cell. 6:743-50). In light of this observation, the issue of whether these regions contribute to FGFR4 activation by FGF19 was studied.

Figure 8A:
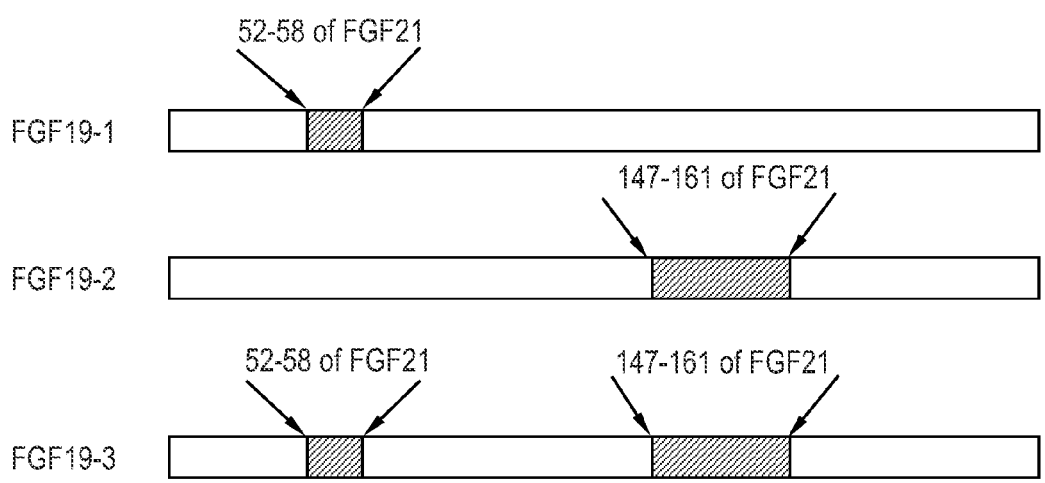
FIG. 8A is a graphical depiction of the three chimeric polypeptides FGF19-1, FGF19-2 and FGF19-3.

To examine the differences between FGF19 and FGF21 in the putative heparin binding domains, chimeric constructs in which the heparin interacting β1-β2 loop and β10-β12 segments in FGF19 were replaced with the corresponding sequences from FGF21 were designed and expressed. These chimeric constructs are shown graphically in FIG. 8A. In FIG. 8A, FGF19-1 corresponds to a chimera in which residues 52-58 of full length FGF21 (positions 24-30 in mature FGF21) replaced residues 50-57 of FGF19 (positions 28-35 in mature FGF19), FGF19-2 corresponds to a chimera in which residues 147-161 of full length FGF21 (positions 119-133 in mature FGF21) replaced residues 146-162 of FGF19 (positions 124-140 of mature FGF19) and FGF19-3 corresponds to a chimera in which residues 52-58 of full length FGF21 (positions 24-30 of mature FGF21) replaced residues 50-57 of full length FGF19 (positions 28-35 in mature FGF19) and residues 147-161 of full length FGF21 (positions 119-133 in mature FGF21) replaced residues 146-162 of full length FGF19 (positions 124-140 of mature FGF21). These chimeric polypeptides were used to investigate the contribution of these domains to heparin binding and FGFR4 activation.

Figure 8B:
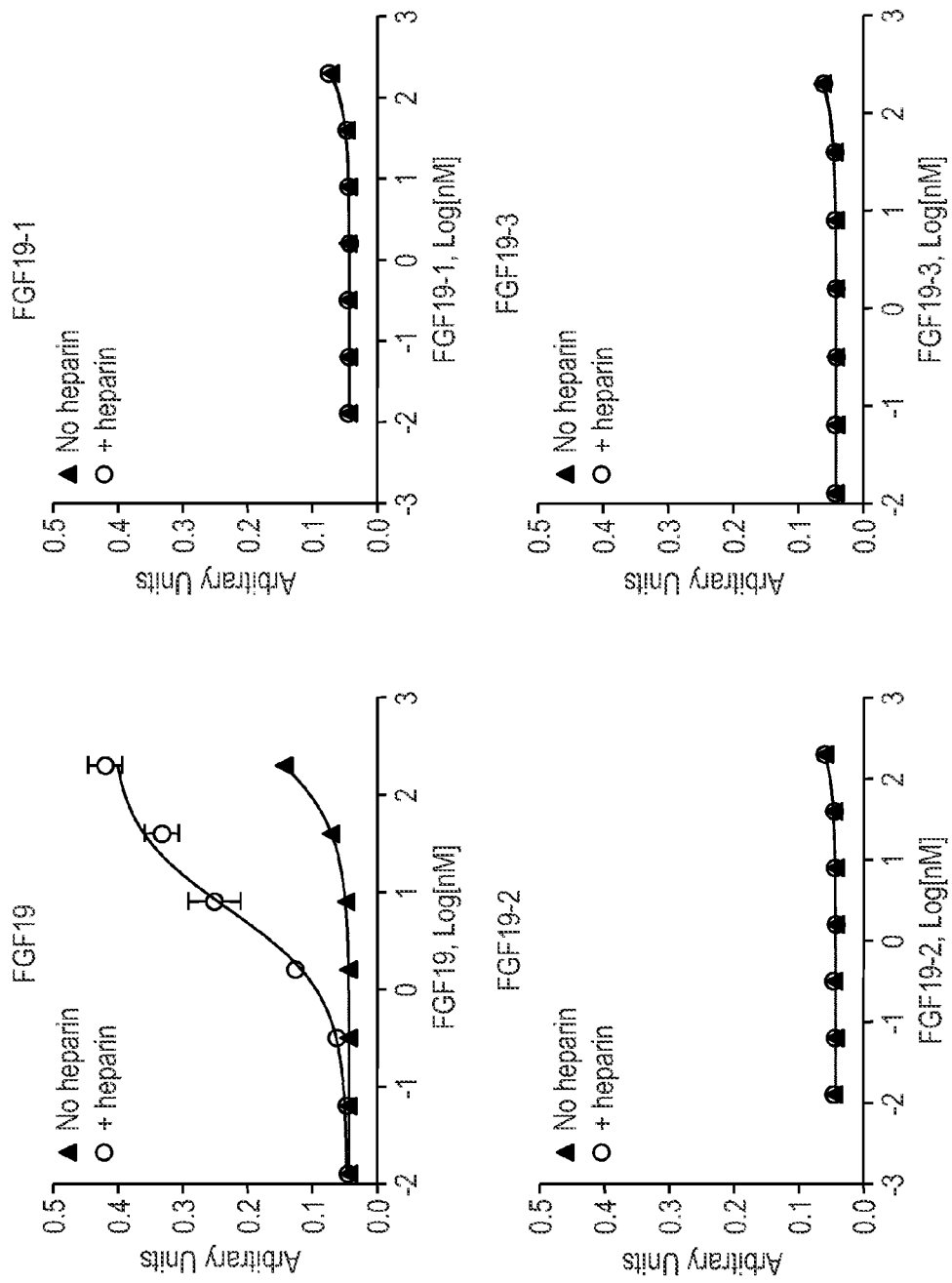
FIG. 8B is a series of plots showing the glucose lowering effect of the FGF19-1, FGF19-2 and FGF19-3 constructs in the presence and absence of heparin.
Figure 8C:
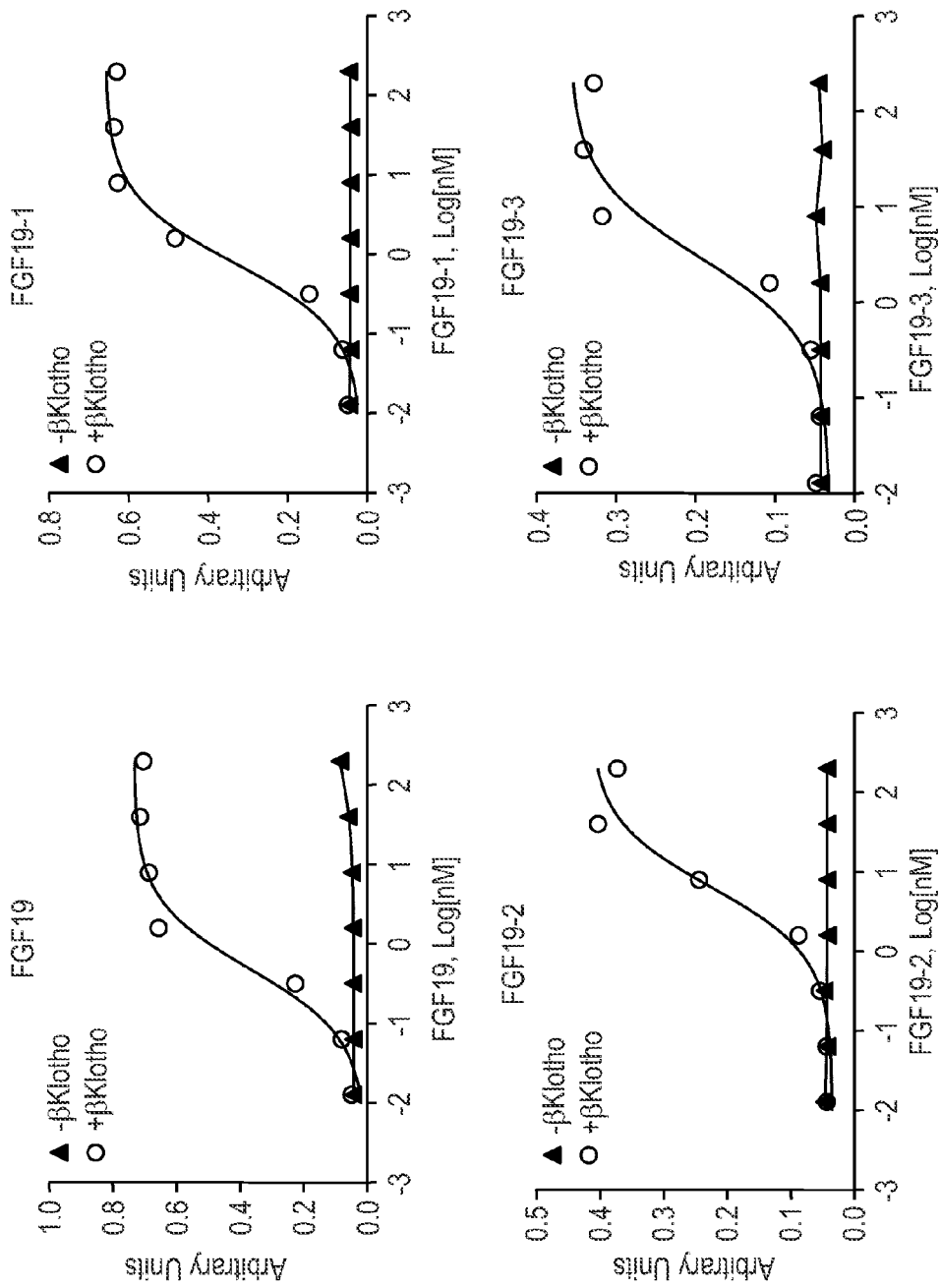
FIG. 8C is a series of plots showing the glucose lowering effect of the FGF19-1, FGF19-2 and FGF19-3 constructs in the presence and absence of βKlotho.

As demonstrated by the results of a solid-phase binding assay, replacing the β1-β2 loop and β10-β12 segment of FGF19 individually or in combination abolished heparin induced FGF19/FGFR4 interaction (FIG. 8B) while preserving the ability to interact with FGFR4 in the presence of βKlotho (FIG. 8C), is consistent with the roles of these two regions in interacting with heparin.

To further evaluate these findings in a functional assay, receptors were again transfected into L6 cells. FGFR4 was either transfected alone or together with βKlotho, and the signaling was monitored by the ERK phosphorylation levels. Consistent with solid-phase binding results, in contrast to FGF19, the chimeric substitutions in these putative heparin binding domains abolished heparin dependent FGFR4 activation (FIG. 8D, lower panel), while βKlotho dependent FGFR1c and FGFR4 activation were preserved (FIG. 8D upper panels). These results indicate that the mutations in the putative heparin binding domain indeed abolished heparin dependent receptor activities.

It has been shown that wild type FGF19 can activate FGFR4 either through heparin or βKlotho. One variant of FGF19, namely FGF19dCTD, can selectively activate FGFR4 only in a heparin dependent manner, and this activation still induced enhanced hepatocyte proliferation. In the case of FGF19-1 mutant described herein, the heparin dependent FGFR4 activation was abolished while preserving βKlotho dependent FGFR4 activation. With respect to FGF19dCTD and FGF19-1, each appeared to retain part of the wild type FGF19 function, and although both are able to activate FGFR4, signaling is mediated through different cofactors.

Figure 8E:
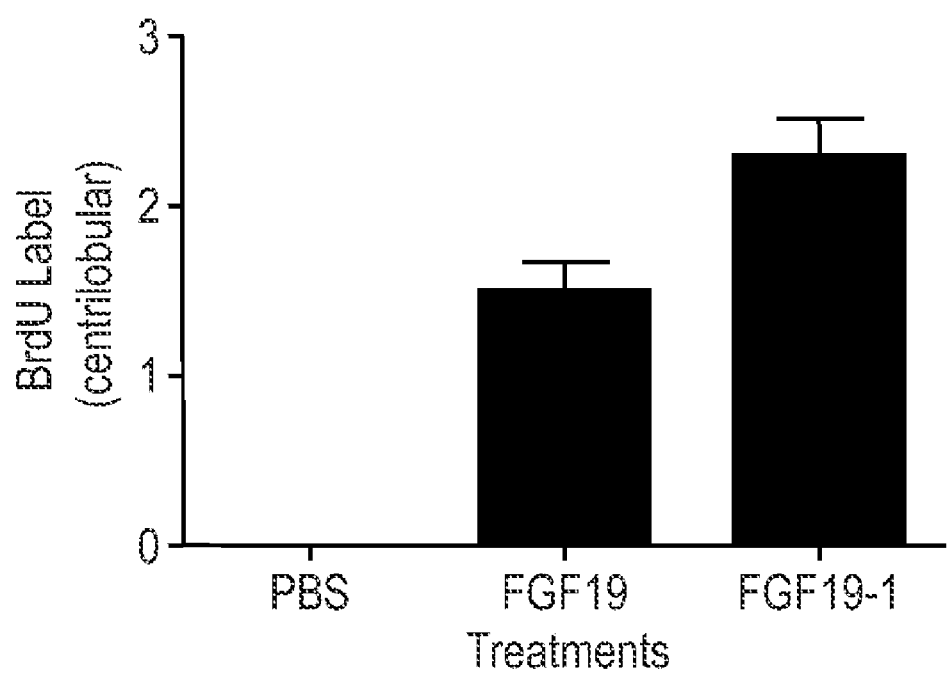
FIG. 8E is a bar graph showing BrdU incorporation mediated by FGF19 and FGF19-1.

The issue of whether there is a qualitative difference in FGFR4 signaling mediated through βKlotho versus signaling mediated through heparin with respect to stimulation of hepatocyte proliferation was then studied. Histopathological examination of liver sections from FGF19-1 treated animals showed enhanced BrdU labeling in pericentral hepatocytes similar to FGF19 treatment (FIG. 8E), suggesting that both heparin and βKlotho induced FGFR4 activation results in enhanced hepatocyte proliferation. As is the case with wild type FGF19, FGF19-1 is also still active in other metabolic assays, able to induce glucose uptake into adipocyte cells and reduced plasma glucose levels in an ob/ob diabetic animal model, indicating that heparin domain mutations did not affect other FGF19 mediated functions.

Example 9

Figure 9A:
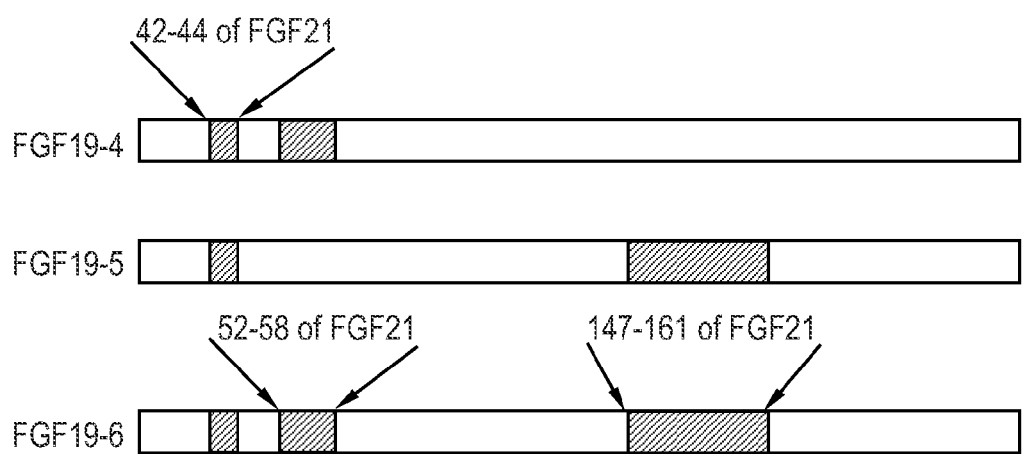
FIG. 9A is a graphical depiction of the three chimeric polypeptides FGF19-4, FGF19-5 and FGF19-6.

A Chimeric Protein in which Residues 38-42 of Full Length FGF19 and Both Heparin Binding Regions in FGF19 are Replaced Exhibits Decreased FGFR4 Activation and Hepatocyte Proliferation The single changes in the 5 amino acid region of residues 38-42 of full length FGF19 (positions 14-20 in mature FGF19) and the heparin binding domains did not completely abolish FGFR4 activation, so a chimeric protein in which the replacement of all three of these regions was studied. Additional chimeric polypeptides combining residues 38-42 of full length FGF19 and one or both of the heparin interaction regions were constructed and expressed. These chimeric polypeptides were designated FGF19-4, FGF19-5 and FGF19-6, respectively, and are shown graphically in FIG. 9A. The activities of these chimeric polypeptides were tested in vitro and in vivo assays.

These combination chimeric polypeptides were no longer able to activate FGFR4 signaling in L6 cells in the absence or presence of βKlotho but were still able to activate FGFR1c signaling (FIG. 9B), therefore, selectively abolishing FGFR4 activity. Consistent with this observation, histopathological examination of liver sections from FGF19-4, -5, and -6, treated animals did not show increased numbers of BrdU-labeled hepatocytes in pericentral regions, nor was increased BrdU labeling noted in any other area of the liver (FIG. 9C). Therefore, enhanced hepatocyte proliferation associated with wild type FGF19 was abolished by the combined mutagenesis of the 5 FGF19 amino acid residues WGDPI and heparin domains.

To rule out the possibility that the lack of positive BrdU labeling is due to differences in the degradation and clearance of the chimeric proteins in serum, the serum concentration of the chimeras was measured at various time points after injection into the mice and similar pharmacokinetic properties of the chimeric proteins to wild type FGF19 were observed.

Example 10

Chimeric Molecules Lacking the Ability to Activate FGFR4 can Still Regulate Glucose Homeostasis Since the chimeric FGF19 molecules FGF19-4, FGF19-5, and FGF19-6, which comprise the combined substitutions of the 5 amino acids from positions 38-42 of full length FGF19, namely residues WGDPI, and also one or both of the heparin binding domains, were still able to activate FGFR1c/βKlotho receptor signaling in L6 cells (FIG. 9B), their ability to regulate glucose homeostasis was tested.

Figure 10C:
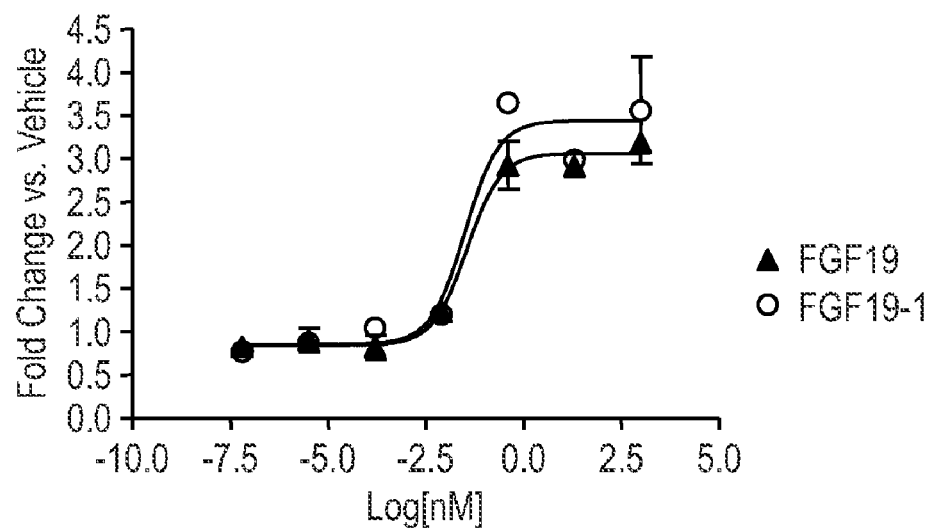
FIG. 10C depicts the effect of FGF19 and the FGF19-1 chimeric polypeptide on glucose uptate in a 3T3L1 cell-based assay.

The effect of these chimeric proteins on glucose uptake into adipocytes was first tested. Similar to wild type FGF19 protein, the chimeric proteins were also able to stimulate glucose uptake independent of insulin into 3T3L1 adipocytes in vitro (FIG. 10A).

To further investigate the ability of the chimeric proteins to regulate glucose homeostasis, ob/ob mice were injected intraperitoneally with FGF19 or FGF19-4 and blood glucose levels were measured at 0, 1, 3, and 5 hrs post injection; the values are reported as area under the curve (AUC) means±S.E.M. over this time period (FIG. 10B). Plasma glucose levels were significantly reduced in mice injected with both FGF19 and FGF19-4 with comparable potency and efficacy (FIG. 10B). These results indicate that FGF19-4 only selectively lost its ability to induce FGFR4 mediated hepatocyte proliferation, but retained its ability to modulate glucose regulation.

Figure 10D:
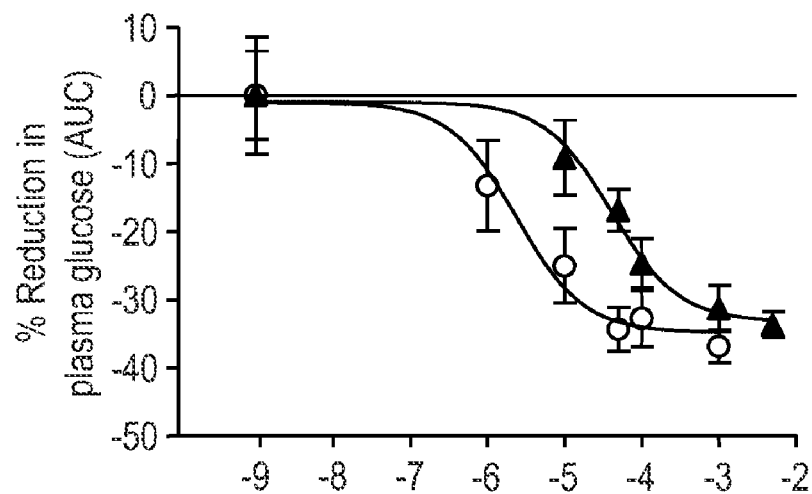
FIG. 10D shows the effect of FGF19 and FGF19-1 on plasma glucose in a ob/ob mouse model.
Figure 13A:
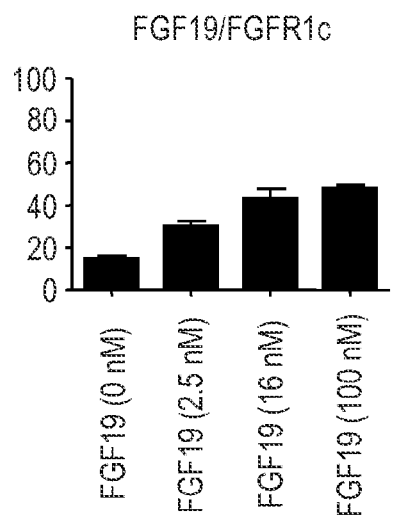
FIG. 13 is a series of bar graphs showing FGFR1c-induced activity of several FGF19 mutants having one or more mutations or deletions in the WGDPI (SEQ ID NO:49) region; each construct was tested at concentrations of 0, 2.5, 16 and 100 nM.
Figure 13B:
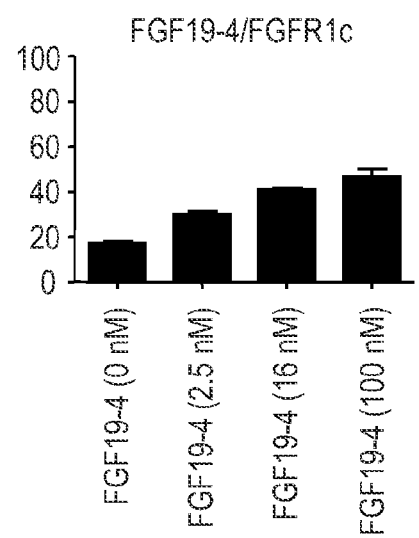
Figure 13C:
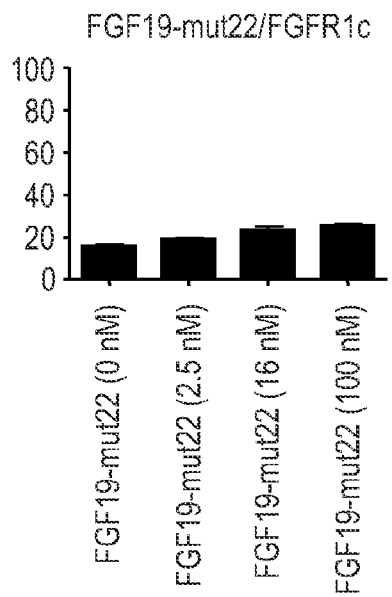
Figure 13D:
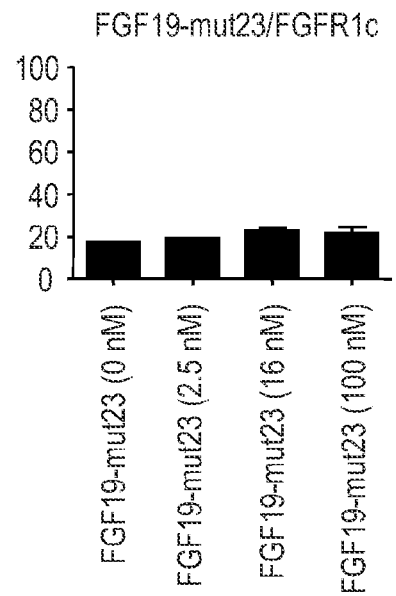
Figure 13E:
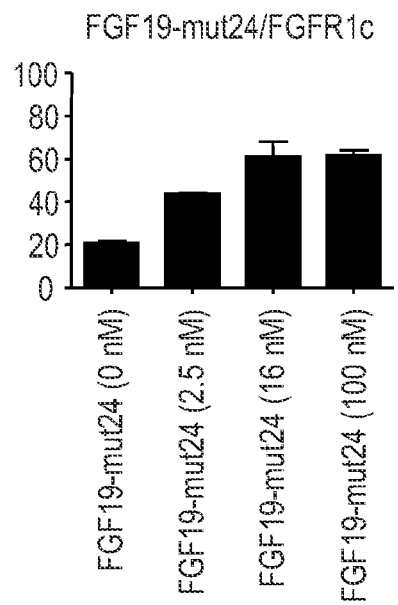
Figure 13F:
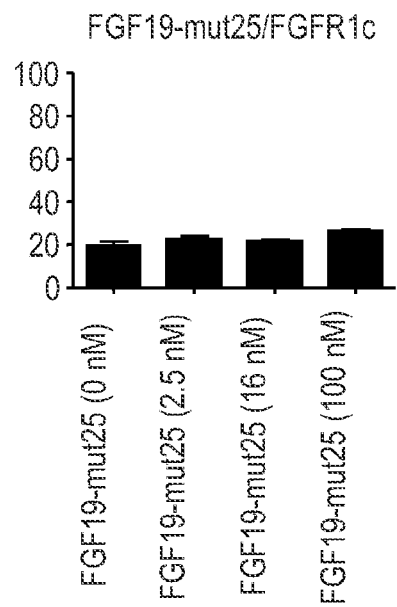
Figure 13G:
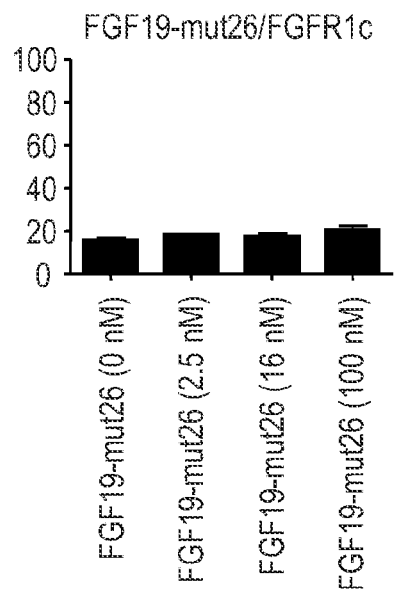
Figure 13H:
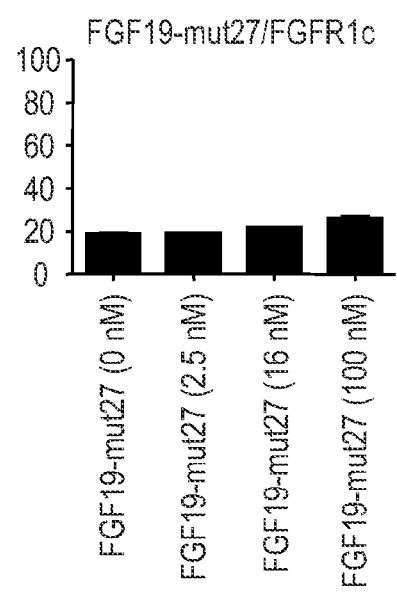
Figure 13I:
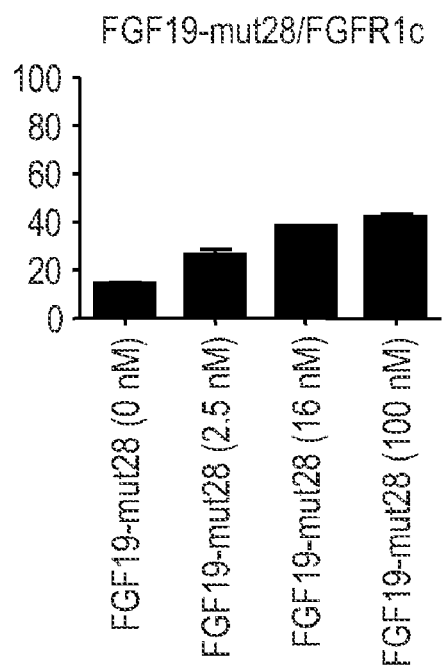
Figure 13J:
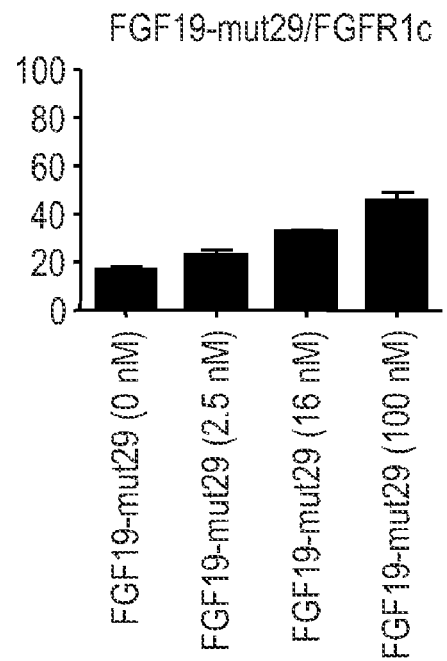
Figure 13K:
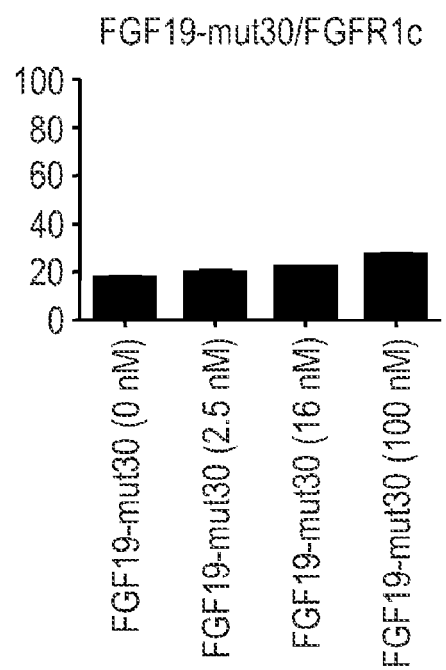
Figure 14E:
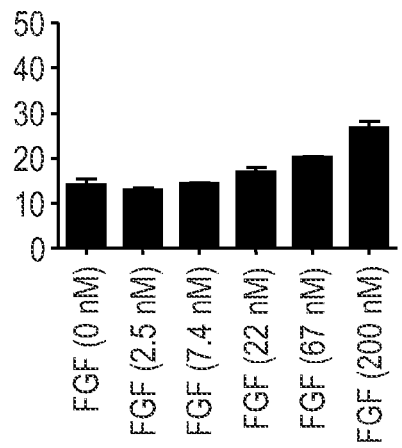
FIG. 14 is a series of bar graphs showing FGFR1c-mediated activity of several FGF19 mutants having one or more mutations or deletions in the WGDPI (SEQ ID NO:49) region; each construct was tested at concentrations of 0, 2.5, 7.4, 33, 67 and 200 nM.
Figure 14F:
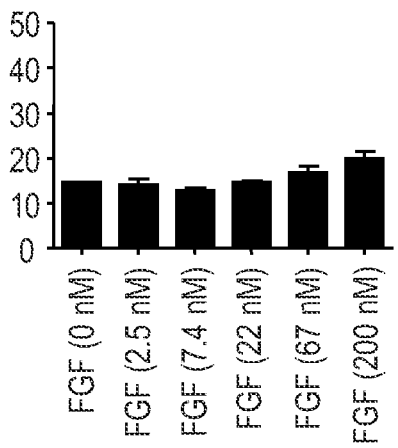
Figure 14G:
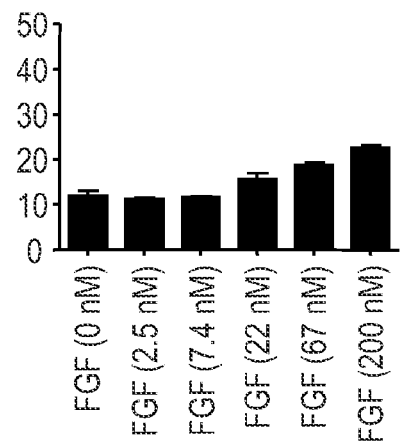
Figure 14H:
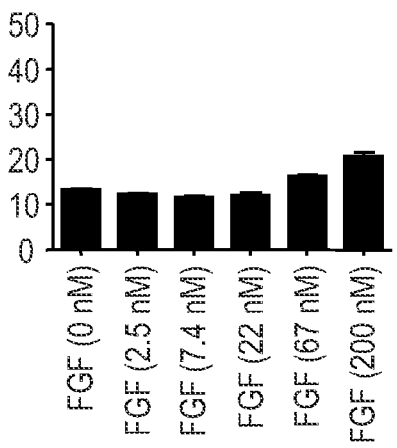
Figure 15A:
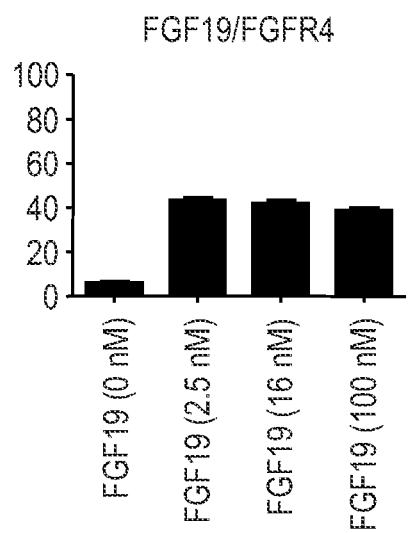
FIG. 15 is a series of bar graphs showing FGFR4-mediated activity of several FGF19 mutants having one or more mutations or deletions in the WGDPI (SEQ ID NO:49) region; each construct was tested at concentrations of 0, 2.5, 16 and 100 nM.
Figure 15B:
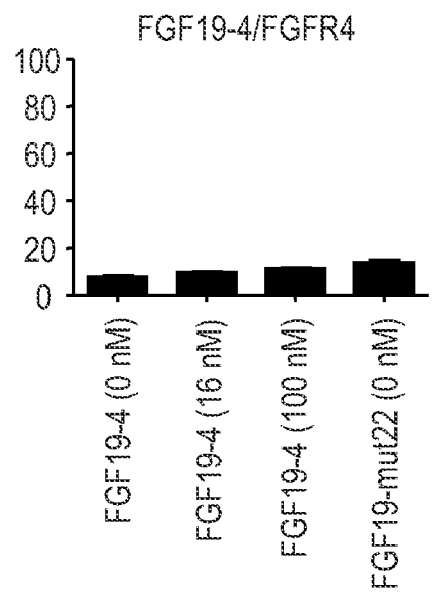
Figure 15C:
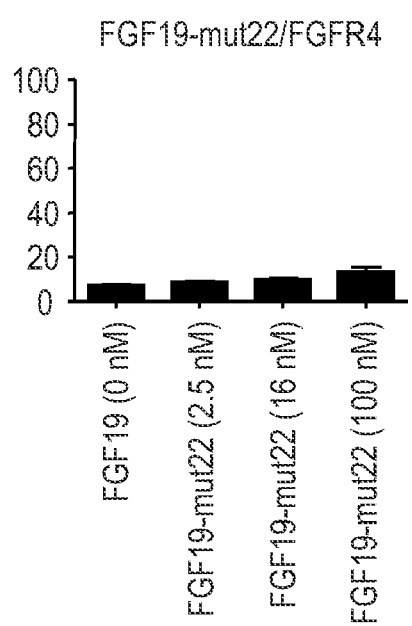
Figure 15D:
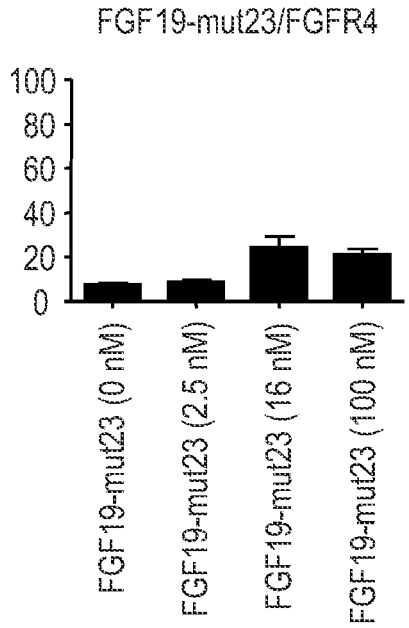
Figure 15E:
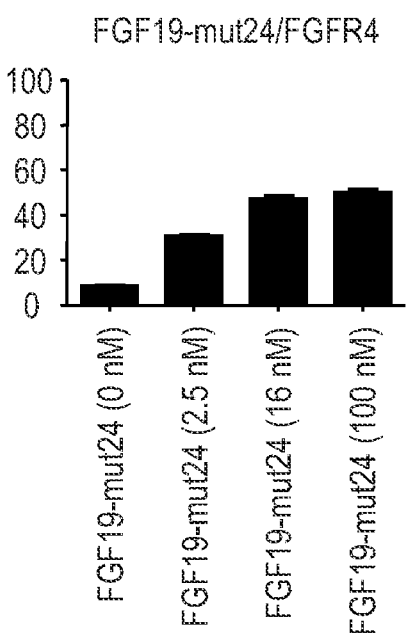
Figure 15F:
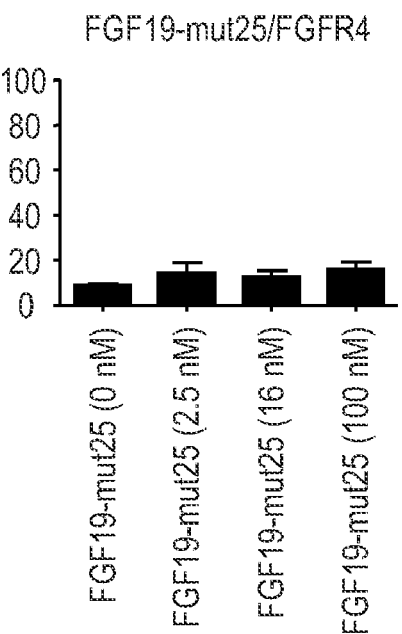
Figure 15G:
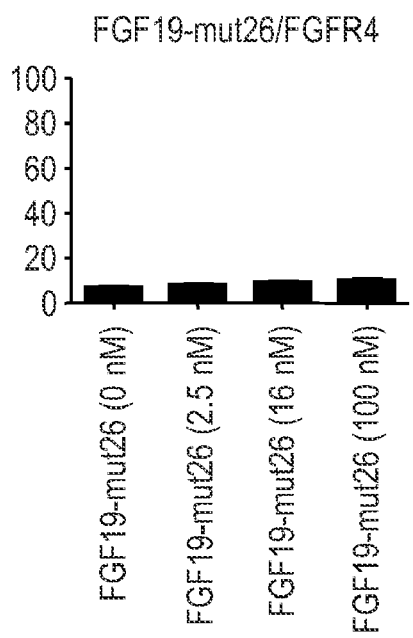
Figure 15H:
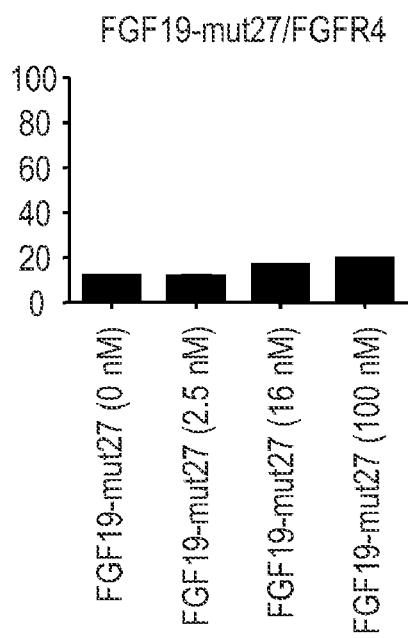
Figure 15I:
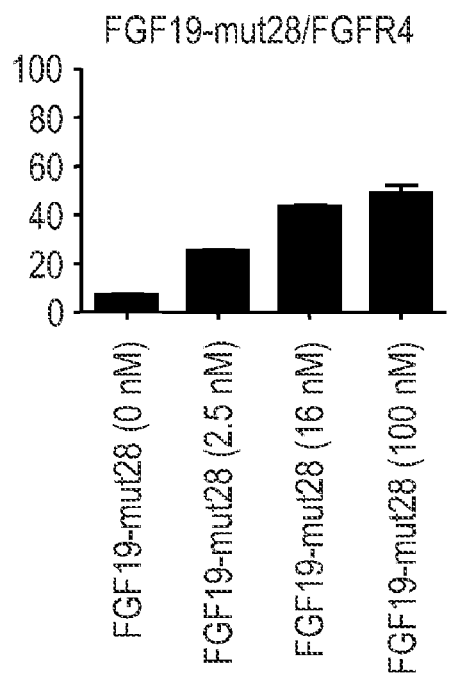
Figure 15J:
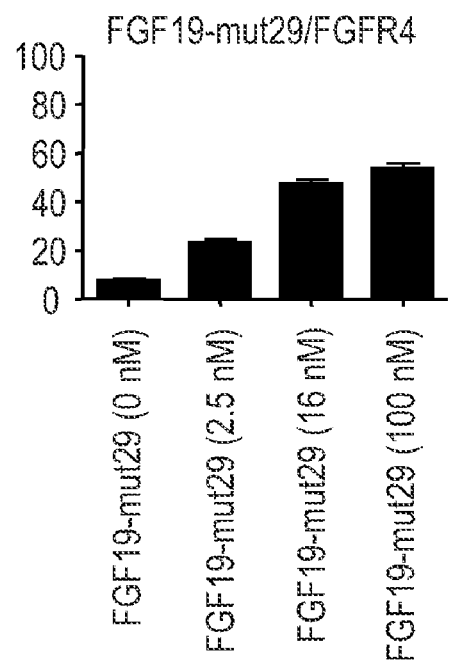
Figure 15K:
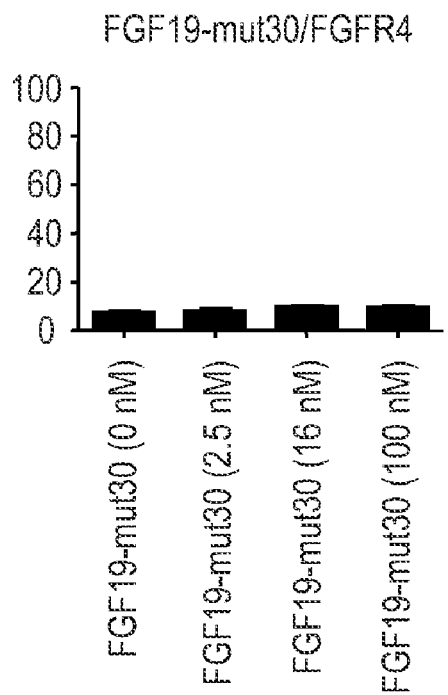
Figure 16E:
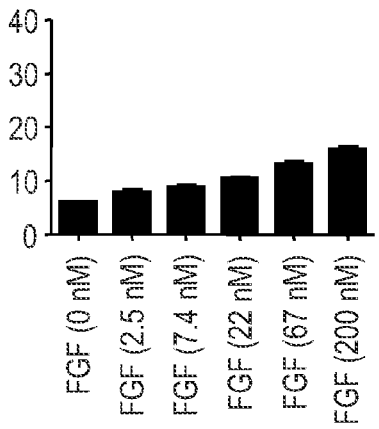
FIG. 16 is a series of bar graphs showing FGFR4-mediated activity of several FGF19 mutants having one or more mutations or deletions in the WGDPI (SEQ ID NO:49) region; each construct was tested at concentrations of 0, 2.5, 7.4, 22, 67 and 200 nM.
Figure 16F:
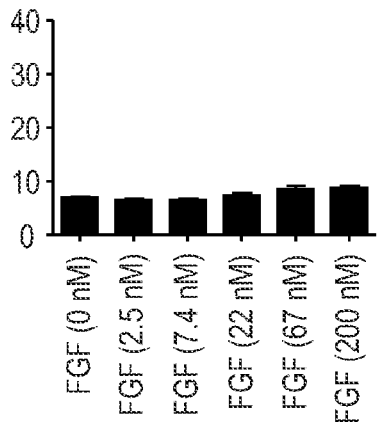
Figure 16G:
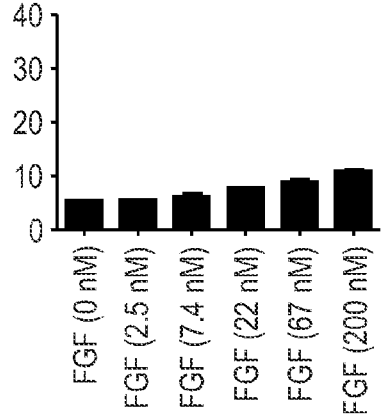
Figure 16H:
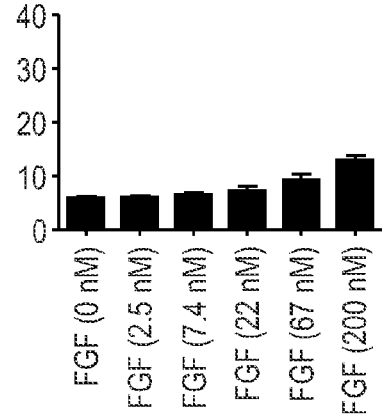

Replacing the β1-β2 loop segment of FGF19 only (FGF19-1) abolished heparin induced FGF19/FGFR4 interaction while preserving the ability to interact with FGFR4 in the presence of βKlotho. Similar to wild type FGF19, FGF19-1 is also still active in other metabolic assays, able to induce glucose uptake into adipocyte cells (FIG. 10C) and reduced plasma glucose levels in ob/ob diabetic animals model (FIG. 10D), suggesting that heparin domain mutations did not affect other FGF19 mediated functions.

Example 11

Pharmacokinetic Analysis of the Chimeric Proteins

The pharmacokinetic profiles of the chimeric constructs FGF19/21-1, FGF19/21-2, FGF19/21-3, FGF19/21-4 and FGF19/21-5 were studied. The following protocol was employed. Following i.p. injections of 2 mg/kg FGF19/21 chimeric proteins (n=5), C57BL6 mouse serum samples were collected 15 min, 1 hour, 3 hours, and 6 hours after the injections. FGF19/21 chimeric protein concentrations were determined by an enzyme-linked immunosorbent assay (ELISA) developed at Amgen. The antibodies used as capture and detection reagents were generated in-house. A mouse monoclonal antibody raised against human FGF21 was used as the capture antibody and was specific for an epitope near the C-terminus on human FGF21. A biotin-conjugated rabbit polyclonal antibody raised against human FGF21 was used as the detection antibody and recognized multiple epitopes on human FGF21.

The ELISA was performed as follows. The capture antibody was bound onto a 96-well polystyrene microplate. Standards and quality control samples were prepared by spiking the FGF19/21 chimera into mouse plasma. Standards, quality controls, matrix blank, and unknown samples were loaded into the wells after pretreatment in assay buffer. After a two hour incubation followed by washing, the biotin-conjugated detection antibody was added to the wells. After a one hour incubation followed by washing, a streptavidin-horseradish peroxidase (HRP) conjugate (R&D Systems, Inc) was added to the wells. After a 30 minute incubation followed by washing, a tetramethylbenzidine (TMB) peroxidase substrate solution was added to the wells. In the presence of HRP, a colorimetric signal was produced that was proportional to the amount of FGF19/21 chimera bound by the capture antibody. The color development was stopped and the intensity of the color (optical density, OD) was measured at 450-650 nm with a plate reader. The conversion of OD units to concentration for the unknown samples was achieved through a software-mediated comparison to a standard curve assayed on the same plate. The data were regressed using SoftMax Pro 5 (Molecular Devices Corp.) data reduction package.

The results of the study are presented in FIG. 11.

Example 12

Deletion or Mutation of FGF19 Residue W38 Abolishes FGFR4 and FGFR1c Function 16 mutants within the residues WGDPI (SEQ ID NO:49) region at positions 38-42 of the FGF19-1 polypeptide (in which residues 50-57 of FGF19 were replaced with residues 52-58 of FGF21; see FIG. 8) were expressed and purified as described in Example 1. L6 cells transfected with either FGFR1c/βKlotho or FGFR4/βKlotho were treated with those purified proteins. Activities of mutants on FGFR1c or FGFR4 were determined by measuring ERK phosphorylation levels 15 min after treatments and are summarized in FIG. 12.

The bar graphs of FIG. 13 reflects the level of FGFR1c-mediated activity of FGF19 mutants administered at concentrations of 0, 2.5, 16 and 100 nM. The bar graphs of FIG. 14 reflects the level of FGFR1c-mediated activity of FGF19 mutants administered at concentrations of 0, 2.5, 7.4, 44, 67 and 200 nM.

The bar graphs of FIG. 15 reflect the level of FGFR4-mediated activity of FGF19 mutants administered at concentrations of 0, 2.5, 16 and 100 nM. The bar graphs of FIG. 15 reflects the level of FGFR4-mediated activity of FGF19 mutants administered at concentrations of 0, 2.5, 7.4, 44, 67 and 200 nM.

Deletion of W38, P41, and I42 abolished activation of both FGFR1c and FGFR4 receptor by the mutant FGF19 proteins, while deletion of G39 reduced activity on both receptors and deletion of D40 selectively removed FGFR1c activity with much less effect on FGFR4 activity.

Each of the 5 amino acids was then individually mutated to alanine to study their involvement in receptor activation.

While some of the mutations in the GDPI (SEQ ID NO:71) sequence to alanine affected either potency and/or efficacy, only W38A completely abolished activation of both FGFR1c and FGFR4.

The results of this study indicate that W38 is a critical residue for FGF19-induced FGFR activation. The results further indicate that deletion or mutagenesis of this residue to selectively decrease or remove FGFR4-mediated activity from FGF19 would require a change from wild type at position 38, particularly a deletion or mutation. This decrease in FGFR4-mediated activity may be achievable by mutating or deleting W38 alone or may require additional deletions or mutations in the WGDPI or surrounding region. One such example is FGF19-4 (residues 38-42 of FGF19 were replaced with residues 42-44 of FGF21 and residues 50-57 of FGF19 were replaced with residues 52-58 of FGF21; see FIG. 8) in which concurrent deletion of W38, P41 and mutation of I42V resulted in such selective FGFR1c-mediated activity.

By mitigating the mitogenicity of FGF19, a mutant form of FGF19 comprising a mutation or deletion at position 38 could make FGF19 a therapeutically relevant molecule and an attractive candidate for pharmaceutical development.

---

What is claimed is:

1. A polypeptide comprising SEQ ID NO:4 wherein the residues WGDPI (SEQ ID NO:49) at positions 16-20 of SEQ ID NO:4 are substituted with one of GQV, GDI, GPI, SEQ ID NO:71, SEQ ID NO:73, SEQ ID NO:84, SEQ ID NO:76, SEQ ID NO:80, SEQ ID NO:81, SEQ ID NO:82 and SEQ ID NO:83.

2. A polypeptide comprising SEQ ID NO:4 wherein residues SGPHGLSS (SEQ ID NO:52) at positions 28-35 of SEQ ID NO:4 are substituted with DDAQQTE (SEQ ID NO:54).

3. A polypeptide comprising SEQ ID NO:4 wherein residues SSAKQRQLYKNRGFLPL (SEQ ID NO:58) at positions 124-140 of SEQ ID NO:4 are substituted with PGNKSPHRDPAPRGP (SEQ ID NO:60).

4. A polypeptide comprising SEQ ID NO:4, wherein the residues WGDPI (SEQ ID NO:49) at positions 16-20 of SEQ ID NO:4 are substituted with one of GQV, GDI, GPI, SEQ ID NO:71, SEQ ID NO:73, SEQ ID NO:84, SEQ ID NO:76, SEQ ID NO:80, SEQ ID NO:81, SEQ ID NO:82 and SEQ ID NO:83; and one or both of:
   (i) the residues SGPHGLSS (SEQ ID NO:52) at positions 28-35 of SEQ ID NO:4 are substituted with DDAQQTE (SEQ ID NO:54); and
   (ii) the residues SSAKQRQLYKNRGFLPL (SEQ ID NO:58) at positions 124-140 of SEQ ID NO:4 are substituted with PGNKSPHRDPAPRGP (SEQ ID NO:60).

5. A polypeptide comprising SEQ ID NO:4 wherein the residues WGDPI (SEQ ID NO:49) at positions 16-20 of SEQ ID NO:4 are substituted with GQV; and one or both of:
   (a) the residues SGPHGLSS (SEQ ID NO:52) at positions 28-35 of SEQ ID NO:4 are substituted with DDAQQTE (SEQ ID NO:54); and
   (b) the residues SSAKQRQLYKNRGFLPL (SEQ ID NO:58) at positions 124-140 of SEQ ID NO:4 are substituted with PGNKSPHRDPAPRGP (SEQ ID NO:60).

6. A nucleic acid molecule encoding the chimeric polypeptide of claim 1, 2, 3, 4 or 5.

7. A vector comprising the nucleic acid molecule of claim 6.

8. A host cell comprising the nucleic acid molecule of claim 6.

9. A pharmaceutical composition comprising the polypeptide of claim 1, 2, 3, 4 or 5 and a pharmaceutically acceptable carrier.

10. A fusion polypeptide comprising the polypeptide of claim 1, 2, 3, 4 or 5 fused to a heterogenous moiety.

11. The fusion polypeptide of claim 10, wherein the heterogenous moiety is an Fc region of an IgG molecule or a PEG molecule.

12. The polypeptide of claim 1, 2, 3, 4 or 5, wherein SEQ ID NO:4 is truncated on the N terminus by 1-15 amino acids, the C terminus by 1-15 amino acids, or on both the N terminus by 1-15 amino acids and the C terminus by 1-15 amino acids.

* * * * *